United States Patent
Straub et al.

(10) Patent No.: US 6,933,295 B2
(45) Date of Patent: Aug. 23, 2005

(54) SUBSTITUTED ISOINDOLES AND THE USE THEREOF

(75) Inventors: Alexander Straub, Wuppertal (DE); Thomas Lampe, Düsseldorf (DE); Jens Pohlmann, Wuppertal (DE); Susanne Röhrig, Essen (DE); Stephan Jordan, Köln (DE); Elisabeth Perzborn, Wuppertal (DE); Karl-Heinz Schlemmer, Wuppertal (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/484,369

(22) PCT Filed: Jul. 3, 2002

(86) PCT No.: PCT/EP02/07326

§ 371 (c)(1),
(2), (4) Date: Jul. 19, 2004

(87) PCT Pub. No.: WO03/007942

PCT Pub. Date: Jan. 30, 2003

(65) Prior Publication Data

US 2005/0004207 A1 Jan. 6, 2005

(30) Foreign Application Priority Data

Jul. 16, 2001 (DE) .......................................... 101 34 482

(51) Int. Cl.[7] .................... C07D 409/12; C07D 409/14; C07D 471/04; C07D 487/04; A61K 31/4035

(52) U.S. Cl. .................... 514/235.2; 514/258; 514/303; 514/339; 514/393; 514/394; 514/397; 514/406; 514/414; 544/144; 544/256; 544/333; 546/200; 546/277.1; 548/305.1; 548/312.1; 548/364.7; 548/467

(58) Field of Search ................................ 544/144, 256, 544/333; 546/200, 277.1; 548/305.1, 312.1, 364.7, 467; 514/235.2, 258, 339, 393, 394, 397, 406, 414

(56) References Cited

U.S. PATENT DOCUMENTS 6,140,351 A  10/2000 Arnaiz et al. ............... 514/336
2004/0215019 A1 * 10/2004 Straub et al. ............... 546/200

FOREIGN PATENT DOCUMENTS

| WO | 9906371 | 2/1999 | ......... C07D/213/82 |
| WO | 9900121 | 7/1999 | |
| WO | 9937304 | 7/1999 | ......... A61K/31/505 |
| WO | WO-03/011585 | * 2/2003 | |

OTHER PUBLICATIONS

Al–Obeidi, F., and Ostrem, J. A., "Factor Xa Inhibitors", Exp. Opin. Ther. Patents, 9(7): 931–953 (1999).
Betz, A., "Recent advances in Factor Xa inhibitors", Exp. Opin. Ther. Patents, 11(6): 1007–1017 (2001).
Hauptmann, et al., "Synthetic Inhibitors of Thrombin and Factor Xa: From Bench to Bedside," Thrombosis Res. *93*, 203–241, (1999).
Al–Obeidi, et al., "Factor Xa Inhibitors by Classical and Combinatorial Chemistry", DDT, *3*, 223–231, (1998).
Al–Obeidi, et al., "Factor Xa Inhibitors", Exp. Opin. Ther. Patents *9*, 931–953, (1999).
Kaiser, "Thrombin and Factor Xa Inhibitors," Drugs of the Future, *23*, 423–436, (1998).
Uzan, "Antithrombotic Agents," Emerging Drugs, *3*, 189–208, (1998).
Zhu, et al., "Recent Advances in Inhibitors of Factor Xa in the Prothrombinase Complex", Curr. Opin. in Cardiovas. Pul. & Renal Investigational Drugs, *1*, 63–88, (1999).
Ullman's Encyclopedia of Industrial Chemistry, Published by VCH Verlagsgesellschaft, Wernheim, 1985–1996; Key word "Vitamin K.".
Pschyrembel Klinisches Wortherbuch, 257, Published by Walter de Gryuter, 1994, pp. 199–200; Keyword: "Blutgerinnung".
Pschyrembal Klinisches Worterbuch, 257, Published by Walter de Gruyter, 1994; pp. 610; Keyword: "Heparin".
Pschyrembel Klinisches Worterbuch, 257, Published by Walter de Gruyter, 1994; pp. 292–293, Keyword: "Cumarinderivate".
Römpp Lexikon Chemie, Version 1.5, 1998; Georg Thieme, Publisher, Stutgart; Key Word "Blutgerinnung"; Stryer, L., Biochemie, Spectrum der Wissenschaft Verlagsgesellschaft mGH Heidelberg; 1990, pp. 259–260.

* cited by examiner

*Primary Examiner*—Fiona T. Powers

(57) ABSTRACT

The invention relates to the field of blood clotting, to novel compounds of formula (I),

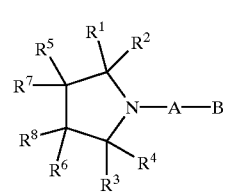

to a method for their production and to the use of these compounds as active ingredients in medicaments for preventing and/or treating diseases. The compounds are factor Xa inhibitors.

13 Claims, No Drawings

SUBSTITUTED ISOINDOLES AND THE USE THEREOF

The present invention relates to the field of blood coagulation. In particular, the present invention relates to novel isoindole derivatives, to processes for their preparation and to their use as active compounds in medicaments.

Blood coagulation is a protective mechanism of the organism which helps to "seal" defects in the wall of the blood vessels quickly and reliably. Thus, loss of blood can be avoided or kept to a minimum. Hemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a joint reaction path, are distinguished. Here factor Xa, which is formed from the proenzyme factor X, plays a key role, since it connects the two coagulation paths. The activated serine protease Xa cleaves prothrombin to thrombin. The resulting thrombin, in turn, cleaves fibrinogen to fibrin, a fibrous/gelatinous coagulant. In addition, thrombin is a potent effector of platelet aggregation which likewise contributes significantly to hemostasis.

Maintenance of normal hemostasis—between bleeding and thrombosis—is subject to a complex regulatory mechanism. Uncontrolled activation of the coagulation system or defective inhibition of the activation processes may cause formation of local thrombi or embolisms in vessels (arteries, veins, lymph vessels) or in heart cavities. This may lead to serious disorders, such as myocardial infarction, angina pectoris (including unstable angina), reocclusions and restenoses after angioplasty or aortocoronary bypass, stroke, transitory ischemic attacks, peripheral arterial occlusive diseases, pulmonary embolisms or deep venous thromboses; hereinbelow, these disorders are collectively also referred to as thromboembolic disorders. In addition, in the case of consumption coagulopathy, hypercoagulability may—systemically—result in disseminated intravascular coagulation.

These thromboembolic disorders are the most frequent cause of morbidity and mortality in most industrialized countries (Pschyrembel, Klinisches Wörterbuch [clinical dictionary], $257^{th}$ edition, 1994, Walter de Gruyter Verlag, page 199 ff., entry "Blutgerinnung" [blood coagulation]; Römpp Lexikon Chemie, Version 1.5, 1998, Georg Thieme Verlag Stuttgart, entry "Blutgerinnung"; Lubert Stryer, Biochemie [biochemistry], Spektrum der Wissenschaft Verlagsgesellschaft mbH Heidelberg, 1990, page 259 ff.).

The anticoagulants, i.e. substances for inhibiting or preventing blood coagulation, which are known from the prior art have various, often grave disadvantages. Accordingly, in practice, an efficient treatment method or prophylaxis of thromboembolic disorders is very difficult and unsatisfactory.

In the therapy and prophylaxis of thromboembolic disorders, use is firstly made of heparin, which is administered parenterally or subcutaneously. Owing to more favourable pharmacokinetic properties, preference is nowadays more and more given to low-molecular-weight heparin; however, even with low-molecular-weight heparin, it is not possible to avoid the known disadvantages described below, which are involved in heparin therapy. Thus, heparin is ineffective when administered orally and has a relatively short half-life. Since heparin inhibits a plurality of factors of the blood coagulation cascade at the same time, the action is nonselective. Moreover, there is a high risk of bleeding; in particular, brain hemorrhages and gastrointestinal bleeding may occur, which may result in thrombopenia, drug-induced alopecia or osteoporosis (Pschyrembel, Klinisches Wörterbuch, $257^{th}$ edition, 1994, Walter de Gruyter Verlag, page 610, entry "Heparin"; Römpp Lexikon Chemie, Version 1.5, 1998, Georg Thieme Verlag Stuttgart, entry "Heparin").

A second class of anticoagulants are the vitamin K antagonists. These include, for example, 1,3-indanediones, and especially compounds such as warfarin, phenprocoumon, dicumarol and other coumarin derivatives which inhibit the synthesis of various products of certain vitamin K-dependent coagulation factors in the liver in a non-selective manner. Owing to the mechanism of action, however, the onset of the action is very slow (latency to the onset of action 36 to 48 hours). It is possible to administer the compounds orally; however, owing to the high risk of bleeding and the narrow therapeutic index, a time-consuming individual adjustment and monitoring of the patient are required. Moreover, further adverse effects, such as gastrointestinal disturbances, hair loss and skin necroses, have been described (Pschyrembel, Klinisches Wörterbuch, $257^{th}$ edition, 1994, Walter de Gruyter Verlag, page 292 ff., entry "coumarin derivatives"; Ullmann's Encyclopedia of Industrial Chemistry, $5^{th}$ edition, VCH Verlagsgesellschaft, Weinheim, 1985–1996, entry "vitamin K").

Recently, a novel therapeutic approach for the treatment and prophylaxis of thromboembolic disorders has been described. This novel therapeutic approach aims to inhibit factor Xa (cf. WO-A-99/37304; WO-A-99/06371; J. Hauptmann, J. Stürzebecher, Thrombosis Research 1999, 93, 203; F. Al-Obeidi, J. A. Ostrem, Factor Xa inhibitors by classical and combinatorial chemistry, DDT 1998, 3, 223; F. Al-Obeidi, J. A. Ostrem, Factor Xa inhibitors, Exp. Opin. Ther. Patents 1999, 9, 931; B. Kaiser, Thrombin and factor Xa inhibitors, Drugs of the Future 1998, 23, 423; A. Uzan, Antithrombotic agents, Emerging Drugs 1998, 3, 189; B.-Y. Zhu, R. M. Scarborough, Curr. Opin. Card. Puim. Ren. Inv. Drugs 1999, 1 (1), 63). It has been shown that, in animal models, various peptidic and nonpeptidic compounds are effective as factor Xa inhibitors.

Accordingly, it is an object of the present invention to provide novel substances for controlling disorders, which substances have a wide therapeutic spectrum.

In particular, they should be suitable for a more efficient prophylaxis and/or treatment of thromboembolic disorders, avoiding—at least to some extent—the disadvantages of the prior art described above, where the term "thromboembolic disorders" in the context of the present invention is to be understood as meaning, in particular, serious disorders, such as myocardial infarct, angina pectoris (including unstable angina), reocclusions and restenoses after angioplasty or aortocoronary bypass, stroke, transitory ischemic attacks, peripheral arterial occlusive diseases, pulmonary embolisms or deep venous thromboses.

It is another object of the present invention to provide novel anticoagulants which inhibit the blood coagulation factor Xa with increased selectivity, avoiding—at least to some extent—the problems of, the therapeutic methods for thromboembolic disorders known from the prior art.

The present invention provides compounds of the formula (I)

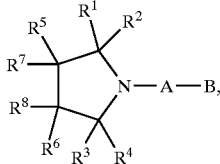

in which
R¹ and R² together represent O and
R³ and R⁴ together represent O,
or
R¹ represents hydrogen, hydroxy or $(C_1-C_4)$-alkoxy,
R² represents hydrogen and
R³ and R⁴ together represent O,
or
R¹ and R² together represent O,
R³ represents hydrogen, hydroxy or $(C_1-C_4)$-alkoxy and
R⁴ represents hydrogen,
R⁵ and R⁶ represent hydrogen and
R⁷ and R⁸ together represent

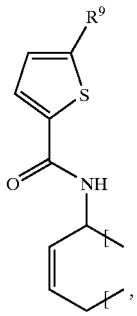

in which
R⁹ represents halogen, trifluoromethyl or methyl,
or
R⁵, R⁶, R⁷ and R⁸ together represent

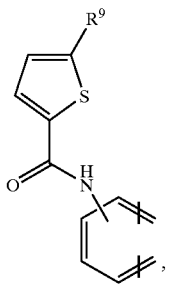

in which
R⁹ is as defined above,
A represents $(C_1-C_4)$-alkanediyl or $(C_2-C_4)$-alkenediyl,
B represents phenylene or cyclohexanediyl, which radicals may be substituted by amino, urea, sulfamoyl, —C(=N—NH—C(=NH)—NH₂)—H, —C(=NR¹⁰)—R¹¹,
in which
R¹⁰ represents hydrogen or —NH—C(=NH)—NH₂,
R¹¹ represents —NR¹²R¹³ or 5- to 10-membered heterocyclyl, in which
R¹² and R¹³, independently of one another, represent hydrogen, $(C_1-C_4)$-alkyl or $(C_3-C_7)$-cycloalkyl,
$(C_1-C_4)$-alkyl, which for its part may be substituted by cyano, $(C_1-C_4)$-alkoxycarbonyl, optionally $(C_1-C_4)$-alkyl-substituted 5- to 10-membered heterocyclyl, 5- to 10-membered heteroaryl, tri-$(C_1-C_4)$-alkylammonium, —NR¹⁴R¹⁵, —C(=NR¹⁶)—R¹⁷, —N—C(=O)—R¹⁸ or —N—C(=O)—NH—R¹⁹,
in which
R¹⁴ represents hydrogen, mono- or di-$(C_1-C_4)$-alkylamino, $(C_1-C_4)$-alkyl which is optionally substituted by 5- to 10-membered heteroaryl, represents 5- to 10-membered heterocyclyl, $(C_6-C_{10})$-aryl or 5- to 10-membered heteroaryl, where the rings for their part may be substituted by halogen,
R¹⁵ represents hydrogen or optionally cyano-substituted $(C_1-C_4)$-alkyl,
R¹⁶ represents hydrogen or hydroxy,
R¹⁷ represents amino, 5- to 10-membered heterocyclyl, optionally amino- or trifluoromethyl-substituted mono- or di-$(C_1-C_4)$-alkylamino, optionally trifluoromethyl-substituted $(C_3-C_7)$-cycloalkylamino,
R¹⁸ represents trifluoromethyl, $(C_1-C_4)$-alkyl, $(C_1-C_4)$-alkoxy or 5- to 10-membered heterocyclyl which is optionally substituted by $(C_1-C_4)$-alkyl,
R¹⁹ represents hydrogen, amino, dimethylamino, 5- to 10-membered heterocyclyl, 5- to 10-membered heteroaryl, or represents $(C_1-C_4)$-alkyl which is optionally substituted by $(C_1-C_4)$-alkoxycarbonyl, dimethylamino, carbamoyl or 5- to 10-membered heteroaryl,
$(C_1-C_4)$-alkoxy, which for its part may be mono- or disubstituted, independently of one another, by cyano, thiocarbamoyl, optionally $(C_1-C_4)$-alkyl-substituted 5- to 10-membered heterocyclyl, optionally halogen-substituted 5- to 10-membered heteroaryl, optionally —C(=NR²⁰)—R²¹-substituted $(C_6-C_{10})$-aryl or —C(=NR²⁰)—R²¹,
in which
R²⁰ represents hydrogen, hydroxy, $(C_3-C_7)$-cycloalkyl or optionally hydroxy-substituted $(C_1-C_4)$-alkyl,
R²¹ represents amino, $(C_1-C_4)$-alkylthio, $(C_3-C_7)$-cycloalkylamino, benzylamino or 5- to 10-membered heterocyclyl,
5- to 10-membered heterocyclyl which for its part may be substituted by $(C_1-C_4)$-alkyl,
$(C_6-C_{10})$-aryl which for its part may be mono- or disubstituted, independently of one another, by halogen, cyano, carbamoyl or optionally amino-substituted $(C_1-C_4)$-alkyl,
5- to 10-membered heteroaryloxy which for its part may be substituted by amino or N—$(C_1-C_4)$-alkylaminocarbonyl,
or 5- to 10-membered heteroaryl which for its part may be substituted by amino,
and their salts, hydrates, hydrates of the salts and solvates.

Depending on the substitution pattern, the compounds of the formula (I) according to the invention may exist in stereoisomeric forms which are either like image and mirror image (enantiomers) or not like image and mirror image (diastereomers). The invention relates to both the enantiomers or diastereomers and to their respective mixtures. The racemic forms, like the diastereomers, can be separated in a known manner into the stereoisomerically uniform components.

Furthermore, certain compounds of the formula (I) can be present in tautomeric form. This is known to the person skilled in the art, and such compounds are likewise within the scope of the invention.

Salts of the compounds according to the invention are physiologically acceptable salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, trifluoroacetic acid, propionic acid, maleic acid, fumaric acid, malic acid, citric acid, tartaric acid, lactic acid, benzoic acid, or methanesulfonic acid, ethanesulfonic acid, benzenesulfonic acid, toluenesulfonic acid or naphthalenedisulfonic acid.

Other possible salts are physiologically acceptable salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine or methyl-piperidine.

Moreover, the invention also embraces prodrugs of the compounds according to the invention. According to the invention, prodrugs are forms of the compounds of the formula (I) which for their part can be biologically active or inactive, but which can be converted into the corresponding biologically active form under physiological conditions (for example metabolically or solvolytically).

According to the invention, "hydrates" or "solvates" are forms of the compounds of the formula (I) which, in solid or liquid state, form a molecule compound or a complex by hydration with water or coordination with solvent molecules. Examples of hydrates are sesquihydrates, monohydrates, dihydrates or trihydrates. Equally suitable are the hydrates or solvates of salts of the compounds according to the invention.

Halogen represents fluorine, chlorine, bromine and iodine. Preference is given to chlorine, bromine or fluorine.

($C_1$–$C_4$)-Alkyl represents a straight-chain or branched alkyl radical having 1 to 4 carbon atoms. Examples which may be mentioned are: methyl, ethyl, n-propyl, isopropyl, n-butyl, isobutyl and tert-butyl. The corresponding alkyl groups having fewer carbon atoms, such as, for example ($C_1$–$C_3$)-alkyl, are derived analogously from this definition. In general, preference is given to ($C_1$–$C_3$)-alkyl.

The meaning of the corresponding component of other more complex substituents, such as, for example, in mono- or dialkylamino, trialkammonium or N-alkylaminocarbonyl, is likewise derived from this definition.

Monoalkylamino represents an amino group having an alkyl substituent as defined above. Dialkylamino represents an amino group having two identical or different alkyl substituents as defined above. Trialkylammonium represents an amino group having three identical or different alkyl substituents as defined above. N-Alkylaminocarbonyl represents an amino group which has an alkyl radical as defined above and is attached via a carbonyl group.

($C_1$–$C_4$)-Alkanediyl represents a straight-chain or branched alkanediyl radical having 1 to 4 carbon atoms. Preference is given to a straight-chain or branched alkanediyl radical having 1 to 3 carbon atoms. Examples which may be mentioned are: methanediyl, ethanediyl, propane-1,3-diyl, propane-1,2-diyl, propane-2,2-diyl, butane-1,4-diyl, butane-1,3-diyl.

($C_2$–$C_4$)-Alkenediyl represents a straight-chain or branched alkenediyl radical having 2 to 4 carbon atoms, preferably 2 to 3 carbon atoms. Examples which may be mentioned are: ethene-1,2-diyl, ethene-1,1-diyl, propene-1,1-diyl, propene-1,2-diyl, propene-1,3-diyl, propene-3,3-diyl, propene-2,3-diyl, but-2-ene-1,4-diyl.

($C_3$–$C_7$)-Cycloalkyl represents a cyclic alkyl radical having 3 to 7 carbon atoms. Examples which may be mentioned are: cyclopropyl, cyclobutyl, cyclopentyl, cyclohexyl or cycloheptyl. The corresponding cycloalkyl radicals having fewer carbon atoms, such as ($C_3$–$C_6$)-cycloalkyl, are derived from this definition. Preference is given to cyclopropyl, cyclopentyl and cyclohexyl.

The meaning of the corresponding component of other more complex substituents, such as, for example, cycloalkylamino, is likewise derived from this definition. Cycloalkylamino represents a cycloalkyl radical as defined above which is attached via an amino group.

($C_1$–$C_4$)-Alkoxy represents a straight-chain or branched alkoxy radical having 1 to 4 carbon atoms. Examples which may be mentioned are: methoxy, ethoxy, n-propoxy, isopropoxy, n-butoxy, isobutoxy, tert-butoxy. The corresponding alkoxy groups having fewer carbon atoms, such as, for example, ($C_1$–$C_3$)-alkoxy, are derived analogously from this definition. In general, preference is given to ($C_1$–$C_3$)-alkoxy.

($C_1$–$C_4$)-Alkoxycarbonyl represents a straight-chain or branched alkoxy radical having 1 to 4 carbon atoms which is attached via a carbonyl group. Examples which may be mentioned are: methoxycarbonyl, ethoxycarbonyl, n-propoxycarbonyl, isopropoxycarbonyl and t-butoxycarbonyl. Preference is given to an alkoxycarbonyl radical having 1 or 2 carbon atoms.

($C_6$–$C_{10}$)-Aryl represents an aromatic radical having 6 to 10 carbon atoms. Examples which may be mentioned are: phenyl and naphthyl. In general, preference is given to phenyl.

5- to 10-membered heteroargl represents a mono- or bicyclic, optionally benzo-fused aromatic heterocycle (heteroaromatic) which has up to 3 heteroatoms from the group consisting of N, O and S and which is attached via a ring carbon atom or a ring nitrogen atom of the heteroaromatic. Examples which may be mentioned are: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl. The corresponding heteroaromatics having a smaller ring size, such as, for example, 5- or 6-membered heteroaryl, are derived analogously from this definition. In general, preference is given to 5- or 6-membered heteroaryl, such as, for example, pyridyl, pyrimidyl, pyridazinyl and pyrazolyl.

The meaning of the corresponding component of other more complex substituents, such as, for example, heteroaryloxy, is likewise derived from this definition. Heteroaryloxy represents a heteroaryl radical as defined above which is attached via an oxygen atom.

5- to 10-membered heterocyclyl represents a saturated or partially unsaturated mono- or bicyclic, optionally benzo-fused heterocycle which has up to 3 heteroatoms from the group consisting of S, N and O and which is attached via a ring carbon atom or a ring nitrogen atom. Examples which may be mentioned are: tetrahydrofuryl, pyrrolidinyl, pyrrolinyl, piperidinyl, 1,2-dihydropyridinyl, 1,4-dihydropyridinyl, piperazinyl, morpholinyl, morpholinyl N-oxide, thiomorpholinyl, azepinyl, imidazolinyl, tetrahydropyrimidinyl and 1,4-diazepinyl. The corresponding heterocycles having a smaller ring size, such as, for example, 5- or 6-membered heterocycles, are derived analogously from this definition. In general, preference is given to 5- or 6-membered heterocycles, such as piperidinyl, morpholinyl, piperazinyl, imidazolinyl, tetrahydropyrimidinyl and pyrrolidinyl.

Preference is given to compounds of the formula (I),
in which
$R^1$ and $R^2$ together represent O and
$R^3$ and $R^4$ together represent O,
or
$R^1$ represents hydrogen, hydroxy, methoxy or ethoxy,
$R^2$ represents hydrogen and
$R^3$ and $R^4$ together represent O,
or
$R^1$ and $R^2$ together represent O,
$R^3$ represents hydrogen, hydroxy, methoxy or ethoxy and
$R^4$ represents hydrogen,
$R^5$ and $R^6$ represent hydrogen and
$R^7$ and $R^8$ together represent

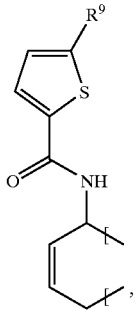

in which
$R^9$ represents halogen or trifluoromethyl,
or
$R^5$, $R^6$, $R^7$ and $R^8$ together represent

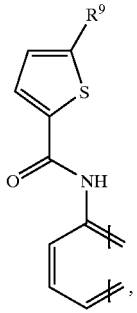

in which
$R^9$ is as defined above,
A represents $(C_1-C_3)$-alkanediyl or $(C_2-C_3)$-alkenediyl,
B represents phenylene or cyclohexanediyl, which radicals may be substituted by —C(=NR$^{10}$)—R$^{11}$
in which
$R^{10}$ represents hydrogen,
$R^{11}$ represents —NR$^{12}$R$^{13}$ or 5- to 10-membered heterocyclyl,
in which
$R^{12}$ and $R^{13}$, independently of one another, represent hydrogen, $(C_1-C_4)$-alkyl or $(C_3-C_7)$-cycloalkyl,
methyl or ethyl which for their part may be substitued by cyano, methoxycarbonyl, optionally methyl- or ethyl-substituted 5- or 6-membered heterocyclyl, 5- or 6-membered heteroaryl, tri-$(C_1-C_2)$-alkylammonium, —NR$^{14}$R$^{15}$, —C(=NR$^{16}$)—R$^{17}$, —N—C(=O)—R$^{18}$ or —N—C(=O)—NH—R$^{19}$,
in which
$R^{14}$ represents hydrogen, dimethylamino, methyl or ethyl, which radicals are optionally substituted by 5- or 6-membered heteroaryl, represents 5- or 6-membered heterocyclyl or 5- or 6-membered heteroaryl, which may be substituted by halogen,
$R^{15}$ represents hydrogen, methyl or ethyl,
$R^{16}$ represents hydrogen,
$R^{17}$ represents amino, 5- or 6-membered heterocyclyl, optionally amino- or trifluoromethyl-substituted mono- or di-$(C_1-C_4)$-alkylamino, optionally trifluoromethyl-substituted $(C_3-C_7)$-cycloalkylamino,
$R^{18}$ represents trifluoromethyl or $(C_1-C_4)$-alkyl,
$R^{19}$ represents hydrogen, amino or optionally methoxy- or ethoxycarbonyl-substituted $(C_1-C_4)$-alkyl,
methoxy or ethoxy which for their part may be mono- or disubstituted, independently of one another, by optionally methyl-substituted 5- or 6-membered heterocyclyl or —C(=NR$^{20}$)—R$^{21}$,
in which
$R^{20}$ represents hydrogen,
$R^{21}$ represents amino, $(C_3-C_6)$-cycloalkylamino, benzylamino or 5- or 6-membered heterocyclyl, or pyridyl, and their salts, hydrates, hydrates of the salts and solvates.

Particular preference is given to compounds of the formula (I)
in which
$R^1$ and $R^2$ together represent O and
$R^3$ and $R^4$ together represent O, or
$R^1$ represents hydrogen, hydroxy or methoxy,
$R^2$ represents hydrogen and
$R^3$ and $R^4$ together represent O, or
$R^1$ and $R^2$ together represent O,
$R^3$ represents hydrogen, hydroxy or methoxy and
$R^4$ represents hydrogen,
$R^5$ and $R^6$ represent hydrogen and
$R^7$ and $R^8$ together represent

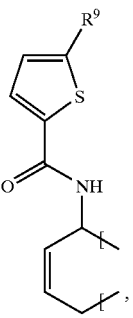

in which

R⁹ represents chlorine or bromine, or

R⁵, R⁶, R⁷ and R⁸ together represent

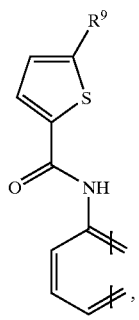

in which

R⁹ is as defined above,

A represents methanediyl or ethanediyl,

B represents phenylene which may be substituted by —C(=NR¹⁰)—R¹¹ in which

R¹⁰ represents hydrogen,

R¹¹ represents amino, methyl which for its part may be substituted by cyano, optionally methyl-substituted imidazolinyl or tetrahydropyrimidinyl, —NR¹⁴R¹⁵ or —C(=NR¹⁶)—R¹⁷, in which R¹⁴ represents optionally pyridyl-substituted methyl or pyridyl, R¹⁵ represents hydrogen, R¹⁶ represents hydrogen, R¹⁷ represents amino, piperidinyl, morpholinyl, pyrrolidinyl, optionally amino- or trifluoromethyl-substituted mono- or di-(C₁–C₃)-alkylamino or optionally trifluoromethyl-substituted cyclopropyl-, cyclopentyl- or cyclohexylamino, or methoxy or ethoxy which for their part may be substituted by —C(=NH)—NH₂, and their salts, hydrates, hydrates of the salts and solvates.

Particular preference is also given to compounds of the formula (I) in which B represents phenylene or cyclohexanediyl whose substituents are located in the 3- or 4-position relative to the point of attachment of the phenyl or cyclohexane ring.

The general or preferred radical definitions or illustrations listed above can be combined with one another as desired, i.e. including combinations between the respective ranges and preferred ranges. They apply both to the end products and, correspondingly, to the precursors and intermediates.

The present invention also provides a process for preparing the compounds of the formula (I) according to the invention where either

[A] compounds of the formula (II) or (IIa)

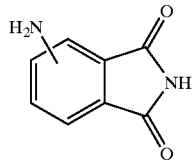

(II)

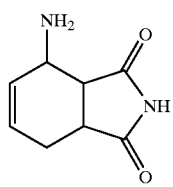

(IIa)

are, using compounds of the formula (III)

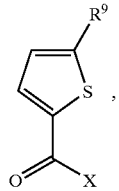

(III)

in which R⁹ is as defined above and X represents a leaving group, converted into compounds of the formula (IV)

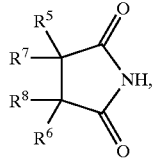

(IV)

in which R⁵, R⁶, R⁷ and R⁸ are as defined above and then reacted with compounds of the formula (V)

Y-A-B     (V), in which A and B are as defined above and Y represents a suitable leaving group, to give compounds of the formula (I)

in which both R¹ and R² and R³ and R⁴, in each case together, represent O and R⁵, R⁶, R⁷, R⁸, A and B are as defined above, or

[B] compounds of the formula (VI) or (VIa)

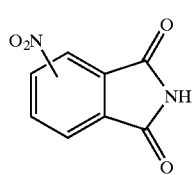

(VI)

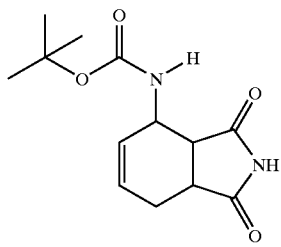

are reacted with compounds of the formula (V), to give compounds of the formula (VII) or (VIIa)

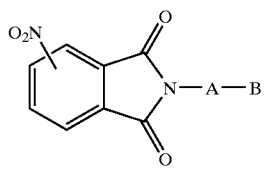

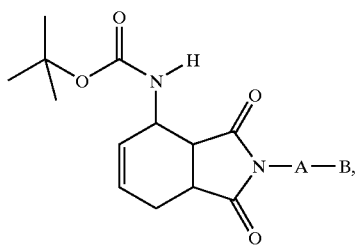

in which A and B are as defined above and then either

[B1] compounds of the formula (VIII) are converted by reduction of the nitro group into compounds of the formula (VIII), or compounds of the formula (VIIa) are converted by removal of the BOC protective group into compounds of the formula (VIIIa)

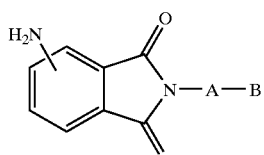

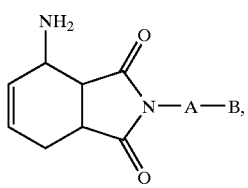

in which A and B are as defined above
and then reacted with compounds of the formula (III), to give compounds of the formula (I)
in which both $R^1$ and $R^2$ and $R^3$ and $R^4$, in each case together, represent O and $R^5$, $R^6$, $R^7$, $R^8$, A and B are as defined above, or

[B2] compounds of the formula (VII) are, by reduction of a carbonyl group and the nitro group, converted into compounds of the formula (IX)

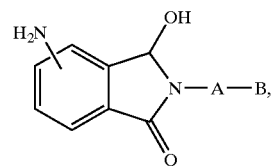

in which A and B are as defined above,
subsequently, if appropriate, converted by further reduction into compounds of the formula (X)

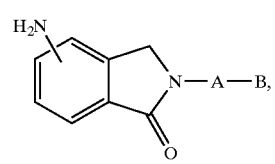

in which A and B are as defined above,
and the resulting compounds of the formula (IX) or (X) are reacted with compounds of the formula (III), to give compounds of the formula (I)
in which $R^1$ and $R^2$ together represent O, $R^3$ represents hydrogen or hydroxy, $R^4$ represents hydrogen or $R^3$ and $R^4$ together represent O, $R^1$ represents hydrogen or hydroxy, $R^2$ represents hydrogen and $R^5$, $R^6$, $R^7$, $R^8$, A and B are as defined above, or

[C] compounds of the formula (XI)

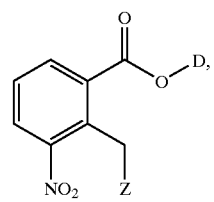

in which D represents $(C_1–C_4)$-alkyl and Z represents a leaving group are reacted with compounds of the formula (XII)

$$H_2N\text{-}A\text{-}B \quad (XII),$$

in which A and B are as defined above,
to give compounds of the formula (XIII)

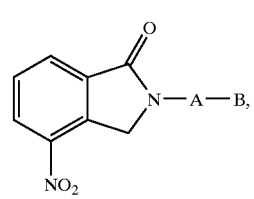

in which A and B are as defined above,
then, by reduction of the nitro group, converted into compounds of the formula (XIV)

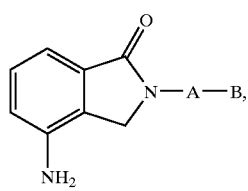

(XIV)

in which A and B are as defined above and then reacted with compounds of the formula (III), to give compounds of the formula (I)

in which $R^1$ and $R^2$ represent hydrogen, $R^3$ and $R^4$ together represent O and $R^5$, $R^6$, $R^7$, $R^8$, A and B are as defined above, where the resulting compounds of the formula (I) may, if appropriate, subsequently be subjected to further derivatization which can be carried out by customary methods.

The process according to the invention can be illustrated in an exemplary manner by the formula scheme below:

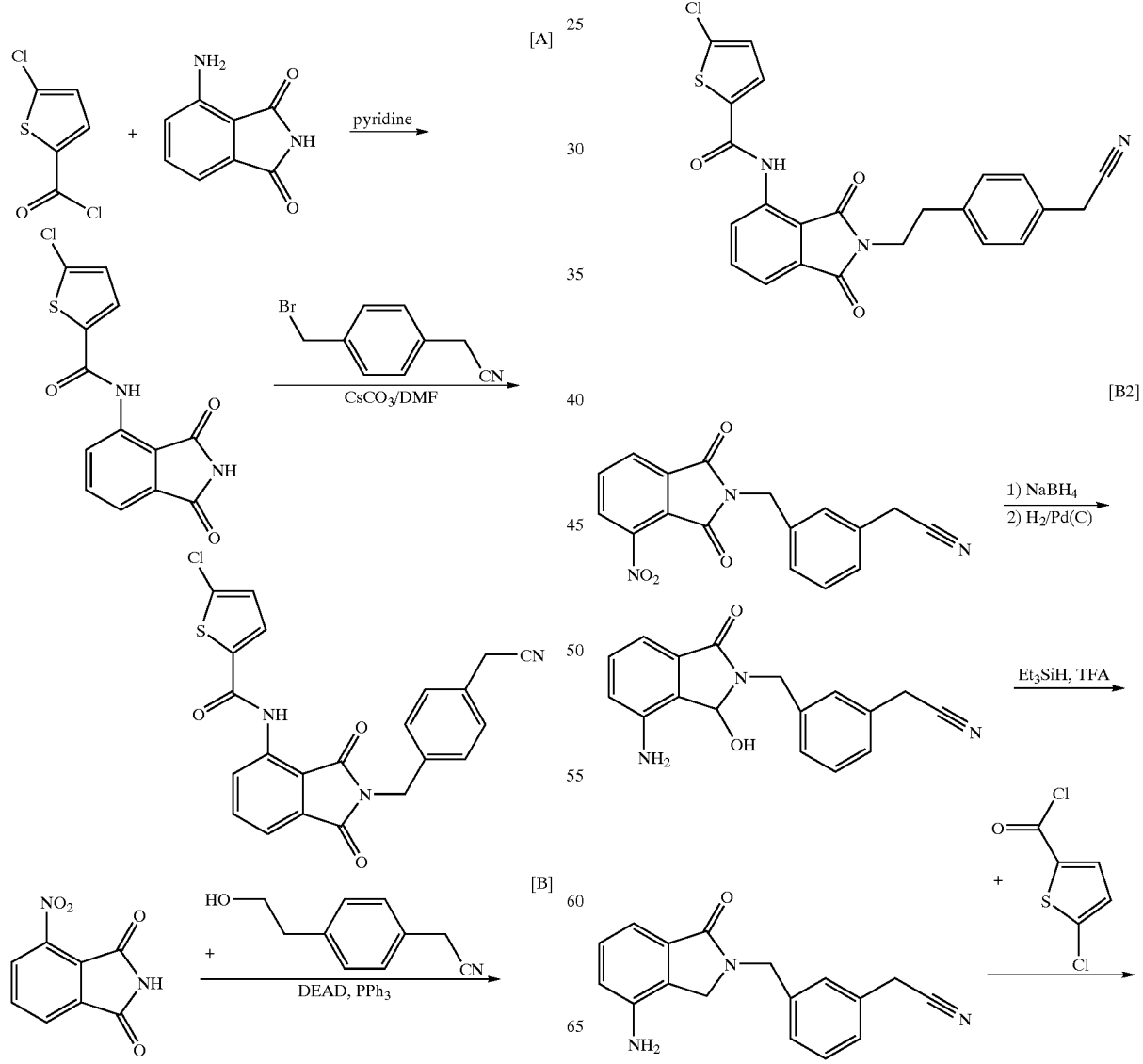

-continued

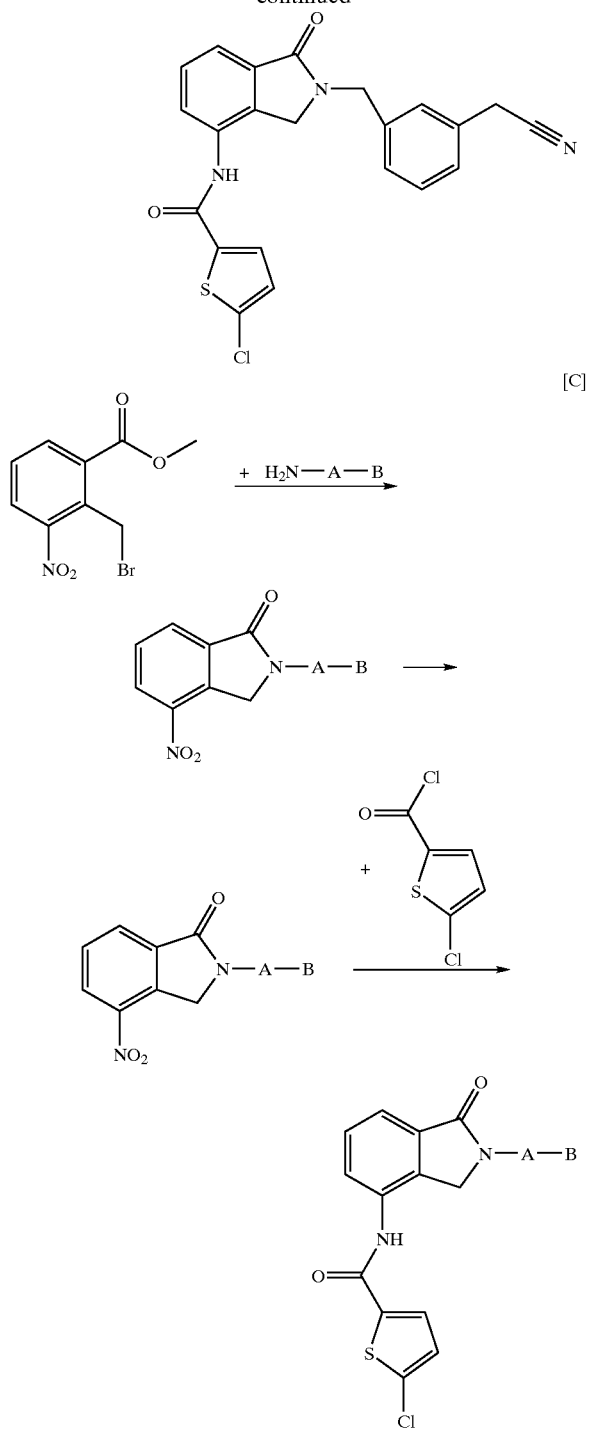

[C]

Solvents suitable for the process according to the invention are all organic solvents which are inert under the reaction conditions, or water. These include alcohols, such as methanol, ethanol and isopropanol, ketones, such as acetone and methyl ethyl ketone, acyclic and cyclic ethers, such as diethyl ether, tetrahydrofuran and dioxane, esters, such as ethyl acetate or butyl acetate, hydrocarbons, such as benzene, xylene, toluene, hexane or cyclohexane, dimethylformamide, acetonitrile, pyridine, dimethyl sulfoxide (DMSO), chlorinated hydrocarbons, such as dichloromethane, chlorobenzene or dichloroethane. It is also possible to use mixtures of the solvents mentioned above.

Suitable bases are the customary inorganic or organic bases. These preferably include alkali metal hydroxides, such as, for example, sodium hydroxide or potassium hydroxide, or alkali metal carbonates, such as sodium carbonate or potassium carbonate or sodium bicarbonate or potassium bicarbonate, or sodium methoxide or potassium methoxide or sodium ethoxide or potassium ethoxide or potassium tert-butoxide, or else amides, such as sodium amide, lithium bis(trimethylsilyl)amide or lithium diisopropylamide, or organometallic compounds, such as butyllithium or phenyllithium, or else also amines, such as trialkylamines, for example triethylamine, N-methylmorpholine (NMM), N-methylpiperidine, diisopropylethylamine (Hünig base) or 4-N,N-dimethylaminopyridine (DMAP) or pyridine.

The process according to the invention can be carried out under atmospheric, elevated or reduced pressure (for example in the range from 0.5 to 5 bar). In general, the process is carried out at atmospheric pressure.

The reaction with thiophenecarboxylic acid derivatives of the formula (III), such as in the first process step [A]: (II)/(IIa)+(III)→(IV); the second process step [B1]: (VIII)/(VIIIa)+(III)→(I); the third process step [B2]: (IX)/(X)+(III)→(I) and the third process step [C]: (XIV)+(III)→(I), is generally carried out in a temperature range from −78° C. to +120° C., preferably in the range from −78° C. to +60° C., in particular at from 0° C. to +50° C. The leaving group X used is, for example, a halide, i.e. the corresponding acid chloride or bromide, or use is made of corresponding acid anhydrides. Preference is given to the corresponding acid chloride. The preferred solvent is pyridine or tetrahydrofuran. If appropriate, 4-dimethylaminopyridine (4-DMAP) or triethylamine is added as base.

In the second process step [A]: (IV)+(V)→(I) and in the first process step [B]: (VI)/(VIa)+(V)→(VII)/(VIIa), phthalimides are derivatized in a nucleophilic substitution reaction with compounds of the formula (V). Suitable leaving groups Y in compounds of the formula (V) are, for example, halogen, tosylate, mesylate or a hydroxyl function activated by reagents such as diethyl azodicarboxylate (DEAD)/PPh$_3$ (Mitsunobu reaction). In the case of a reaction under Mitsunobu conditions, the preferred solvent is tetrahydrofuran; the reaction with alkyl halides is preferably carried out in the solvent dimethylformamide in the presence of a base, such as, for example, potassium carbonate. The reaction is generally carried out in a temperature range of from −78° C. to +120° C., preferably at from 0° C. to room temperature.

In the first process step [B1]: (VII)→(VIII), in the second part of the first process step [B2]: (VII)→(IX) and in the second process step [C]: (XIII)→(XIV), an aromatic nitro group is converted into the corresponding amine. Preferred solvents are methanol, ethanol, tetrahydrofuran and ethyl acetate, or mixtures of these solvents. The reaction is generally carried out in a temperature range of from −78° C. to +120° C., preferably at room temperature. Suitable hydrogenation processes are customary hydrogenation processes; preference is given to the hydrogenation with hydrogen at atmospheric pressure in the presence of a catalyst, such as, for example, palladium-on-carbon [Pd(C); 10% by weight].

In the first process step [B1]: (VIIa)→(VIIIa), the amino group is liberated by removing the BOC protective group under reaction conditions customary for this purpose in the presence of an acid. Preferred solvent/acid systems are dichloromethane/trifluoroacetic acid or dioxane/hydrochloric acid. The reaction is generally carried out in a temperature range of from −78° C. to +120° C., preferably at from 0° C. to room temperature.

In the first part of the first process step [B2]: (VII)→(IX), a carbonyl function of the phthalimide system is reduced to the corresponding hydroxyl function. In general, an isomer mixture is formed which can be separated chromatographically. The preferred solvent is a mixture of methanol and dichloromethane. Suitable hydrogenation processes are customary hydrogenation processes; preference is given to using the reducing agent sodium borohydride.

In the second process step [B2]: (IX)→(X), which is carried out, if appropriate, a hydroxyl group is converted by reduction into the corresponding hydrocarbon. The reaction is generally carried out in a temperature range of from −78° C. to +120° C., preferably at room temperature. The preferred solvent is dichloromethane. Suitable hydrogenation processes are customary hydrogenation processes, preferably the system trifluoroacetic acid (TFA)/triethylsilane.

The alkylation in the first process step [C]: (XI)+(XII)→(XIII) is generally carried out in a temperature range of from −78° C. to +120° C., preferably at from +50° C. to +80° C. Suitable leaving groups Z in compounds of the formula (XI) are, for example: halogen, tosylate or mesylate, preference is given to bromine. The preferred solvent is dimethylformamide, an additional base is, for example, triethylamine.

The compounds of the formulae (II), (IIa), (III), (V), (VI), (VIa), (XI) and (XII) are commercially available, known from the literature or can be prepared by customary methods known from the literature.

The compounds of the formula (I) according to the invention have an unforeseeable useful pharmacological activity spectrum and are therefore particularly suitable for the prophylaxis and/or treatment of disorders.

The compounds of the formula (I) according to the invention are also suitable in combination with one or more other active compounds for the prophylaxis and/or treatment of disorders. Suitable active compounds for combinations are, in particular, platelet aggregation inhibitors, anticoagulants, fibrinolytics, antilipemics, coronary therapeutics and/or vasodilators.

The compounds of the formula (I) according to the invention act in particular as anticoagulants and can therefore preferably be employed in medicaments for the prophylaxis and/or treatment of thromboembolic disorders. For the purpose of the present invention, "thromboembolic disorders" include, in particular, serious disorders such as myocardial infarct, angina pectoris (including unstable angina), reocclusions and restenoses after angioplasty or aortocoronary bypass, stroke, transitory ischemic attacks, peripheral arterial occlusive diseases, pulmonary embolisms or deep venous thromboses.

Furthermore, the compounds of the formula (I) according to the invention are also suitable for treating disseminated intravascular coagulation (DIC).

Finally, the compounds of the formula (I) according to the invention are also suitable for the prophylaxis and/or treatment of atherosclerosis and arthritis, and additionally also for the prophylaxis and/or treatment of Alzheimer's disease and cancer.

Furthermore, the present invention also includes a method for preventing the coagulation of blood in vitro, in particular in the case of banked blood or biological samples containing factor Xa, which method is characterized in that compounds of the formula (I) are added.

The compounds of the formula (I) according to the invention act in particular as selective inhibitors of the blood coagulation factor Xa and do not inhibit, or only inhibit at considerably higher concentrations, other serine proteases as well, such as thrombin, plasmin or trypsin.

In the context of the present invention, inhibitors of the blood coagulation factor Xa in which the $IC_{50}$ values for the factor Xa inhibition are lower by a factor of 100, preferably by a factor of 500, in particular by a factor of 1000, than the $IC_{50}$ values for the inhibition of other serine proteases, in particular thrombin, plasmin and trypsin, are referred to as being "selective", where with a view to the test methods for selectivity, reference is made to the test methods of Examples A-1) a.1) and a.2) described below.

All customary administration forms are suitable for administration of the compounds according to the invention. Administration is preferably carried out orally, lingually, sublingually, buccally, rectally, locally, such as, for example, with implants or stents or parenterally (i.e. bypassing the intestinal tract, that is to say intravenously, intraarterially, intracardially, intracutaneously, subcutaneously, transdermally, intraperitoneally or intramuscularly). Particularly suitable are oral and intravenous administration. Very particular preference is given to oral administration, this being a further advantage with respect to the prior-art therapy of thromboembolic disorders.

The novel active compounds of the formula (I) can be converted in a known manner into the customary formulations, such as tablets, sugar-coated tablets, pills, granules, aerosols, syrups, emulsions, suspensions and solutions, using inert non-toxic pharmaceutically suitable excipients or solvents. Here, the therapeutically active compound should in each case be present in a concentration of from about 0.1 to 95% by weight, preferably from 0.5 to 90% by weight, in particular from 1 to 85% by weight, of the total mixture, i.e. in amounts which are sufficient in order to achieve the dosage range indicated.

In spite of this, if appropriate, it may be necessary to depart from the amounts mentioned above, namely depending on the body weight or on the type of administration route, on the individual response to the medicament, on the manner of its formulation and the time or interval at which administration takes place. Thus, in some cases, it may be adequate to manage with less than the abovementioned minimum amount, while in other cases the upper limit mentioned must be exceeded. In the case of the administration of relatively large amounts, it may be advisable to divide these into several individual administrations over the course of the day.

The formulations are prepared, for example, by extending the active compounds with solvents and/or excipients, if appropriate using emulsifiers and/or dispersants, it being possible, for example, if the diluent used is water, optionally to use organic solvents as auxiliary solvents.

In general it has proved advantageous in the case of intravenous administration to administer amounts from approximately 0.001 to 10 mg/kg, preferably approximately 0.01 to 10 mg/kg, in particular approximately 0.1 to 8 mg/kg, of body weight to achieve effective results.

In general, it has proved advantageous in the case of oral administration to administer amounts from approximately 0.01 to 50 mg/kg, preferably approximately 0.1 to 10 mg/kg, in particular approximately 0.5 to 8 mg/kg, of body weight to achieve effective results.

In spite of this, if appropriate, it may be necessary in the case of intravenous or oral administration to depart from the amounts mentioned above, namely depending on the body weight or on the type of administration route, on the individual response to the medicament, on the manner of its formulation and the time or interval at which administration takes place. Thus, in some cases, it may be adequate to manage with less than the abovementioned minimum amount, while in other cases the upper limit mentioned must be exceeded. In the case of the administration of relatively large amounts, it may be advisable to divide these over the course of the day, namely into several individual doses or as a continuous infusion.

Compared to the conventional preparations for treating thromboembolic disorders, the compounds of the formula (I) according to the invention are distinguished in particular by the fact that a greater therapeutic range is achieved by the selective inhibition of factor Xa. For the patient, this means a lower risk of bleeding, and for the treating physician, this means that the patient is easier to adjust. Moreover—owing to the mechanism—the onset of action is more rapid. Above all, however, the compounds according to the invention permit an oral administration form, which is a further advantage of the therapy with the compounds according to the invention.

The present invention is illustrated by the examples below.

A Evaluation of the Physiological Activity

1. General Test Methods

The particularly advantageous biological properties of the compounds according to the invention can be determined by the following methods.

a) Test Description (In Vitro)

a.1) Determination of the Factor Xa Inhibition

The enzymatic activity of human factor Xa (FXa) was measured using the conversion of a chromogenic substrate specific for FXa. Factor Xa cleaves p-nitroaniline from the chromogenic substrate. The determinations were carried out in microtiter plates as follows.

The test substances, in various concentrations, were dissolved in DMSO and incubated at 25° C. with human FXa (0.5 mmol/l dissolved in 50 mmol/l of tris buffer [C,C,C-tris(hydroxymethyl)-aminomethane], 150 mmol/l of NaCl, 0.1% BSA (bovine serum albumin), pH=8.3) for 10 minutes. Pure DMSO was used as control. The chromogenic substrate (150 μmol/l of Pefachrome® FXa from Pentapharm) was then added. After an incubation time of 20 minutes at 25° C., the extinction at 405 nm was determined. The extinctions of the test mixtures containing test substance were compared with the control mixtures without test substance, and the $IC_{50}$ values were calculated from these data.

a.2) Determination of the Selectivity

To assess selective FXa inhibition, the test substances were examined for their inhibition of other human serine proteases such as thrombin, trypsin and plasmin. To determine the enzymatic activity of thrombin (75 mU/ml), trypsin (500 mU/ml) and plasmin (3.2 nmol/l), these enzymes were dissolved in tris buffer (100 mmol/l, 20 mmol/l $CaCl_2$, pH=8.0) and incubated with test substance or solvent for 10 minutes. The enzymatic reaction was then started by adding the corresponding specific chromogenic substrates (Chromozym Thrombin® from Boehringer Mannheim, Chromozym Trypsin® from Boehringer Mannheim, Chromozym Plasmin® from Boehringer Mannheim) and the extinction at 405 nm was determined after 20 minutes. All determinations were carried out at 37° C. The extinctions of the test mixtures containing test substance were compared with the control samples without test substance, and the $IC_{50}$ values were calculated from these data.

a.3) Determination of the Anticoagulant Action

The anticoagulant action of the test substances was determined in vitro in human plasma. To this end, human blood was drawn off in a mixing ratio of sodium citrate/blood of 1/9 using a 0.11 molar sodium citrate solution as receiver. Immediately after the blood had been drawn off, it was mixed thoroughly and centrifuged at about 2000 g for 10 minutes. The supernatant was pipetted off. The prothrombin time (PT, synonyms: thromboplastin time, quick test) was determined in the presence of varying concentrations of test substance or the corresponding solvent using a commercial test kit (Neoplastin® from Boehringer Mannheim). The test compounds were incubated with the plasma at 37° C. for 10 minutes. Coagulation was then started by addition of thromboplastin, and the time when coagulation occurred was determined. The concentration of test substance which effected a doubling of the prothrombin time was determined.

b) Determination of the Antithrombotic Activity (In Vivo)

b.1) Arteriovenous Shunt Model (Rat)

Fasting male rats (strain: HSD CPB:WU) having a weight of 200–250 g were anaesthetized using a Rompun/Ketavet solution (12 mg/kg/50 mg/kg). Thrombus formation was initiated in an arteriovenous shunt in accordance with the method described by Christopher N. Berry et al., Br. J. Pharmacol. (1994), 113, 1209–1214. To this end, the left jugular vein and the right carotid artery were exposed. The two vessels were connected by an extracorporeal shunt using a polyethylene tube (PE 60) of a length of 10 cm. In the middle, this polyethylene tube was attached to a further polyethylene tube (PE 160) of a length of 3 cm which contained a roughened nylon thread which had been arranged to form a loop, to form a thrombogenic surface. The extracorporeal circulation was maintained for 15 minutes. The shunt was then removed and the nylon thread with the thrombus was weighed immediately. The weight of the nylon thread on its own had been determined before the experiment was started. Before the extracorporeal circulation was set up, the test substances were administered to the animals while awake either intravenously via the tail vein or orally using a pharyngeal tube.

b.2) Arterial Thrombosis Model (Rat)

Male fasting rats (strain: HSD CPB: WU) were anaesthetized as described above. On average, the rats had a weight of about 200 g. The left carotid artery was exposed (about 2 cm). The formation of an arterial thrombus was induced by mechanical injury to the blood vessel in accordance with the method described by K. Meng et al., Naunyn-Schmiedeberg's Arch. Pharmacol. (1977), 301, 115–119. To this end, the exposed carotid artery was clamped from the blood flow, cooled to −12° C. in a metal trough for 2 minutes and, to standardize the size of the thrombi, simultaneously compressed using a weight of 200 g. The blood flow was then additionally reduced by a clip which was placed around the carotid artery distally from the injured section of the vessel. The proximal clamp was removed, and the wound was closed and re-opened after 4 hours to remove the injured section of the vessel. The section of the vessel was opened longitudinally and the thrombus was removed from the injured section of the vessel. The moist weight of the thrombi was determined immediately. The test substances were administered to the animals while awake at the beginning of the experiment, either intravenously via the tail vein or orally using a pharyngeal tube.

b.3) Venous Thrombosis Model (Rat)

Male fasting rats (strain: HSD CPB: WU) were anaesthetized as described above. On average, the rats had a weight of about 200 g. The left jugular vein was exposed (about 2 cm). The formation of a venous thrombus was induced by mechanical injury to the blood vessel in accordance with the method described by K. Meng et al., Naunyn-Schmiedeberg's Arch. Pharmacol. (1977), 301, 115–119. To this end, the jugular vein was clamped from the blood flow, cooled to −12° C. in a metal trough for 2 minutes and, to standardize the size of the thrombi, simultaneously compressed using a weight of 200 g. The blood flow was re-opened and the wound was closed. After 4 hours, the wound was re-opened to remove the thrombi from the injured sections of the vessel. The moist weight of the thrombi was determined immediately. The test substances were administered to the animals while awake at the beginning of the experiment, either intravenously via the tail vein or orally using a pharyngeal tube.

B Preparation Examples

The following abbreviations are used in the examples:

DMF=Dimethylformamide
THF=Tetrahydrofuran

HPLC Parameter:

Method 1: Column: Kromasil C18; L-R temperature: 30° C.; Flow rate=0.75 mlmin$^{-1}$; mobile phase: A=0.01 M HClO$_4$, B=CH$_3$CN, gradient:→0.5 min 98% A, →4.5 min 10% A, →6.5 min 10% A.

Method 2: Column: Kromasil C18 60*2; L-R temperature: 30° C.; Flow rate=0.75 mlmin$^{-1}$; mobile phase: A=0.01 M H$_3$PO$_4$, B=CH$_3$CN, gradient:→0.5 min 90% A, →4.5 min 10% A, →6.5 min 10% A.

Method 3: Column: Kromasil C18 60*2; L-R temperature: 30° C.; Flow rate=0.75 mlmin$^{-1}$; mobile phase: A=0.005 M HClO$_4$, B=CH$_3$CN, gradient:→0.5 min 98% A, →4.5 min 10% A, →6.5 min 10% A.

Method 4: Column: Symmetry C18, 2.1 mm×150 mm; column oven: 50° C.; Flow rate=0.6 mlmin$^{-1}$; mobile phase: A=0.6 g 30% strength HCl/l water, B=CH$_3$CN, gradient: 0.0 min 90% A, →4.0 min 10% A, →9 min 10% A.

Method 5: Instrument Micromass Quattro LCZ

Column Symmetry C18, 50 mm×2.1 mm, 3.5 µm; temperature: 40° C.; Flow rate=0.5 mlmin$^{-1}$; mobile phase A=CH$_3$CN+0.1% formic acid, mobile phase B=water+0.1% formic acid. gradient: 0.0 min 10% A, →4 min 90% A, →6 min 90% A.

Method 6: Instrument Micromass Platform LCZ

Column: Symmetry C18, 50 mm×2.1 mm, 3.5 µm; temperature: 40° C.; Flow rate=0.5 mlmin$^{-1}$; mobile phase A=CH$_3$CN+0.1% formic acid, mobile phase B=water+0.1% formic acid, gradient: 0.0 min 10% A, →4 min 90% A, →6 min 90% A.

Method 7: Instrument Micromass Quattro LCZ

Column: Symmetry C18, 50 mm×2.1 mm, 3.5 µm; temperature: 40° C.; Flow rate=0.5 mlmin$^{-1}$; mobile phase A=CH$_3$CN+0.1% formic acid, mobile phase B=water+0.1% formic acid, gradient: 0.0 min 5% A, →1 min 5% A, →5 min 90% A, →6 min 90% A.

Method 8: Instrument Micromass Platform LCZ

Column: Symmetry C18, 150 mm×2.1 mm, 5 µm; temperature: 40° C.; Flow rate=0.5 mlmin$^{-1}$; mobile phase A=CH$_3$CN+0.1% formic acid, mobile phase B=water+0.1% formic acid, gradient: 0.0 min 10% A, →9 min 90% A, →10 min 90% A.

SYNTHESIS EXAMPLES

Example 1

5-Chloro-N-(1,3-dioxo-2,3-dihydro-1H-isoindol-4-yl)-2-thiophenecarboxamide

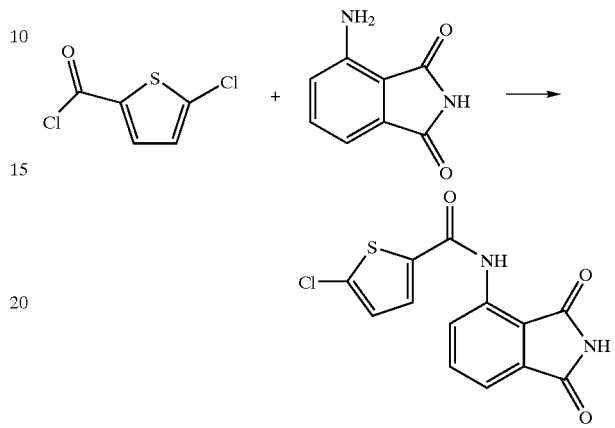

At 0° C., 7.8 g (43.7 mmol) of 3-aminophthalimide are dissolved with stirring in 200 ml of pyridine. Over a period of 5 min, 5-chloro-2-thiophenecarbonyl chloride (which is obtained by boiling 5-chloro-2-thiophenecarboxylic acid in SOCl$_2$) is then added. The reaction mixture is stirred at room temperature monitored by TLC, the initially clear solution turning into a slurry. Another 200 ml of THF are added, and the mixture is stirred at room temperature overnight.

The mixture is then poured into 500 ml of water and extracted with ethyl acetate. Relatively large amounts of poorly soluble crystals remain in the aqueous phase, these crystals are filtered off with suction. The crystals are dissolved in 200 ml of THF and the solution is dried with magnesium sulfate. The solution is concentrated using a rotary evaporator and the residue is triturated with ether and filtered off with suction. This gives 3.5 g (26.4% of theory) of the desired compound.

Example 2

2-[3-(Hydroxymethyl)phenoxy]acetonitrile 25.3 g (203.8 mmol) of 3-hydroxybenzyl alcohol are dissolved in 50 ml of dimethylformamide, and 400 ml of acetone and 28.17 g (203.8 mmol) of finely ground potassium carbonate are added. After 5 minutes of stirring, 24.45 g (203.8 mmol) of bromoacetonitrile are added, and the mixture is boiled under reflux for 72 hours. The mixture is filtered and the filtrate is concentrated under reduced pressure. The residue is dissolved in ethyl acetate and washed with 10% strength aqueous sodium hydroxide solution and then with water. The organic phase is dried over magnesium sulfate and filtered through a short silica gel column (mobile phase toluene->toluene/ethyl acetate=1:1). Evaporation gives 163.18 g (86% of theory) of an oil. R$_f$ (SiO$_2$, toluene/ethyl acetate=1:1)=0.41.

The following compounds were obtained analogously:

Example 3

2-[4-(Hydroxymethyl)phenoxy]acetonitrile $R_f$ (SiO$_2$, toluene/ethyl acetate=1:1)=0.5; yield 34.1%.

Example 4

2-[3-(Hydroxymethyl)phenoxy]propionitrile $R_f$ (SiO$_2$, toluene/ethyl acetate=1:1)=0.43; yield 36.5%.

Example 5

5-Chloro-N-{2-[3-(cyanomethoxy)benzyl]-1,3-dioxo-2,3-dihydro-1H-isoindol-4-yl}-2-thiophenecarboxamide

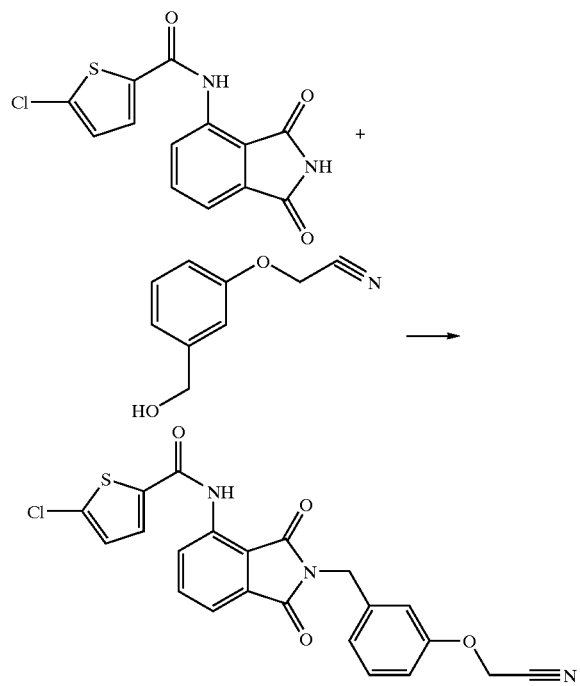

1.46 g (8.94 mmol) of 2-[3-(hydroxymethyl)phenoxy]acetonitrile, 2.5 g (8.15 mmol) of 5-chloro-N-(1,3-dioxo-2,3-dihydro-1H-isoindol-4-yl)-2-thiophenecarboxamide and 4.28 g (16.3 mmol) of triphenylphosphine are, under argon, dissolved in 250 ml of tetrahydrofuran. 2.84 g (16.3 mmol) of DEAD (diethyl azodicarboxylate) are added, and the mixture is stirred at room temperature overnight. 10 g of silica gel are added and the mixture is concentrated under reduced pressure and chromatographed on a silica gel column (gradient: toluene->toluene/ethyl acetate=4:1). This gives 2.37 g (64.4% of theory) of the target compound of melting point 164° C. $R_f$ (SiO$_2$, toluene/ethyl acetate=4:1): 0.45.

The following compounds were obtained analogously:

Example 6

5-Chloro-N-{2-[4-(cyanomethoxy)benzyl]-1,3-dioxo-2,3-dihydro-1H-isoindol-4-yl}-2-thiophenecarboxamide Yield 32%; m.p. 199° C.; $R_f$ (SiO$_2$, toluene/ethyl acetate=4:1)=0.66.

Example 7

5-Chloro-N-{2-[3-(1-cyanoethoxy)benzyl]-1,3-dioxo-2,3-dihydro-1H-isoindol-4-yl}-2-thiophenecarboxamide Yield 70.2%; m.p. 88° C.; $R_f$ (SiO$_2$, toluene/ethyl acetate 4:1)=0.74.

Example 8

2-{4-[(4-Nitro-1,3-dioxo-1,3-dihydro-2H-isoindol-2-yl)methyl]phenyl}acetonitrile

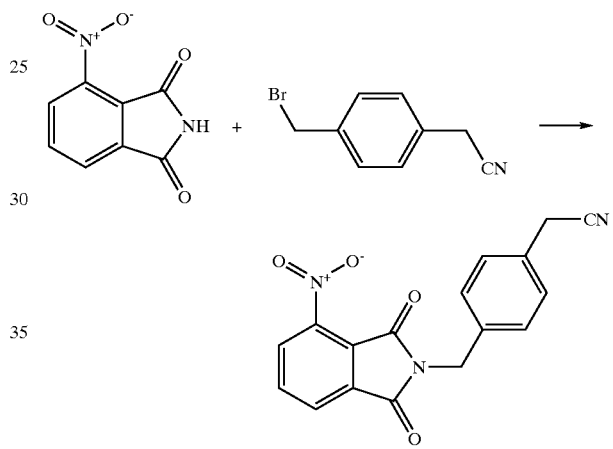

9.79 g (50.93 mmol) of 3-nitrophthalimide are dissolved in 450 ml of DMF, and 10.56 g (76.39 mmol) of potassium carbonate are added. The suspension is treated with ultrasound for 10 min. 10.7 g (50.93 mmol) of 2-[4-(bromomethyl)phenyl]acetonitrile (obtained by reaction of 2-(4-methylphenyl)acetonitrile with N-bromosuccinimide (NBS) and azobisisobutyronitrile (AIBN) in carbon tetrachloride, cf. E. Laurent, B. Marquet, R. Tardivel; *Tetrahedron*; 47; 24; 1991; pp. 3969–3980) are then added, and the reaction mixture is stirred at room temperature for 20 h. The suspension is then poured into a mixture of 300 ml of 2 N hydrochloric acid and 3 l of water. The crystals formed are filtered off with suction, washed with water and dried under reduced pressure. This gives 12 g (73% of theory) of the desired compound. $R_f$ (SiO$_2$, CH$_2$Cl$_2$/EtOH=100/1)= 0.55, MS=322.2 (M+H$^+$).

The following compounds were prepared analogously:

Example 9

From 3-nitrophthalimide and 2-[3-(bromomethyl)phenyl]acetonitrile (obtained by reaction of 2-(3-methylphenyl)acetonitrile with NBS and AIBN in carbon tetrachloride):

{3-[(4-Nitro-1,3-dioxo-1,3-dihydro-2H-isoindol-2-yl)methyl]phenyl}acetonitrile

MS=322 (M+H), rt (Method 4)=3.99 min.

Example 10

From 3-nitrophthalimide and 4-bromobutyronitrile:

4-(4-Nitro-1,3-dioxo-1,3-dihydro-2H-isoindol-2-yl)butyronitrile

MS=260 (M+H), rt (Method 4)=3.36 min.

Example 11

From 3-nitrophthalimide and 5-bromovaleronitrile:

5-(4-Nitro-1,3-dioxo-1,3-dihydro-2H-isoindol-2-yl)valeronitrile

MS=274 (M+H), rt (Method 4)=3.59 min.

Example 12

From 3-nitrophthalimide and 4-(2-bromoethyl)benzonitrile (prepared from 4-(2-hydroxyethyl)benzonitrile, see G. Wagner, H. Vieweg, *Pharmazie*; 37; 1; 1982; pp. 13–16):

4-[2-(4-Nitro-1,3-dioxo-1,3-dihydro-2H-isoindol-2-yl)ethyl]benzonitrile $R_f$ (SiO$_2$, cyclohexane/EtOAc=5/1)=0.6, rt (Method 4)=4.16 min.

Example 13

From tert-butyl 1,3-dioxo-2,3,3a,4,7,7a-hexahydro-1H-isoindol-4-ylcarbamate (preparation see DE 4123918) and 4-(2-bromoethyl)benzonitrile:

tert-Butyl 2-[2-(4-cyanophenyl)ethyl]-1,3-dioxo-2,3,3a,4,7,7a-hexahydro-1H-isoindol-4-ylcarbamate MS=337 (M—tert-Bu), rt (Method 4)=4.56 min.

Example 14

[4-(2-Hydroxyethyl)phenyl]acetonitrile 3.85 g (18.81 mmol) of 4-bromomethylphenylacetic acid are dissolved in 150 ml of THF, and 20 ml of a 1M solution of BH$_3$ in THF is added slowly with stirring, at 0° C. The reaction mixture is then slowly warmed to room temperature and stirred overnight at room temperature. 2M hydrochloric acid is added, and the reaction mixture is extracted with ethyl acetate. The organic phase is dried over magnesium sulfate, filtered and concentrated. 3.64 g (16.92 mmol) of the 2-[4-(bromomethyl)phenyl]ethanol thus obtained are, without further purification, dissolved in 36 ml of DMSO, and 1.65 g (25.38 mmol) of potassium cyanide are added. The reaction mixture is stirred at room temperature for 1 h and then poured into diethyl ether/sat. aqueous sodium bicarbonate solution. The organic phase is washed three times with water, dried over magnesium sulfate, filtered and concentrated. This gives 2.5 g of product.

rt (Method 4)=2.66 min.

Example 15

{4-[2-(4-Nitro-1,3-dioxo-1,3-dihydro-2H-isoindol-2-yl)ethyl]phenyl}acetonitrile

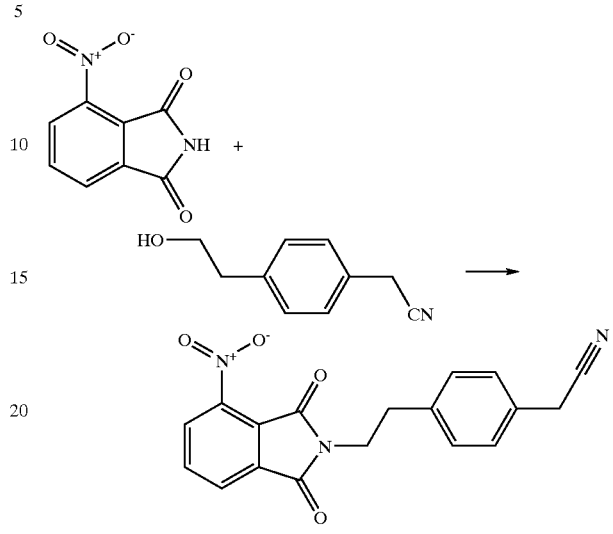

Under argon, 4.66 g (26.75 mmol) of diethyl azodicarboxylate are initially charged in 50 ml of THF. 2.57 g (13.38 mmol) of 3-nitrophthalimide, 2.37 g (14.71 mmol) of [4-(2-hydroxyethyl)phenyl]acetonitrile and 7.02 g (26.75 mmol) of triphenylphosphine are added, and the mixture is stirred at room temperature for 20 h. The reaction mixture is then poured into ether/aqueous buffer solution pH 7, the phases are separated and the organic phase is dried over magnesium sulfate, filtered and concentrated using a rotary evaporator. The crude product is chromatographed on silica gel (CH$_2$Cl$_2$). This gives 3.08 g (69% of theory) of the desired compound.

MS=336.3 (M+H), $R_f$ (SiO$_2$, CH2Cl2/EtOH=100/1)= 0.37.

The following compounds were prepared analogously:

Example 16

From 3-nitrophthalimide and 3-(2-hydroxyethyl)benzonitrile (prepared from 2-(3-nitrophenyl)ethanol by catalytic reduction of the nitro group and subsequent Sandmeyer reaction, cf. G. Wagner, H. Vieweg, *Pharmazie*; 37, 1, 1982; pp. 13–16):

3-[2-(4-Nitro-1,3-dioxo-1,3-dihydro-2H-isoindol-2-yl)ethyl]benzonitrile $R_f$ (SiO$_2$, CH$_2$Cl$_2$)=0.23, rt (Method 4)=4.29 min.

Example 17

From tert-butyl 1,3-dioxo-2,3,3a,4,7,7a-hexahydro-1H-isoindol-4-ylcarbamate and 3-(3-hydroxy-1-propenyl)benzonitrile (prepared from 3-(3-cyanophenyl)-2-propenoic acid (G. Wagner, C. Garbe, P. Richter, *Pharmazie*; 28; 11/12; 1973; pp. 724–729) by reduction with borane):

tert-Butyl 2-[(3-(3-cyanophenyl)-2-propenyl]-1,3-dioxo-2,3,3a,4,7,7a-hexahydro-1H-isoindol-4-ylcarbamate MS=408 (M+H), 352 (M+H—tert-Bu), rt (Method 4)=4.59 min.

Example 18

From tert-butyl 1,3-dioxo-2,3,3a,4,7,7a-hexahydro-1H-isoindol-4-ylcarbamate and 3-(3-hydroxy-1-propyl)benzonitrile (preparation see H. Vieweg, G. Wagner, *Pharmazie*; 37; 3; 1982; pp. 178–182):

tert-Butyl 2-[3-(3-cyanophenyl)propyl]-1,3-dioxo-2,3,3a,4,7,7a-hexahydro-1H-isoindol-4-ylcarbamate MS=410 (M+H), 354 (M+H—tert-Bu), 310 (M+H—tert-BuCO$_2$), rt (Method 4)=4.68 min.

Example 19

From tert-butyl 1,3-dioxo-2,3,3a,4,7,7a-hexahydro-1H-isoindol-4-ylcarbamate and 3-(2-hydroxyethyl)benzonitrile:

tert-Butyl 2-[2-(3-cyanophenyl)ethyl]-1,3-dioxo-2,3,3a,4,7,7a-hexahydro-1H-isoindol-4-ylcarbamate MS=396 (M+H), 340 (M+H—tert-Bu), 296 (M+H—tert-BuCO$_2$), rt (Method 4)=4.59 min.

Example 20

2-{4-[(4-Amino-1,3-dioxo-1,3-dihydro-2H-isoindol-2-yl)methyl]phenyl}-acetonitrile

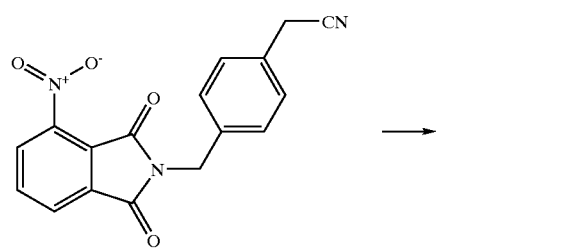

2.4 g (7.47 mmol) of 2-{4-[(4-nitro-1,3-dioxo-1,3-dihydro-2H-isoindol-2-yl)methyl]-phenyl}acetonitrile are dissolved in 130 ml of a mixture of THF/EtOAc/EtOH (7/4/2), 0.2 g of palladium-on-carbon (10%) is added and the mixture is stirred at room temperature under an atmosphere of hydrogen (1.013 bar) for 6 h. The reaction mixture is then filtered, the solvent is removed under reduced pressure and the crude product is chromatographed on silica gel (CH$_2$Cl$_2$/EtOH=100/0 to 100/1). This gives 1.78 g (82% of theory) of the desired compound.

R$_f$(SiO$_2$, CH$_2$Cl$_2$/EtOH=50/1)=0.42, MS=292 (M+H$^+$), rt (Method 4)=3.77 min.

The following amines were prepared analogously by reduction of the nitro compounds in THF/EtOAc/EtOH or EtOAc/EtOH mixtures:

Example 21

{3-[(4-Amino-1,3-dioxo-1,3-dihydro-2H-isoindol-2-yl)methyl]phenyl}acetonitrile

MS=292 (M+H), rt (Method 4)=3.85 min.

Example 22

4-(4-Amino-1,3-dioxo-1,3-dihydro-2H-isoindol-2-yl)butyronitrile

MS=230 (M+H), rt (Method 4)=3.09 min.

Example 23

5-(4-Amino-1,3-dioxo-1,3-dihydro-2H-isoindol-2-yl)valeronitrile

MS=244 (M+H), rt (Method 4)=3.33 min.

Example 24

4-[2-(4-Amino-1,3-dioxo-1,3-dihydro-2H-isoindol-2-yl)ethyl]benzonitrile

MS=292 (M+H), rt (Method 4)=3.97 min.

Example 25

{4-[2-(4-Amino-1,3-dioxo-1,3-dihydro-2H-isoindol-2-yl)ethyl]phenyl}acetonitrile

MS=306 (M+H), rt (Method 4)=3.98 min.

Example 26

3-[2-(4-Amino-1,3-dioxo-1,3-dihydro-2H-isoindol-2-yl)ethyl]benzonitrile

MS=292 (M+H), rt (Method 4)=3.98 min.

Example 27

4-[2-(4-Amino-1,3-dioxo-1,3,3a,4,7,7a-hexahydro-2H-isoindol-2-yl)ethyl]-benzonitrile

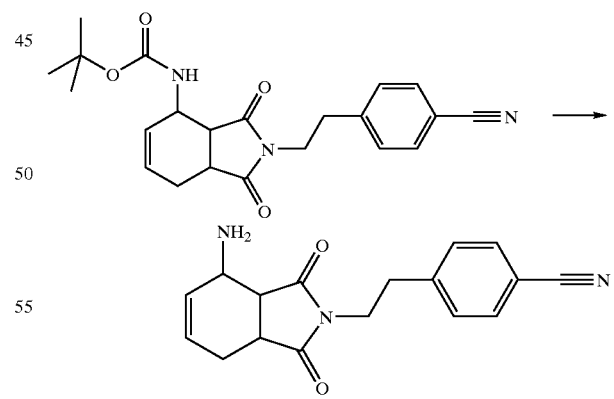

1.008 g (2.55 mmol) of tert-butyl 2-[2-(4-cyanophenyl)ethyl]-1,3-dioxo-2,3,3a,4,7,7a-hexahydro-1H-isoindol-4-ylcarbamate are dissolved in 20 ml of dichloromethane, and 0.79 ml (10.2 mmol) of trifluoroacetic acid is added. After 4 h of stirring at room temperature, the reaction mixture is concentrated using a rotary evaporator and worked up using EtOAc and saturated aqueous NaHCO$_3$ solution. The organic phase is dried over magnesium sulfate, filtered and concentrated using a rotary evaporator. The crude product is chromatographed on silica gel (CH$_2$Cl$_2$/EtOH=50/1+0.5% aqueous NH$_3$ solution (25% strength)). This gives 530 mg (70% of theory) of the desired compound. MS=337 (M+H+ MeCN), 296 (M+H), rt (Method 4)=2.04 min.

The following amines were prepared analogously by reacting the corresponding tert-butoxycarbonyl-protected compounds with trifluoroacetic acid in dichloromethane:

Example 28

3-[3-(4-Amino-1,3-dioxo-1,3,3a,4,7,7a-hexahydro-2H-isoindol-2-yl)-1-propenyl]benzonitrile MS=349 (M+H+MeCN), 308 (M+H), rt (Method 4)=2.26 min.

Example 29

3-[3-(4-Amino-1,3-dioxo-1,3,3a,4,7,7a-hexahydro-2H-isoindol-2-yl)propyl]-benzonitrile MS=310 (M+H), rt (Method 4)=2.28 min.

Example 30

3-[2-(4-Amino-1,3-dioxo-1,3,3a,4,7,7a-hexahydro-2H-isoindol-2-yl)ethyl]-benzonitrile MS=296 (M+H), rt (Method 4)=2.04 min.

Example 31

5-Chloro-N-{2-[4-(cyanomethyl)benzyl]-1,3-dioxo-2,3-dihydro-1H-isoindol-4-yl}-2-thiophenecarboxamide

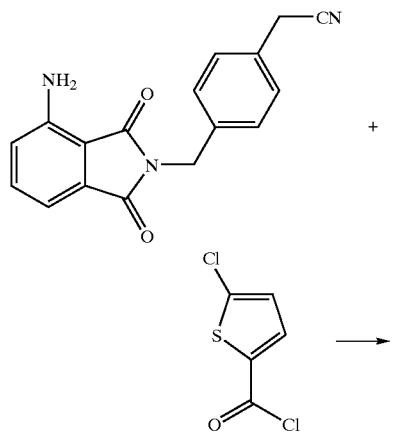

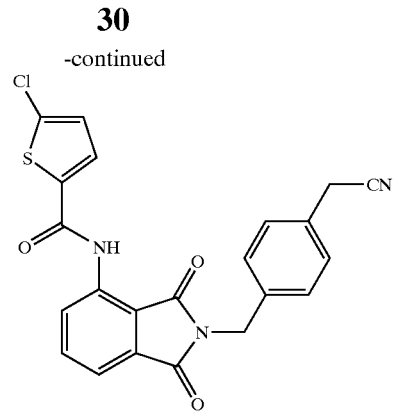

1.07 g (3.67 mmol) of 2-{4-[(4-amino-1,3-dioxo-1,3-dihydro-2H-isoindol-2-yl)methyl]phenyl}acetonitrile, 1.33 g (7.35 mmol) of 5-chloro-2-thiophenecarbonyl chloride (obtained by reaction of 5-chloro-2-thiophenecarboxylic acid with SOCl$_2$) and 90 mg (0.74 mmol) of 4-DMAP are stirred in 10 ml of pyridine at room temperature for 20 h. The reaction mixture is poured into 2 N hydrochloric acid and the precipitate formed is filtered off with suction, washed with water and dried under reduced pressure. This gives 1.57 g (98% of theory) of the desired compound. R$_f$ (SiO$_2$, CH$_2$Cl$_2$)=0.25. If required, the product can be purified by silica gel chromatography using methylene chloride/ethanol mixtures.

The following compounds were prepared analogously by reacting the corresponding amines with 5-chloro-2-thiophenecarbonyl chloride:

Example 32

5-Chloro-N-{2-[3-(cyanomethyl)benzyl]-1,3-dioxo-2,3-dihydro-1H-isoindol-4-yl}-2-thiophenecarboxamide MS=436 (M+H), rt (Method 4)=5.27 min.

Example 33

5-Chloro-N-[2-(3-cyanopropyl)-1,3-dioxo-2,3-dihydro-1H-isoindol-4-yl]-2-thiophenecarboxamide MS=374 (M+H), rt (Method 4)=4.80 min.

Example 34

5-Chloro-N-[2-(4-cyanobutyl)-1,3-dioxo-2,3dihydro-1H-isoindol-4-yl]-2-thiophenecarboxamide MS=388 (M+H), rt (Method 4)=5.03 min.

Example 35

5-Chloro-N-{2-[2-(4-cyanophenyl)ethyl]-1,3-dioxo-2,3-dihydro-1H-isoindol-4-yl}-2-thiophenecarboxamide MS=436 (M+H), rt (Method 4)=5.42 min.

Example 36

5-Chloro-N-(2-{2-[4-(cyanomethyl)phenyl]ethyl}-1,3-dioxo-2,3-dihydro-1H-isoindol-4-yl)-2-thiophenecarboxamide R$_f$ (SiO$_2$, CH$_2$Cl$_2$/EtOH=100/1)=0.5, rt (Method 4)=5.52 min.

Example 37

5-Chloro-N-{2-[2-(3-cyanophenyl)ethyl]-1,3-dioxo-2,3-dihydro-1H-isoindol-4-yl}-2-thiophenecarboxamide MS=436 (M+H), rt (Method 4)=5.45 min.

Example 38

5-Chloro-N-{2-[2-(3-cyanophenyl)ethyl]-1,3-dioxo-2,3,3a,4,7,7a-hexahydro-1H-isoindol-4-yl}-2-thiophenecarboxamide

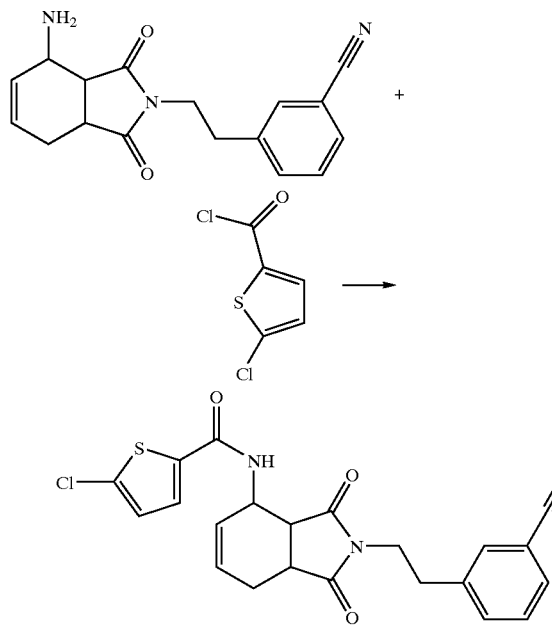

54 mg (0.183 mmol) of 3-[2-(4-amino-1,3-dioxo-1,3,3a,4,7,7a-hexahydro-2H-isoindol-2-yl)ethyl]benzonitrile are dissolved in 5 ml of THF, and 20.4 mg (0.2 mmol) of triethylamine and 36.4 mg (0.2 mmol) of 5-chloro-2-thiophenecarbonyl chloride are added at 0° C. The reaction mixture is then stirred at room temperature for 2 h and then poured into ethyl acetate and sat. aqueous NaHCO$_3$ solution. The organic phase is dried over magnesium sulfate, filtered and concentrated. The crude product is chromatographed on silica gel (CH$_2$Cl$_2$/EtOH=100/0–100/1). This gives 58 mg (72% of theory) of the desired compound.

MS=440 (M+H), rt (Method 4)=4.59 min.

Alternatively, the reaction can also be carried out in dichloromethane instead of THF.

The following compounds were prepared analogously by reacting the corresponding amines with 5-chloro-2-thiophenecarbonyl chloride:

Example 39

5-Chloro-N-{2-[2-(4-cyanophenyl)ethyl]-1,3-dioxo-2,3,3a,4,7,7a-hexahydro-1H-isoindol-4-yl}-2-thiophenecarboxamide MS=440 (M+H), R$_f$ (SiO$_2$, cyclohexane/ethyl acetate=1/1)=0.27.

Example 40

5-Chloro-N-{2-[3-(3-cyanophenyl)-2-propenyl]-1,3-dioxo-2,3,3a,4,7,7a-hexahydro-1H-isoindol-4-yl}-2-thiophenecarboxamide MS=452 (M+H), rt (Method 4)=4.59 min.

Example 41

5-Chloro-N-{2-[3-(3-cyanophenyl)propyl]-1,3-dioxo-2,3,3a,4,7,7a-hexahydro-1H-isoindol-4-yl}-2-thiophenecarboxamide MS=454 (M+H), rt (Method 4)=4.68 min.

Example 42

5-Chloro-N-{2-[4-(cyanomethyl)benzyl]-3-hydroxy-1-oxo-2,3-dihydro-1H-isoindol-4-yl}-2-thiophenecarboxamide and 5-chloro-N-{2-[4-(cyanomethyl)-benzyl]-1-hydroxy-3-oxo-2,3-dihydro-1H-isoindol-4-yl}-2-thiophenecarboxamide

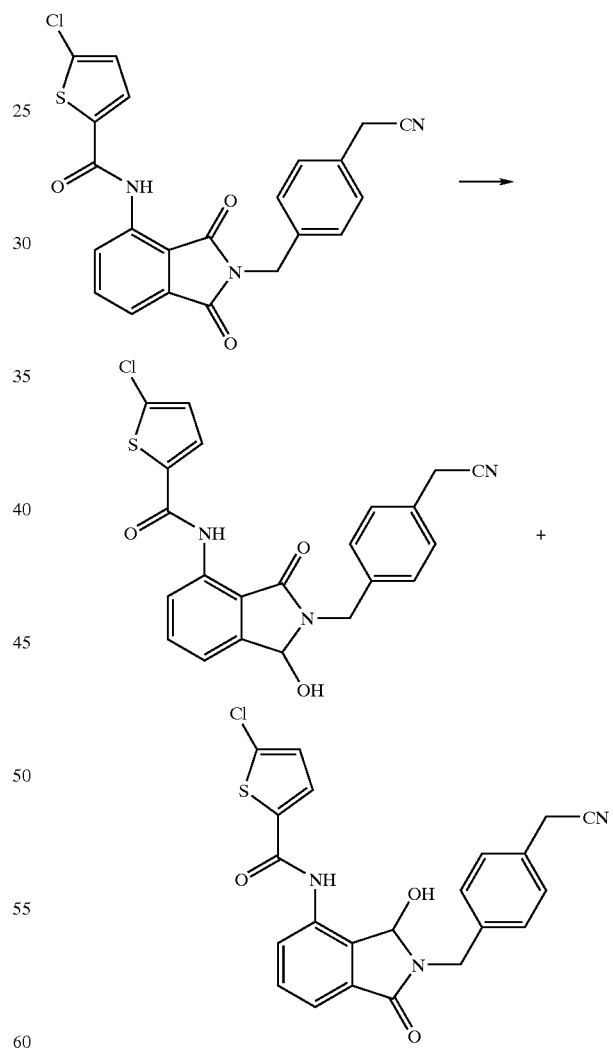

3 g (6.88 mmol) of 5-chloro-N-{2-[4-(cyanomethyl) benzyl]-1,3-dioxo-2,3-dihydro-1H-isoindol-4-yl}-2-thiophenecarboxamide are dissolved in a mixture of 200 ml of methanol and 400 ml of dichloromethane. 1.04 g (27.53 mmol) of sodium borohydride are added to the solution, and the mixture is stirred at room temperature for 4 h. The reaction mixture is then carefully poured into 2 N hydrochloric acid. The phases are separated, the organic phase is dried over magnesium sulphate, filtered, and the solvent is removed under reduced pressure. The crude product is chromatographed on silica gel (CH$_2$Cl$_2$/EtOH/conc. ammonia solution=200/1/0.1 to 20/1/0.1). 5-Chloro-N-{2-[4-(cyanomethyl)benzyl]-1-hydroxy-3-oxo-2,3-dihydro-1H-isoindol-4-yl}-2-thiophenecarboxamide is eluted first. 1.07 g (36% of theory) of this compound are obtained.

R$_f$ (SiO$_2$, CH$_2$Cl$_2$/EtOH/conc. ammonia solution=50/1/0.01)=0.17, MS=438.3 (M+H$^+$).

5-Chloro-N-{2-[4-(cyanomethyl)benzyl]-3-hydroxy-1-oxo-2,3-dihydro-1H-isoindol-4-yl}-2-thiophenecarboxamide is eluted as second fraction. 0.85 g (28% of theory) of this compound is obtained.

R$_f$ (SiO$_2$, CH$_2$Cl$_2$/EtOH/conc. ammonia solution=50/1/0.01)=0.11, MS=438.3 (M+H$^+$).

Example 43

5-Chloro-N-{2-[4-(cyanomethyl)benzyl]-5-5-oxo-2,3-dihydro-1H-isoindol-4-yl}-2-thiophenecarboxamide

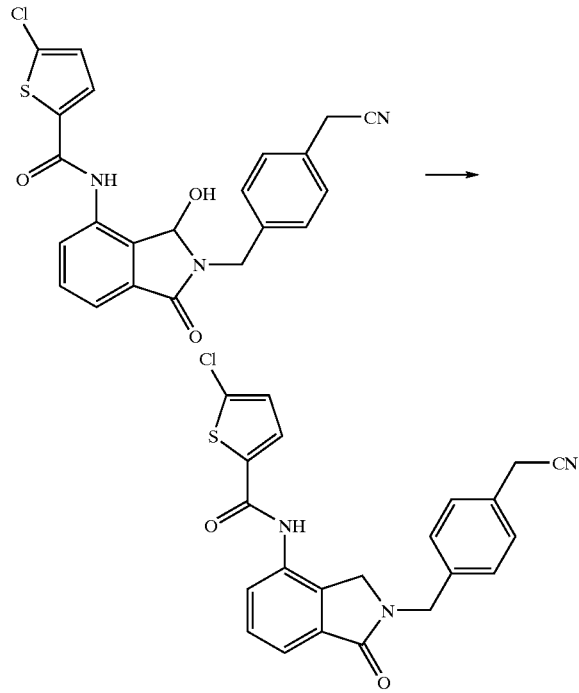

807 mg (1.84 mmol) of 5-chloro-N-{2-[4-(cyanomethyl)benzyl]-3-hydroxy-1-oxo-2,3-dihydro-1H-isoindol-4-yl}-2-thiophenecarboxamide are dissolved in a mixture of 20 ml of dichloromethane and 1.7 ml of trifluoroacetic acid. 429 mg (3.69 mmol) of triethylsilane are then added, and the mixture is stirred at room temperature overnight. The reaction mixture is diluted with dichloromethane and washed twice with sat. NaHCO$_3$ solution and once with 2 M hydrochloric acid. The organic phase is dried over magnesium sulfate and filtered and the solvent is removed under reduced pressure.

This gives 765 mg (98% of theory) of the desired compound.

R$_f$ (SiO$_2$, CH$_2$Cl$_2$/EtOH=20/1)=0.42, MS=422.3 (M+H$^+$).

Example 44

Analogously, it is possible to convert 5-chloro-N-{2-[4-(cyanomethyl)benzyl]-1-hydroxy-3-oxo-2,3-dihydro-1H-isoindol-4-yl}-2-thiophenecarboxamide into 5-chloro-N-{2-[4-(cyanomethyl)benzyl]-3-oxo-2,3-dihydro-1H-isoindol-4-yl}-2-thiophenecarboxamide.

R$_f$ (SiO$_2$, CH$_2$Cl$_2$/EtOH=100/1)=0.54, MS=422.3 (M+H$^+$).

Example 45

N-{2-[4-(2-Amino-2-thioxoethyl)benzyl]-1,3-dioxo-2,3-dihydro-1H-isoindol-4-yl}-5-chloro-2-thiophenecarboxamide

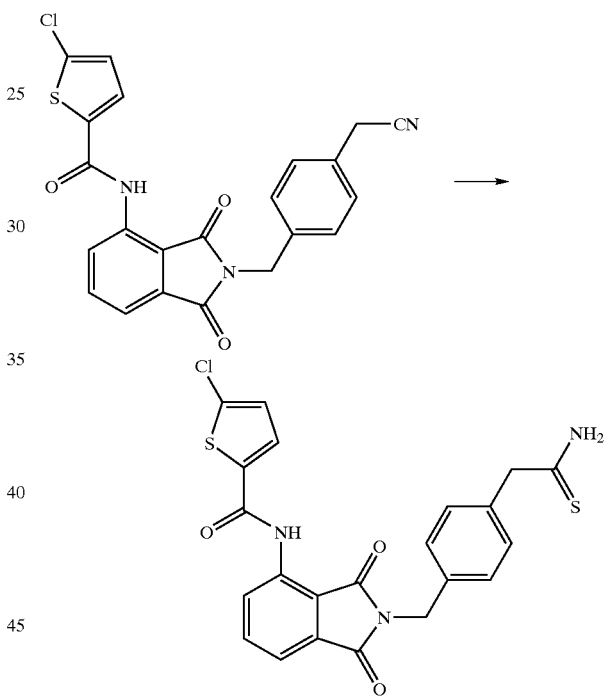

1.38 g (3.16 mmol) of 5-chloro-N-{2-[4-(cyanomethyl)benzyl]-1,3-dioxo-2,3-dihydro-1H-isoindol-4-yl}-2-thiophenecarboxamide are dissolved in 10 ml of a saturated solution of hydrogen sulfide in pyridine. 2.56 g (25.31 mmol) of triethylamine are added to the solution, and the mixture is stirred at room temperature for 20 h. A further 10 ml of the saturated hydrogen sulfide/pyridine solution and 1.3 g of triethylamine are then added, and stirring is continued for another 20 h. The reaction mixture is then diluted with EtOAc and washed three times with 2 N hydrochloric acid and once with buffer solution pH 7. The organic phase is dried with magnesium sulfate, filtered and concentrated under reduced pressure. The residue is chromatographed on silica gel. This gives 0.87 g (59% of theory) of the desired compound.

R$_f$ (SiO$_2$, CH$_2$Cl$_2$/EtOH=20/1)=0.41, MS=470 (M+H$^+$).

Example 46

Methyl 2-{4-[(4-{[(5-chloro-2-thienyl)carbonyl]amino}-1,3-dioxo-1,3-dihydro-2H-isoindol-2-yl)methyl]phenyl}ethaneimidothioate

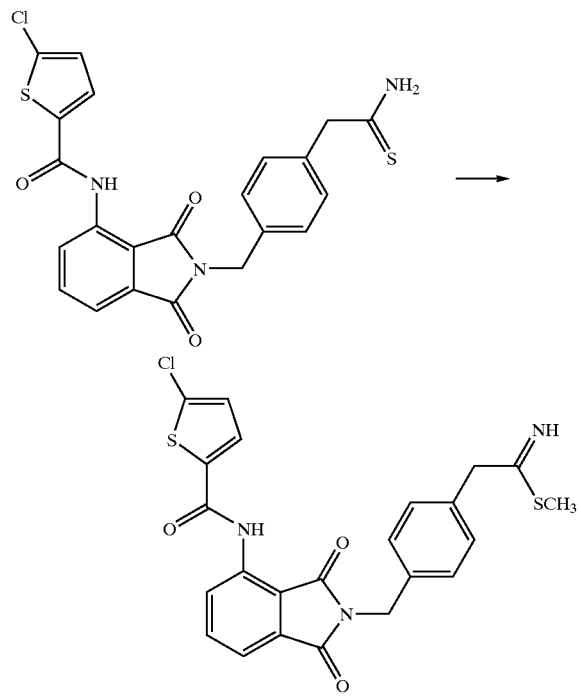

850 mg (1.81 mmol) of N-{2-[4-(2-amino-2-thioxoethyl)benzyl]-1,3-dioxo-2,3-dihydro-1H-isoindol-4-yl}-5-chloro-2-thiophenecarboxamide are dissolved in 150 ml of acetone, and 5.134 g (36.17 mmol) of methyl iodide are added. With stirring, the mixture is heated at 60° C. for 2 h and, after cooling to room temperature, concentrated under reduced pressure. The crude product is used for the next step without further purification.

$R_f$ (SiO$_2$, EtOAc/cyclohexane=1/1)=0.40.

Example 47

N-{2-[4-(2-Amino-2-iminoethyl)benzyl]-1,3-dioxo-2,3-dihydro-1H-isoindol-4-yl}-5-chloro-2-thiophenecarboxamide

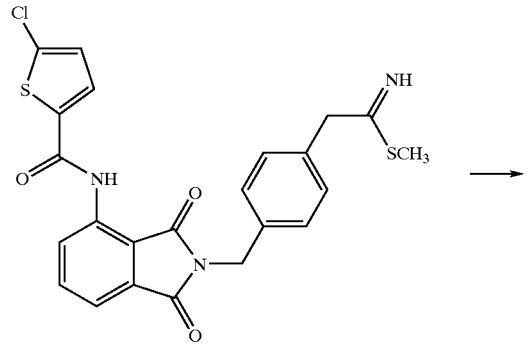

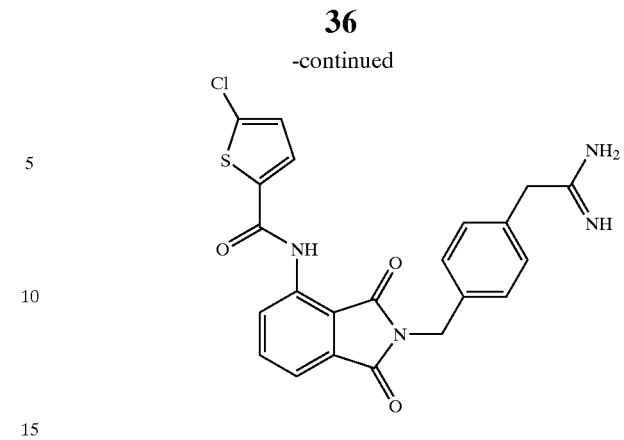

320 mg (0.661 mmol) of methyl 2-{4-[(4-{[(5-chloro-2-thienyl)carbonyl]amino}-1,3-dioxo-1,3-dihydro-2H-isoindol-2-yl)methyl]phenyl}ethaneimidothioate are suspended in 40 ml of methanol, and 153 mg (1.98 mmol) of ammonium acetate and 106 mg (1.98 mmol) of ammonium chloride are added. The mixture is stirred at room temperature overnight, diluted with methanol and methylene chloride until a clear solution is formed and adsorbed on silica gel. Chromatography on silica gel (CH$_2$Cl$_2$/EtOH=10/1 to 3/1) gives the desired compound. The product is dissolved in methanol and methylene chloride, and trifluoroacetic acid is added. Removal of the solvent under reduced pressure gives 298 mg (80% of theory) of the desired product as trifluoroacetic acid salt.

Alternatively, the purification can also be carried out by chromatography on an RP8 silica gel column (water/acetonitrile=4/1+0.1% trifluoroacetic acid to 1/1+0.1% trifluoroacetic acid).

$R_f$ (SiO$_2$, CH$_2$Cl$_2$/EtOH=5/1)=0.12, MS=453.3 (M+H$^+$).

Example 48

5-Chloro-N-(2-{4-[2-imino-2-(propylamino)ethyl]benzyl}-1,3-dioxo-2,3-dihydro-1H-isoindol-4-yl)-2-thiophenecarboxamide

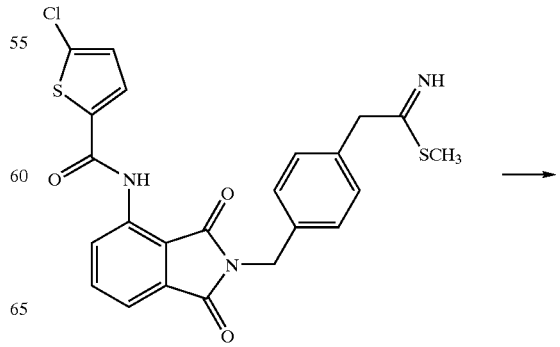

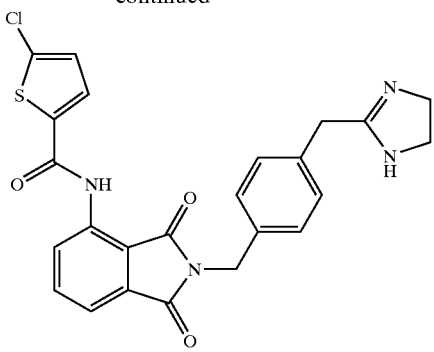

1.5 g (3.1 mmol) of methyl 2-{4-[(4-{[(5-chloro-2-thienyl)carbonyl]amino}-1,3-dioxo-1,3-dihydro-2H-isoindol-2-yl)methyl]phenyl}ethaneimidothioate are suspended in 190 ml of methanol, and 280 mg (4.65.mmol) of ethylenediamine and 370 mg (6.2 mmol) of acetic acid are added. The mixture is stirred at room temperature overnight, diluted with methanol and methylene chloride until a clear solution is formed and adsorbed on silica gel. Chromatography on silica gel ($CH_2Cl_2$/EtOH=10/1 to 3/1) gives 570 mg (31% of theory) of the desired compound. The product is dissolved in methanol and methylene chloride, and trifluoroacetic acid is added. Removal of the solvent under reduced pressure gives the product as trifluoroacetic acid salt. Alternatively, the purification can also be carried out by chromatography on an RP8 silica gel column (water/acetonitrile=4/1+0.1% trifluoroacetic acid to 1/1+0.1% trifluoroacetic acid).

$R_f$ ($SiO_2$, $CH_2Cl_2$/EtOH=5/1)=0.18, MS=479.3 (M+H⁺).

The compounds of the table below are obtained in an analogous manner from the corresponding nitrites by reaction with $H_2S$/pyridine, methyl iodide and ammonium salts, or from corresponding amines or diamines:

| Example | Structure | MS (ESI) (M + H) | HPLC RT (min) (Method) |
|---|---|---|---|
| 49 | 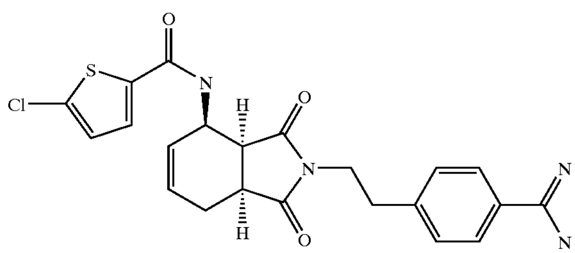 | 457 | 2.604 (4) |
| 50 | 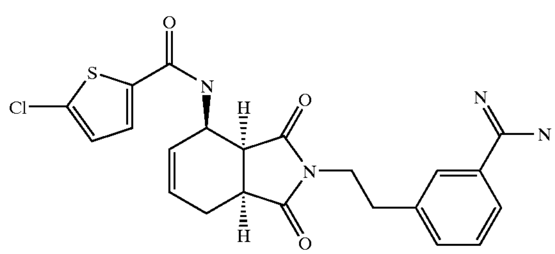 | 457 | 2.627 (4) |
| 51 | 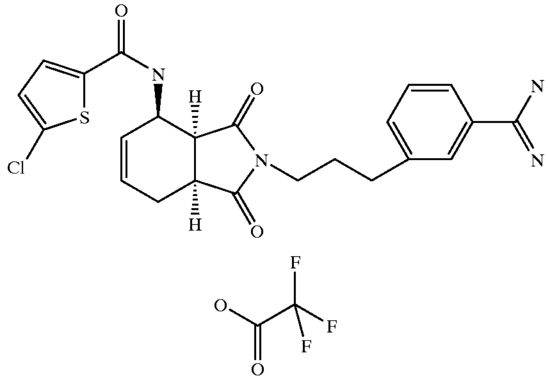 | 471 | 2.751 (4) |

| | | | |
|---|---|---|---|
| 52 | (structure) | 469 | 2.726 (4) |
| 53 | (structure) | 453 | 3.111 (4) |
| 54 | (structure) | 391 | 2.814 (4) |
| 55 | (structure) | 405 | 2.916 (4) |

-continued
| | | | |
|---|---|---|---|
| 56 | 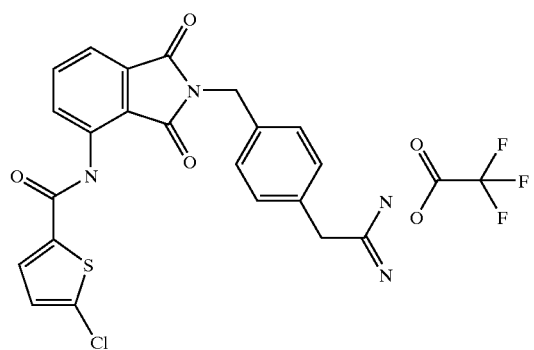 | 453 | 3.155 (4) |
| 57 | 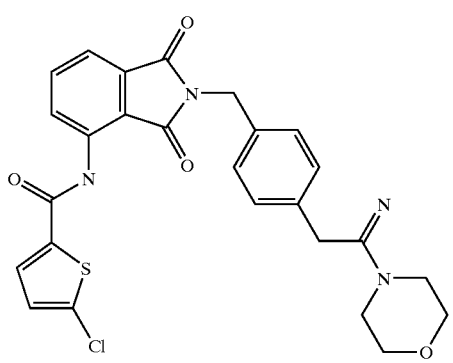 | 523 | 3.240 (4) |
| 58 | 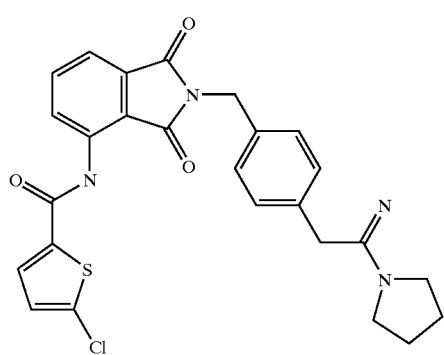 | 507 | 3.368 (4) |
| 59 | 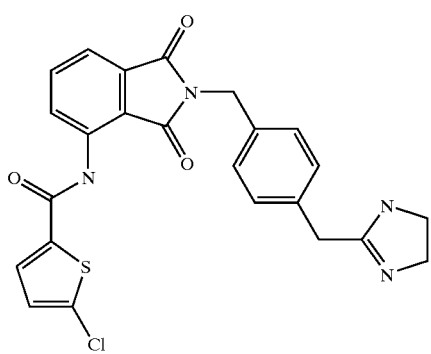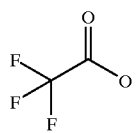 | 479 | 3.202 (4) |

-continued
| | | | |
|---|---|---|---|
| 60 | 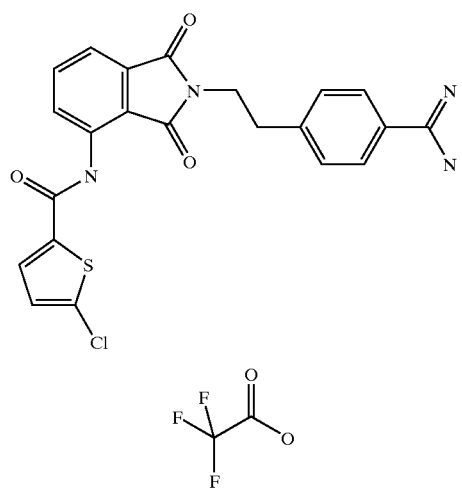 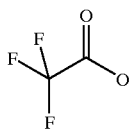 | 453 | 3.153 (4) |
| 61 | 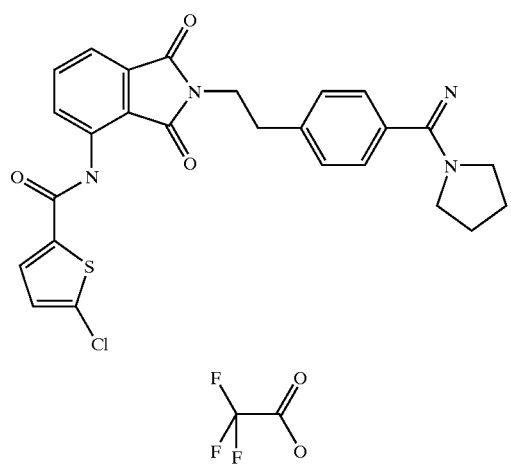 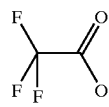 | 507 | 3.379 (4) |
| 62 | 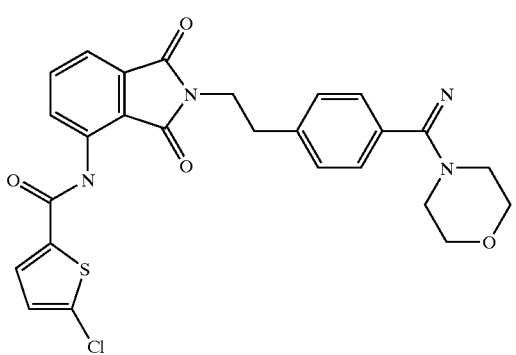 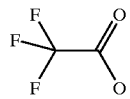 | 523 | 3.251 (4) |

-continued
| | | | |
|---|---|---|---|
| 63 | 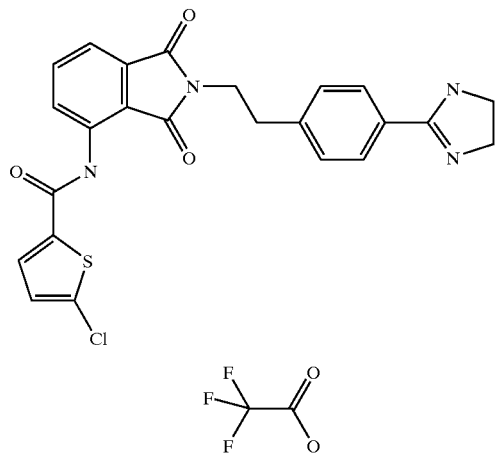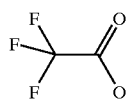 | 479 | 3.187 (4) |
| 64 | 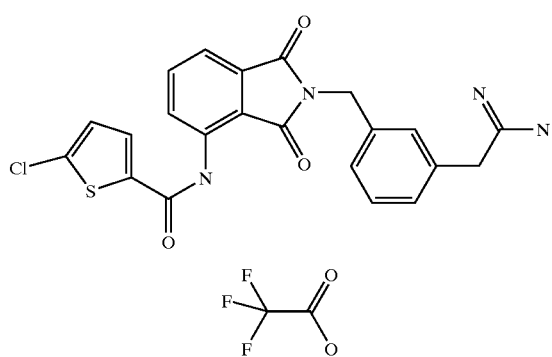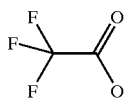 | 453 | 3.294 (4) |
| 65 | 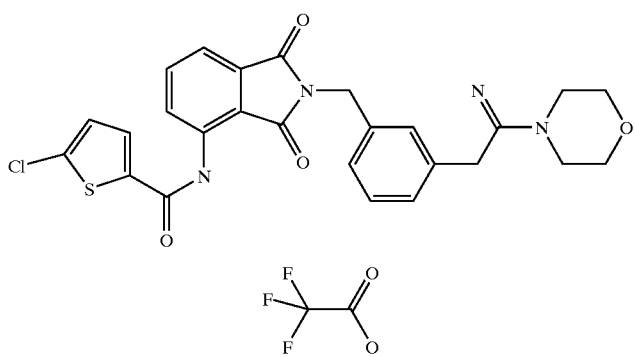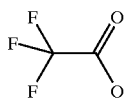 | 523 | 3.337 (4) |
| 66 | 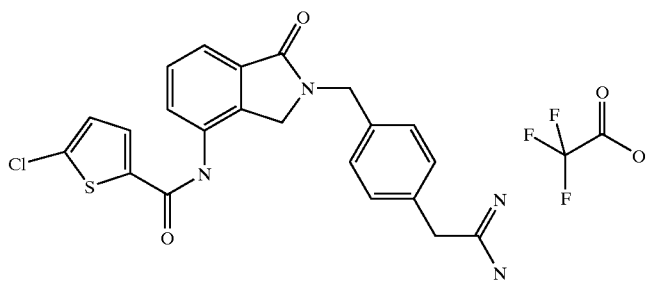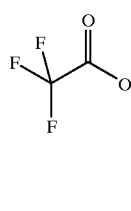 | 439 | 2.697 (4) |

-continued
| | | | |
|---|---|---|---|
| 67 | 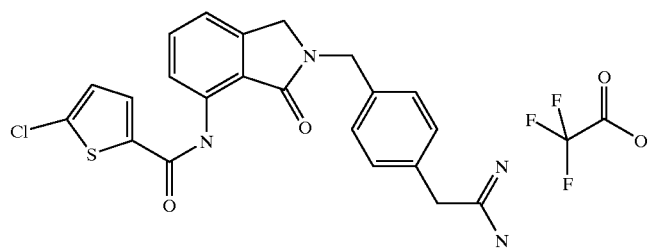 | 439 | 3.336 (4) |
| 68 | 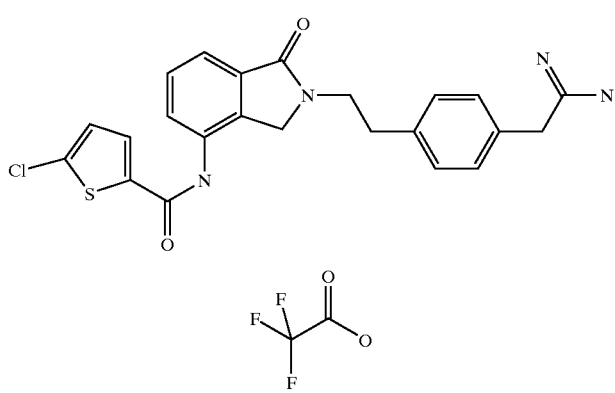 | 453 | 2.808 (4) |
| 69 | 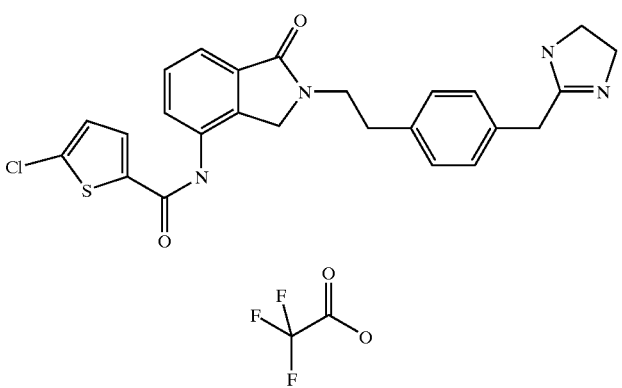 | 479 | 3.335 (4) |
| 70 | 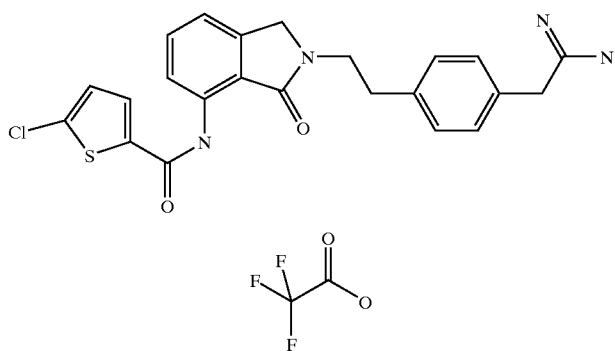 | 453 | 3.242 (4) |

-continued
| | | | |
|---|---|---|---|
| 71 | 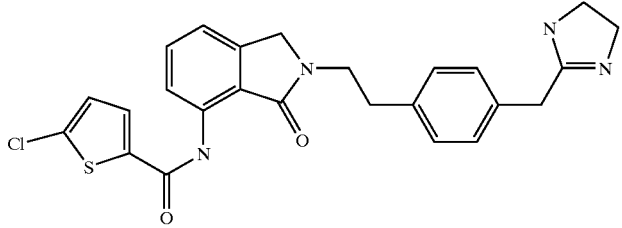 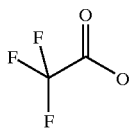 | 479 | 2.840 (4) |
| 72 | 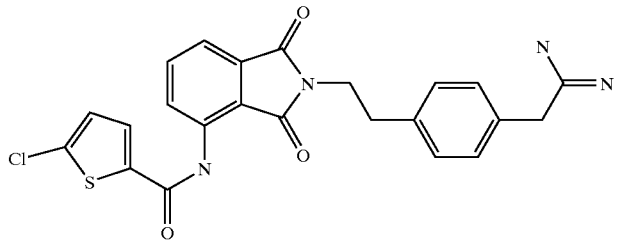 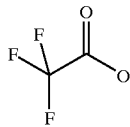 | 467 | 3.30 (5) |
| 73 | 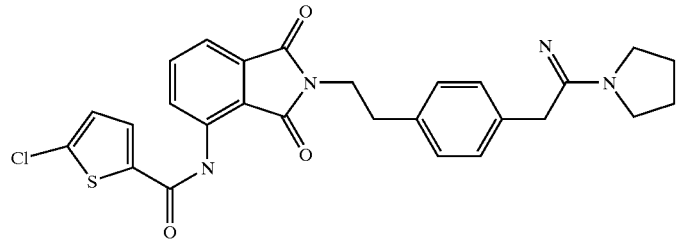 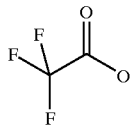 | 521 | 3.567 (4) |
| 74 | 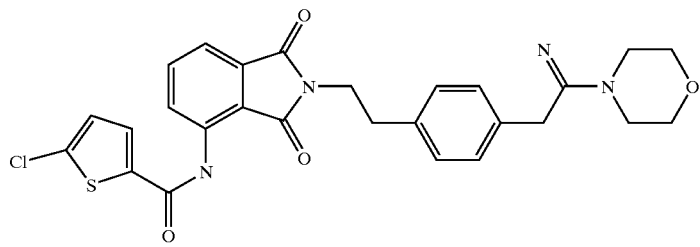 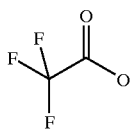 | 537 | 3.33 (5) |

-continued
| | | | |
|---|---|---|---|
| 75 | 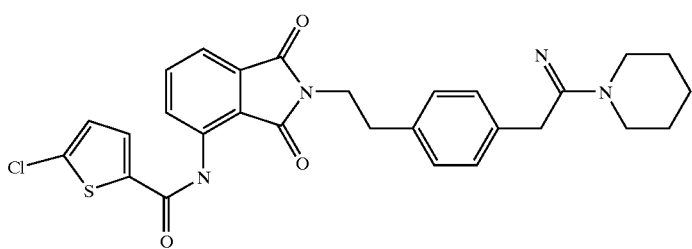<br>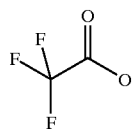 | 535 | 3.49 (5) |
| 76 | 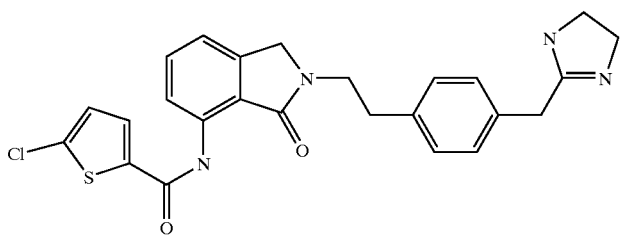<br>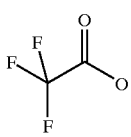 | 507 | 5.67 (8) |
| 77 | 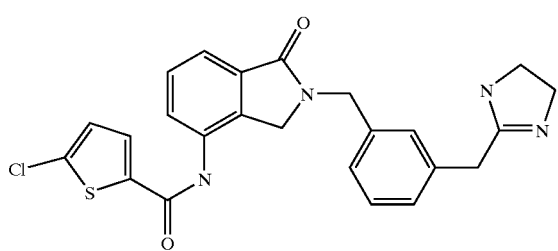<br>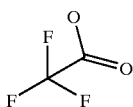 | 465 | 2.69 (5) |
| 78 | 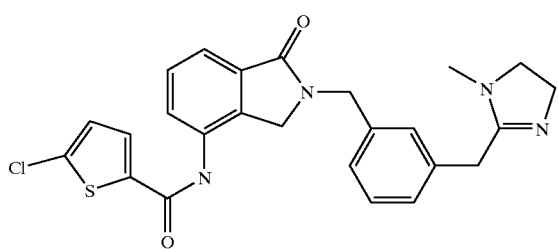<br>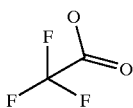 | 479 | 2.72 (5) |

| | | | |
|---|---|---|---|
| 79 | 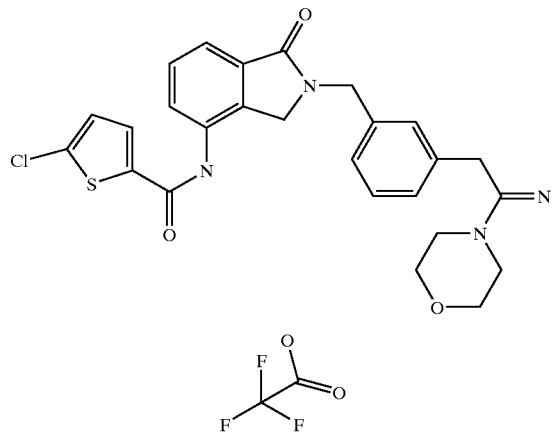 | 509 | 2.73 (5) |
| 80 | 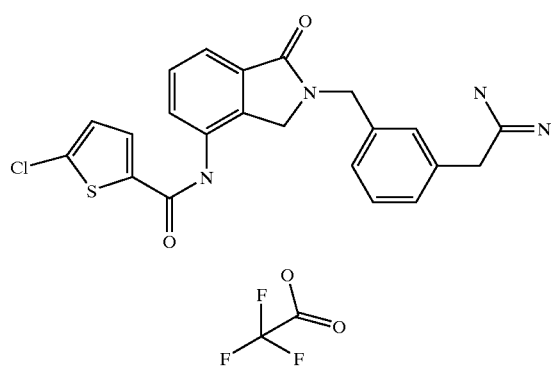 | 439 | 2.67 (5) |
| 81 | 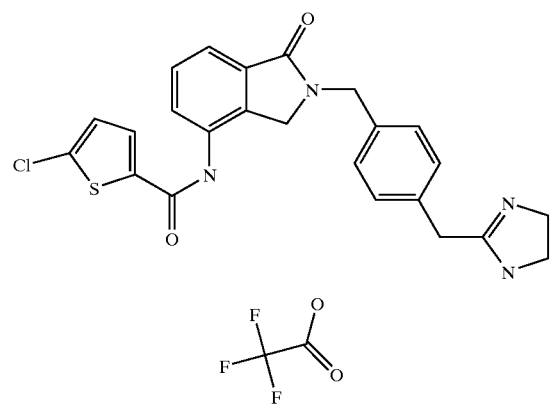 | 465 | 2.66 (5) |
| 82 | 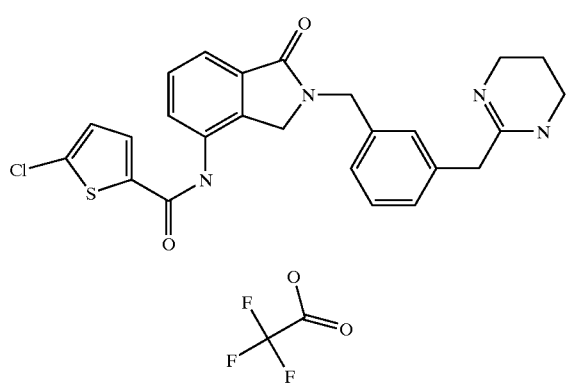 | 479 | 2.74 (5) |

-continued
| | | | |
|---|---|---|---|
| 83 | 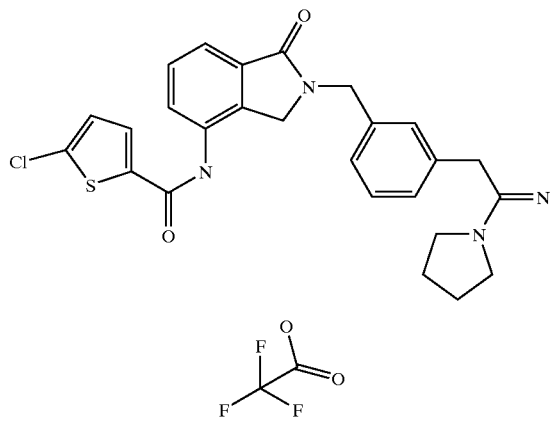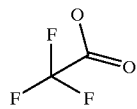 | 493 | 2.85 (5) |
| 84 | 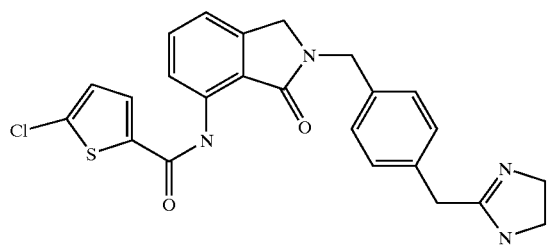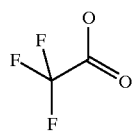 | 465 | 3.09 (5) |
| Example | Structure | m.p. [° C.] or mass spectrum (MS) |
|---|---|---|
| 85 | 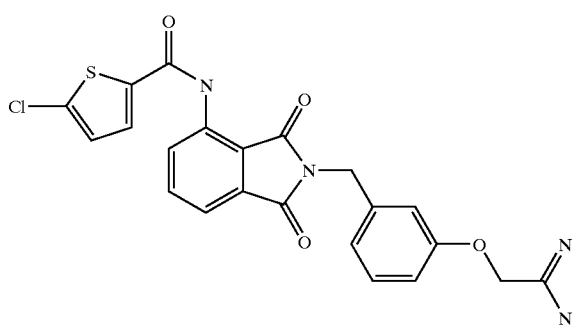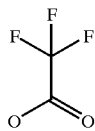 | MS (ESI): 469.0 (M + H), Cl pattern |

| | | |
|---|---|---|
| 86 | 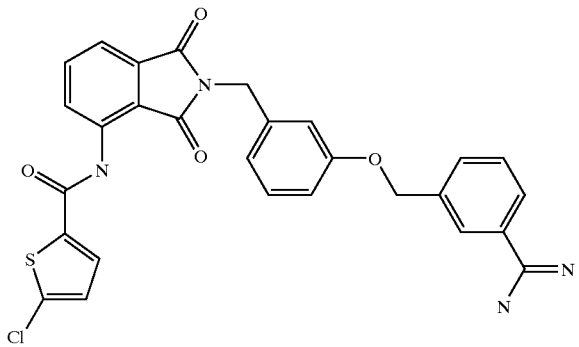 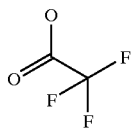 | MS (ESI): 545.2 (M + H), Cl pattern |
| 87 | 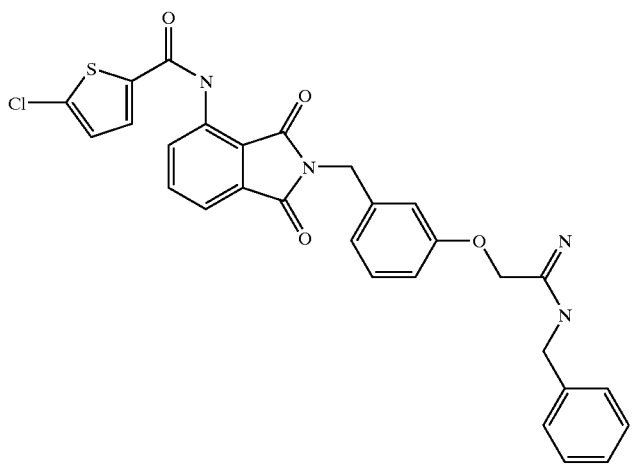 | 180 |
| 88 | 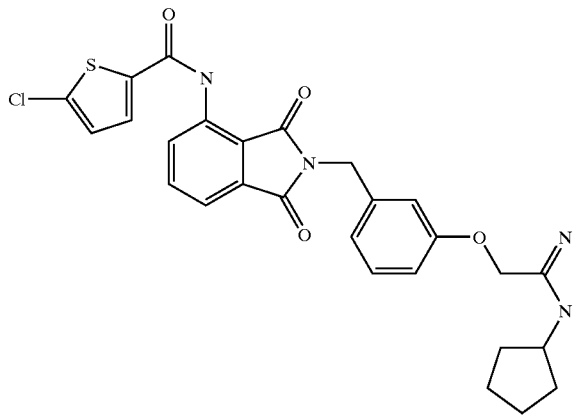 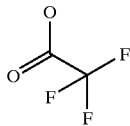 | MS (ESI): 537.1 (M + H), Cl pattern |

| 89 | 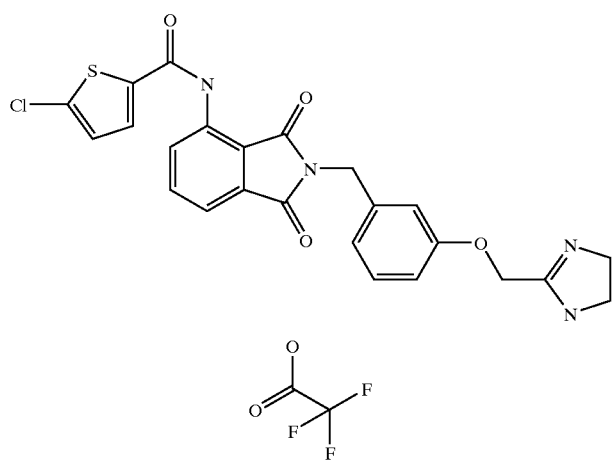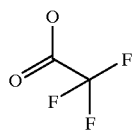 | MS (ESI): 595.0 (M + H), Cl pattern |
| --- | --- | --- |
| 90 | 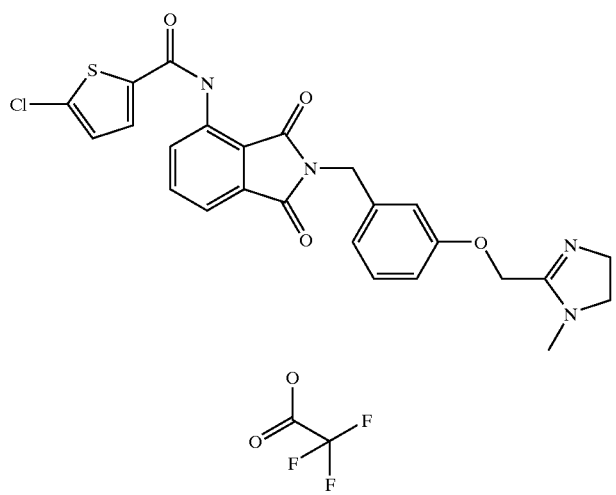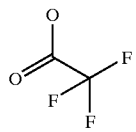 | MS (ESI): 509.1 (M + H), Cl pattern |
| 91 | 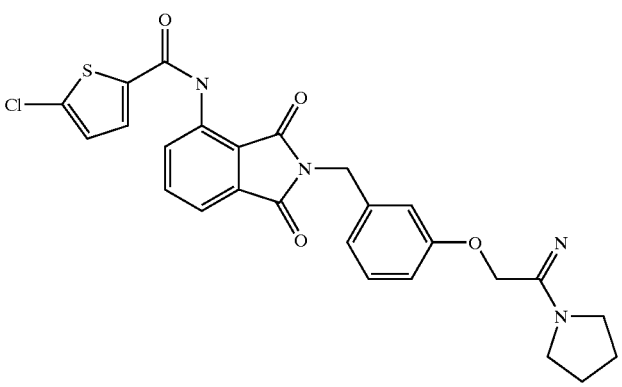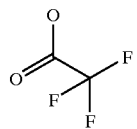 | MS (ESI): 523.0 (M + H), Cl pattern |

-continued
92 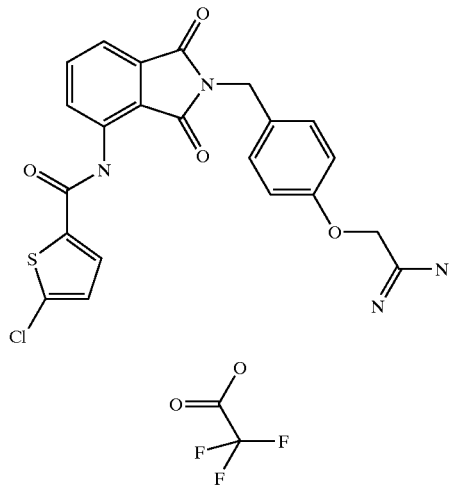 238Z
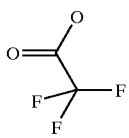
93 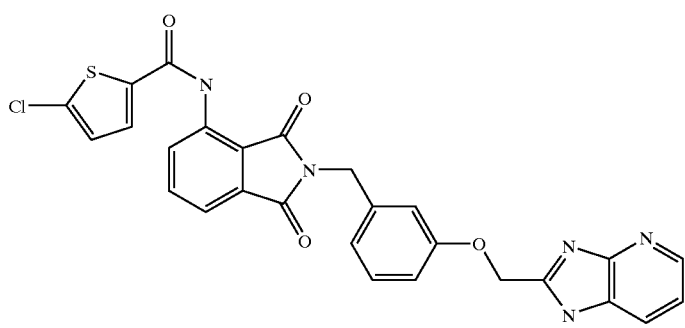 247
94 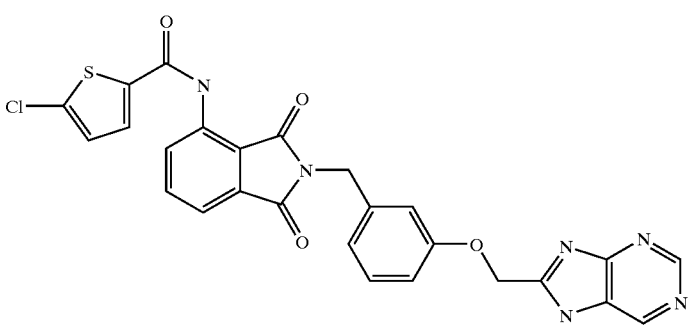 256
95 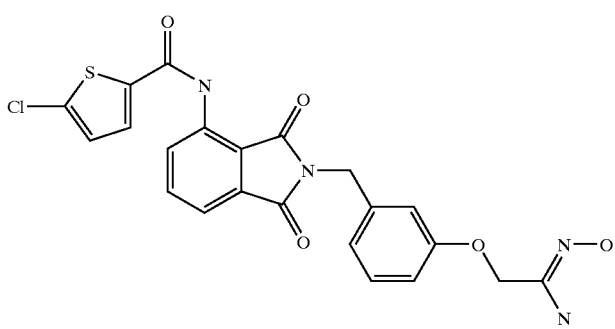 154

| | | |
|---|---|---|
| 96 | 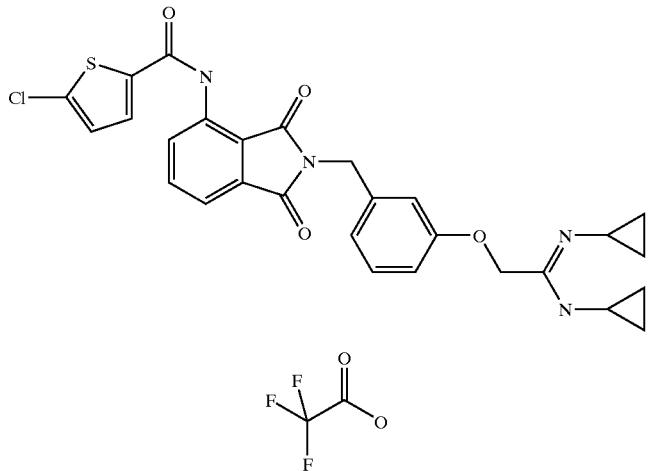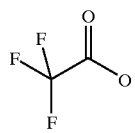 | MS (ESI): 549.0 (M + H), Cl pattern |
| 97 | 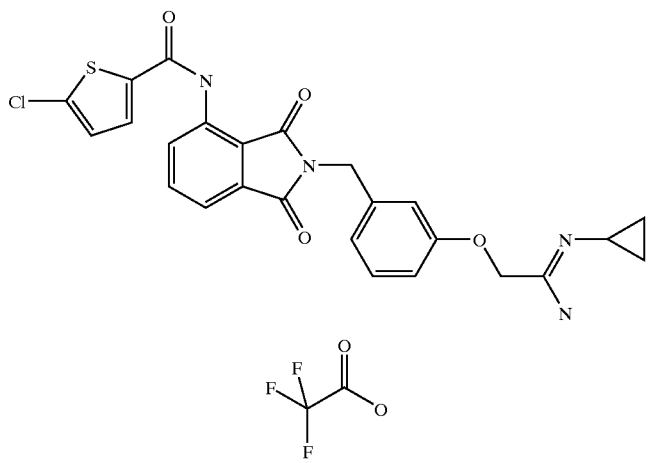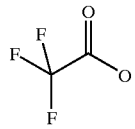 | 1H-NMR (1) |
| 98 | 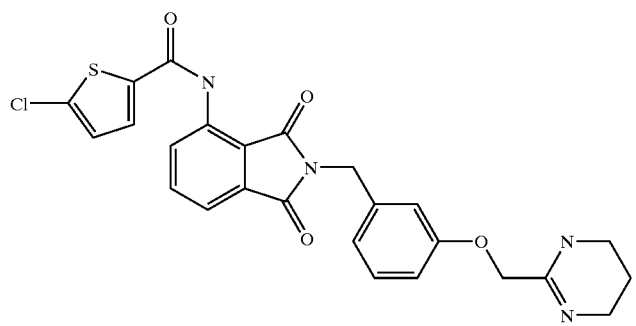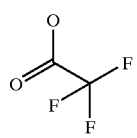 | MS (ESI): 509.1 (M + H), Cl pattern |

| 99 | 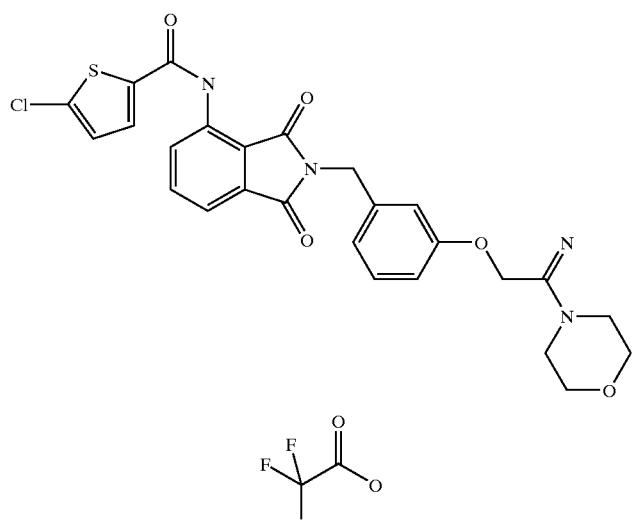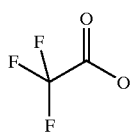 | MS (ESI): 539.2 (M + H), Cl pattern |
| 100 | 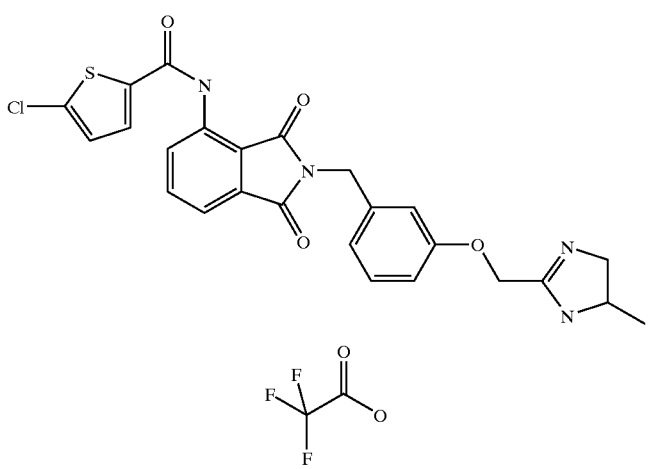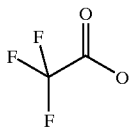 | MS (ESI): 509.1 (M + H), Cl pattern |
| 101 | 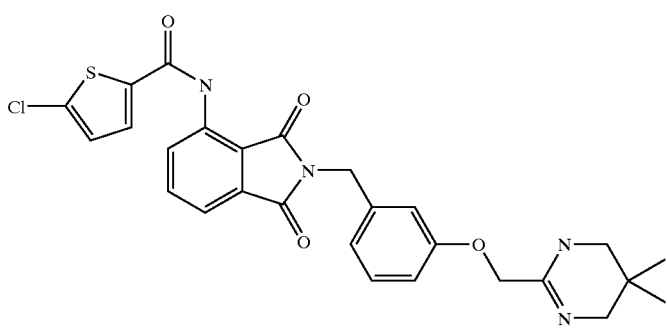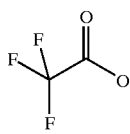 | MS (ESI): 537.3 (M + H), Cl pattern |

| | | |
|---|---|---|
| 102 | 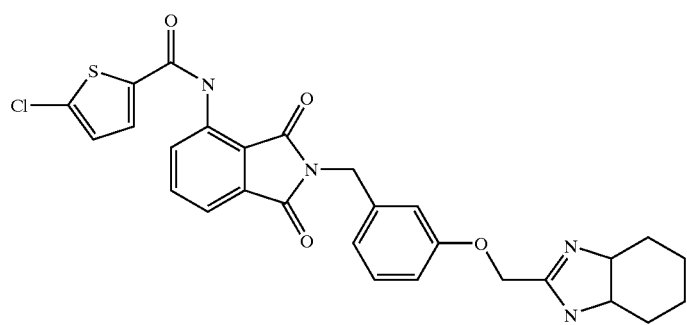 | MS (ESI): 549.2 (M + H), Cl pattern |
| 103 | 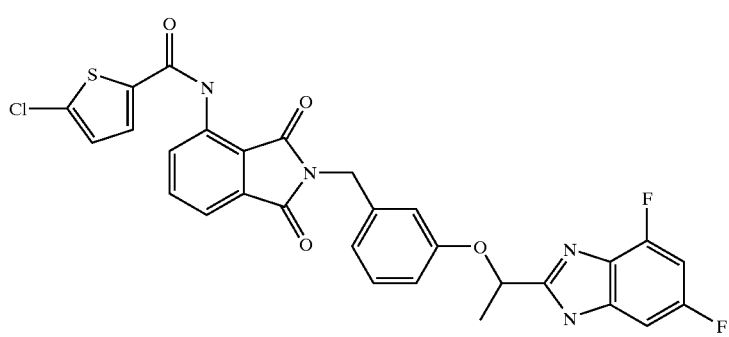 | 219<br>MS (ESI): 512.3 (M + H), Cl pattern |
| 104 | 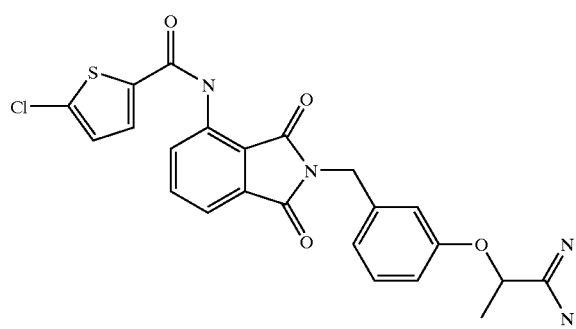<br>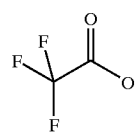 | MS (ESI): 483.2 (M + H), Cl pattern |

-continued
| | | |
|---|---|---|
| 105 | 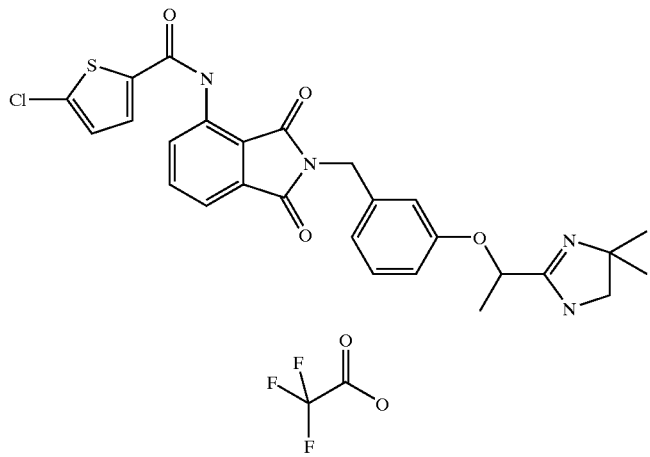 | MS (ESI): 537.3 (M + H), Cl pattern |
| 106 | 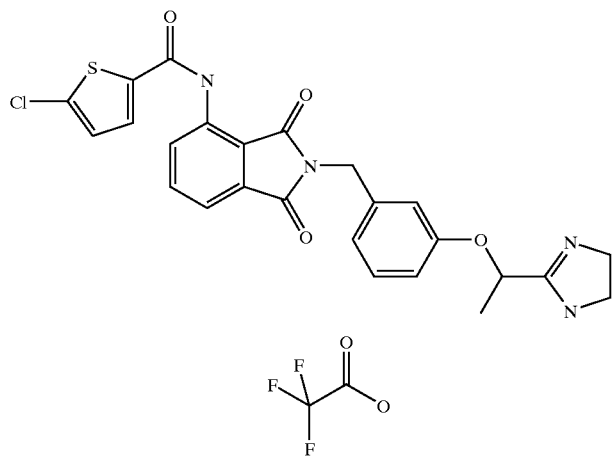 | MS (ESI): 509.2 (M + H), Cl pattern |
| 107 | 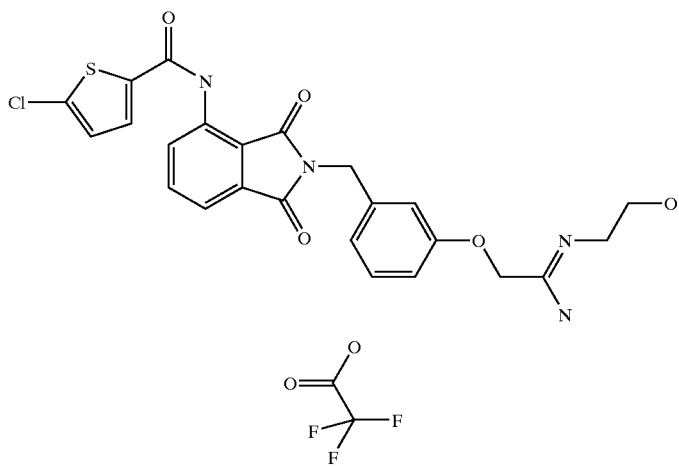 | MS (DCI): 496.4 (M + H), Cl pattern |

(1) $^1$H-NMR (d$^6$-DMSO) 0.6–0.7 (m, 2H), 0.8–0.9 (m, 2H), 2.6–2.7 (m, 1H), 4.8 (s, 2H), 4.85 (s, 2H), 6.85–7.0 (m, 2H), 7.05 (d, 1H), 7.25–7.4 (m, 2H), 7.7 (d, 1H), 7.8 (d, 1H), 7.9 (t, 1H), 8.3 (d, 2H), 9.2 (s, 1H), 9.5 (s, 1H), 9.9 (s, 1H), 10.45 (s, 1H).

Example 108

N-(2-{4-[2-Amino-2-(hydroxyimino)ethyl]benzyl}-1,3-dioxo-2,3-dihydro-1H-isoindol-4-yl)-5-chloro-2-thiophenecarboxamide

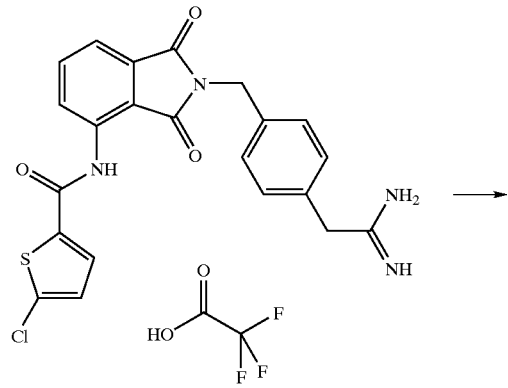

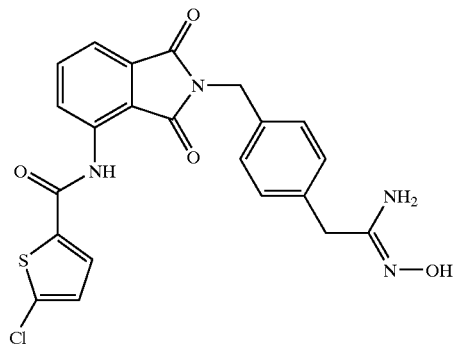

37 mg (0.07 mmol) of N-{2-[4-(2-amino-2-iminoethyl)benzyl]-1,3-dioxo-2,3-dihydro-1H-isoindol-4-yl}-5-chloro-2-thiophenecarboxamide trifluoroacetate are suspended in 3 ml of ethanol, and 0.09 ml (0.65 mmol) of triethylamine and 22.7 mg (0.33 mmol) of hydroxylammonium chloride are added. The reaction mixture is stirred at room temperature for 5 h and then concentrated. The residue is stirred with water and filtered. This gives 21 mg (69% of theory) of the desired product as a solid.

MS=469 (M+H), rt (Method 4)=3.29 min.

Example 109

4-[3-(Hydroxymethyl)phenoxy]-2-pyridinecarboxamide

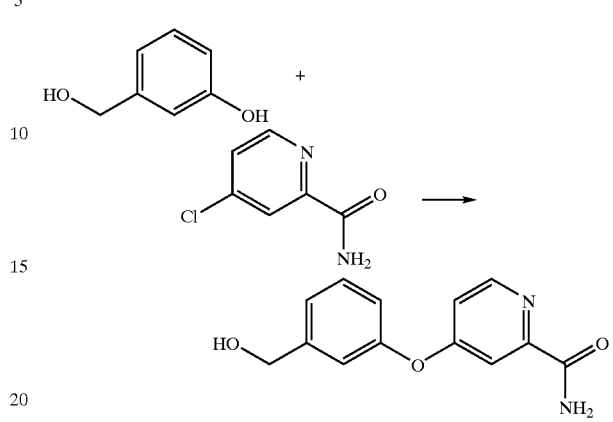

3-Hydroxybenzyl alcohol (7.93 g, 63.8 mmol) is dissolved in 500 ml of DMF, sodium ethoxide (5.22 g, 76.6 mmol) is added, the mixture is stirred with exclusion of moisture for 15 min and 4-chloropyridine-2-carboxamide (D. Varlet et al. *Heterocycles* 2000, 53, 797–804) is then added. The mixture is stirred at 138° C. for 70 hours and again a solution of 4 g of 3-hydroxybenzaldehyde and 2.6 g of sodium ethoxide in 100 ml of DMF, which solution is stirred for 15 min, is added. The mixture is stirred at 138° C. for 12 h and then concentrated under reduced pressure. The residue is transferred into saturated KH$_2$PO$_4$ solution and extracted with ethyl acetate. The organic phase is washed with water. The combined aqueous phases are re-extracted with ethyl acetate. The combined dried organic phases are concentrated under reduced pressure and chromatographed on silica gel using a toluene/ethyl acetate gradient. This gives 5.04 g (32.3% of theory) of the target compound having a m.p. of 113° C. and an R$_f$ (SiO$_2$, ethyl acetate) of 0.49.

Example 110

4-[3-(Hydroxymethyl)phenoxy]-N-methyl-2-pyridinecarboxamide was prepared analogously.

Example 111

4-{3-[(4-{[(5-Chloro-2-thienyl)carbonyl]amino}-1,3-dioxo-1,3-dihydro-2H-isoindol-2-yl)methyl]phenoxy}-2-pyridinecarboxamide

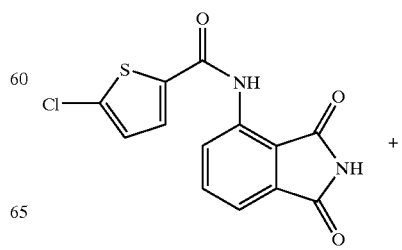

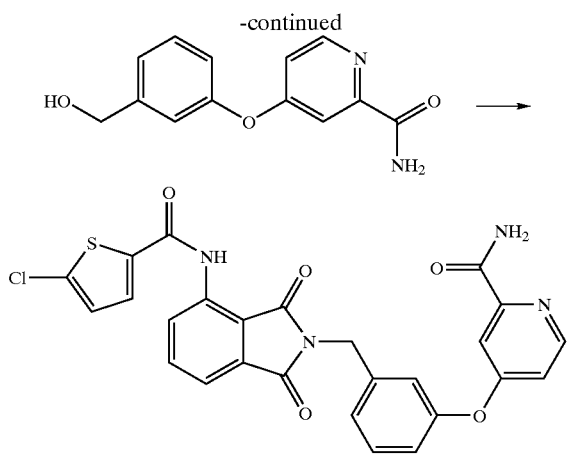

Under argon, triphenylphosphine (0.34 g, 1.3 mmol), 5-chloro-N-(1,3-dioxo-2,3-dihydro-1H-isoindol-4-yl)-2-thiophenecarboxamide (0.2 g, 0.65 mmol) and 4-[3-(hydroxymethyl)phenoxy]-2-pyridinecarboxamide (0.17 g, 0.71 mmol) are initially charged in THF, and diethyl azodicarboxylate (DEAD) (0.2 ml, 1.3 mmol) is added. The mixture is stirred at room temperature for 1 h, 1 g of silica gel is added and the mixture is concentrated under reduced pressure and chromatographed on silica gel using a toluene/ ethyl acetate gradient. The desired fraction is recrystallized from toluene and washed with ether. The crystals contain 2 molar equivalents of diethyl 1,2-hydrazinedicarboxylate.

m.p. 202° C., $R_f$ (toluene/ethyl acetate=1:1)=0.46.

Example 112

4-{3-[(4-{[(5-Chloro-2-thienyl)carbonyl]amino}-1,3-dioxo-1,3-dihydro-2H-isoindol-2-yl)methyl]phenoxy}-N-methyl-2-pyridinecarboxamide trifluoroacetate is obtained analogously following chromatography on Kromasil 100C18 and elution with water/acetonitrile/1 percent strength TFA=24/70/6), in a yield of 27%.

Example 113

After a reaction time of 48 hours, 2-amino-4-[3-(hydroxymethyl)phenoxy]pyridine (prepared by Hoffmann degradation of 4-[3-(hydroxymethyl)phenoxy]-2-pyridinecarboxamide using HOBr) gives, in an analogous manner, N-(2-{3-[(2-amino-4-pyridinyl)oxy]benzyl}-1,3-dioxo-2,3-dihydro-1H-isoindol-4-yl)-5-chloro-2-thiophenecarboxamide

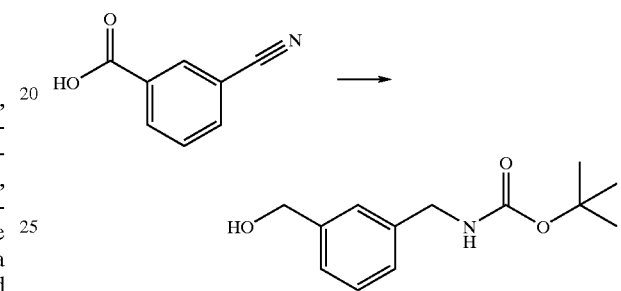

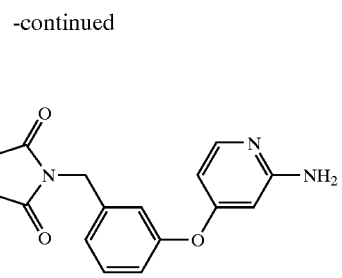

Example 114 tert-Butyl 3-(hydroxymethyl)benzylcarbamate 100 ml of 1N $BH_3$ solution (100 mmol) in THF are slowly added dropwise to an ice-cooled solution of 7.36 g (500 mmol) of 3-cyanobenzoic acid in 100 ml of THF. After 2 h, cooling is removed and the mixture is warmed to room temperature. The suspension is stirred overnight, methanol is then added dropwise and the mixture is concentrated (this operation is repeated twice). The crude product is subjected to column filtration through silica gel (dichloromethane/ methanol/triethylamine 85:10:5). The 3-hydroxymethylbenzylamine thus obtained is dissolved in 150 ml of 1,4-dioxane and cooled to 0° C., and 1.0 eq. of di-tert-butyl dicarbonate (Boc anhydride) and 1.1 eq. of sodium hydroxide in the form of a 1 molar solution are added. Cooling is removed and the mixture is stirred at room temperature for 3 h and then concentrated The residue is taken up in dichloromethane, washed with 1 N hydrochloric acid and sat. sodium chloride solution, dried over magnesium sulfate, concentrated and dried under high vacuum. Yield: 6.27 g (52.8% of theory);

MS (ESI): m/z (%)=260 (M+Na, 17), 164 (100); HPLC (Method 1): rt (%)=6.73 (95).

Analogously, tert-butyl 4-(hydroxymethyl) benzylcarbamate (cf. *J. Chem. Soc. Perkin Trans I*, 1999, 1233) can be obtained by reducing 4-cyanobenzoic acid with $BH_3$ in THF to 4-hydroxymethylbenzylamine, followed by reaction with di-tert-butyl dicarbonate under basic conditions.

Example 115

[4-(2-Bromoethyl)phenyl]methanol (cf. WO 98/43956) is obtained by reduction of 4-(bromomethyl)phenylacetic acid with $BH_3$ in THF.

Example 116 tert-Butyl 4(hydroxymethyl)phenethylcarbamate from benzyl 4-(hydroxymethyl)-phenethylcarbamate (I. Fujii, R. A. Lerner, K. D. Janda, *J. Amer. Chem. Soc.*, 1991, 113, 8528) by catalytical hydrogenation over 10% palladium-on-carbon and subsequent reaction with di-tert-butyl dicarbonate under basic conditions.

Example 117 tert-Butyl 5-bromo-2-fluorobenzylcarbamate is obtained by reaction of 5-bromo-2-fluorobenzylamine (can be obtained according to WO 97/16428) with di-tert-butyl dicarbonate under basic conditions.

Example 118

Trans4-{[(tert-butoxycarbonyl)amino]methyl}cyclohexanecarboxylic acid is obtained from trans-4-(aminomethyl)cyclohexanecarboxylic acid as described in the literature (*J. Med. Chem.*, 1986, 29 4, 448–453).

Example 119 tert-Butyl [4-trans-(hydroxymethyl)cyclohexyl]methylcarbamate

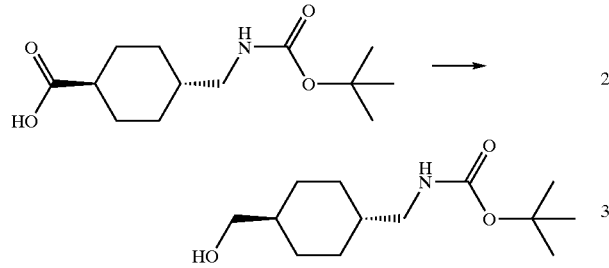

33.5 ml (33.5 mmol) of borane/THF complex are added dropwise as a 1-molar solution in THF to an ice-cooled solution of 8.1 g (33.4 mmol) of trans-4-{[(tert-butoxycarbonyl)amino]methyl}cyclohexanecarboxylic acid in 80 ml of absolute THF. The mixture is warmed to room temperature and stirred for a further 3 h, and methanol is then carefully added dropwise. The mixture is concentrated, the residue is taken up in dichloromethane and the mixture is washed with 1N sodium hydroxide solution, dried over magnesium sulfate and concentrated. Yield 7.21 g (88.6% of theory);

MS (DCI, $NH_4$): m/z (%)=261 (M+$NH_4$, 100).

Example 120 cis-[3-(Hydroxymethyl)cyclohexyl]acetonitrile

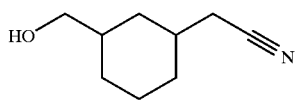

At 0° C., 0.325 ml of methanesulfonic acid (4.2 mmol) is added dropwise to a solution of 600 mg (3.81 mmol) of cis-1,3-bishydroxymethylcyclohexane [*Bioorg. Med. Chem. Lett*, 1996, 1589–1594] and 0.8 ml of triethylamine in 25 ml of absolute dichloromethane. After 15 min at 0° C., the mixture is warmed to room temperature and stirred for 2 h and then concentrated under reduced pressure.

330 mg of the oily residue are dissolved in 3 ml of DMSO, and 106 mg (1.63 mmol) of potassium cyanide are added. The mixture is stirred at 90° C. for 24 h. After cooling, the mixture is diluted with dichloromethane, washed with saturated sodium bicarbonate solution and sodium chloride solution, dried over magnesium sulfate and concentrated. Yield: 207 mg;

GC-MS 10.03 (100) with m/z (%)=171 (M+$NH_4$, 100).

Example 121

N-{2-[3-(Bromomethyl)benzyl]-1,3-dioxo-2,3-dihydro-1H-isoindol-4-yl}-5-chloro-2-thiophenecarboxamide

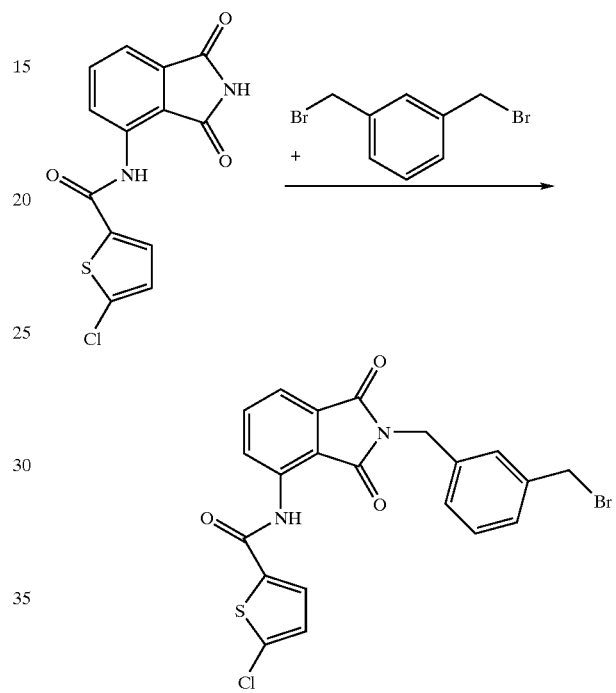

1.31 g (9.5 mmol) of potassium carbonate are added to a suspension of 2.91 g (9.5 mmol) of 5-chloro-N-(1,3-dioxo-2,3-dihydro-1H-isoindol-4-yl)-2-thiophenecarboxamide in 30 ml of DMF. The suspension is stirred vigorously for 30 min, and 8.78 g (33.3 mmol) of α,α-dibromo-m-xylene, dissolved in 20 ml of DMF, are then added in one portion. The suspension is stirred vigorously at room temperature for 5 h and then concentrated under high vacuum. The residue is taken up in dichloromethane, washed with water and sat. sodium chloride solution, dried over magnesium sulfate and concentrated. The crude product is triturated with ether and filtered. The solid is purified further by column filtration through silica gel (dichloromethane). Yield: 2.94 g (63.2% of theory);

MS (EI, pos): m/z (%)=488/490 (M$^+$, 30); HPLC (Method 1): rt (%)=3.62 (100).

General Procedure (I) for Preparing Amino Derivatives by Alkylation of N-{2-[3-(bromomethyl)benzyl]-1,3-dioxo-2,3-dihydro-1H-isoindol-4-yl}-5-chloro-2-thiophenecarboxamide 3 to 5 eq. of amino derivative are added to a solution or suspension of N-{2-[3-(bromomethyl)benzyl]-1,3-dioxo-2,3-dihydro-1H-isoindol-4-yl}-5-chloro-2-thiophenecarboxamide in 1,2-dichloroethane or 1,4-dioxane. The mixture is stirred at room temperature for 2 to 10 h or at 80° C. for 2 to 5 h and then, after cooling to room temperature, diluted with dichloromethane and filtered. The solid is dried under high vacuum. The free amino derivative can be obtained from the resulting hydrobromide of the product: following addition of relatively large amounts of dichloromethane/methanol mixtures, the organic phase is washed with sat. sodium bicarbonate solution, dried over magnesium sulfate and concentrated. The residue is crystallized from dichloromethane/ether mixtures.

Using the general procedure I, the following amino/hydrazine derivatives can be obtained from N-{2-[3-(bromomethyl)benzyl]-1,3-dioxo-2,3-dihydro-1H-isoindol-4-yl}-5-chloro-2-thiophenecarboxamide:

| Example | Structure | Mass spectrum | LC/HPLC Method |
|---|---|---|---|
| 122 | 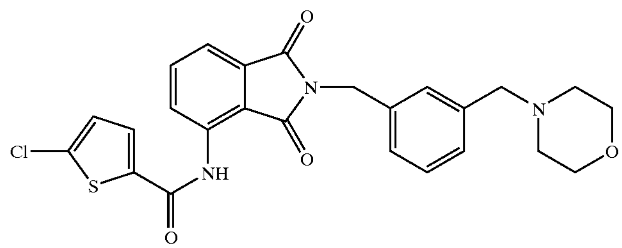 | 496 (100, M + H) ESI | 7.19 (98) Method 2 |
| 123 | 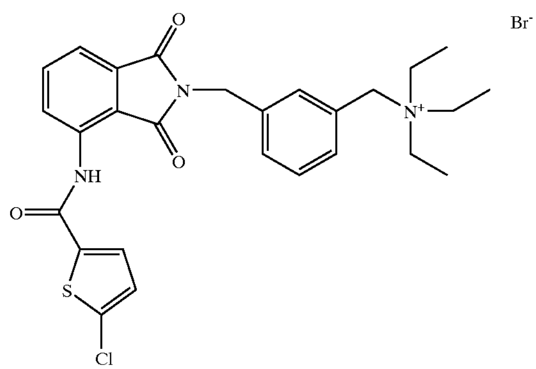 | 510 (100, M − Br) ESI | 8.19 (84) Method 1 |
| 124 | 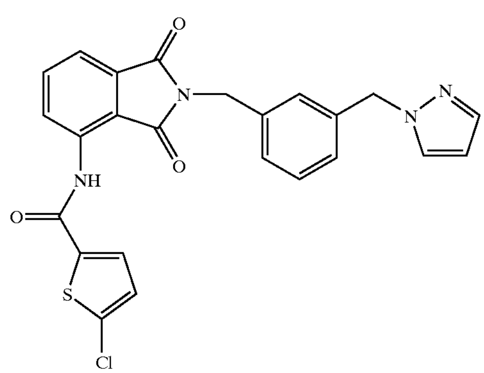 | 477 (100, M + H) ESI | 10.31 (94) Method 2 |
| 125 | 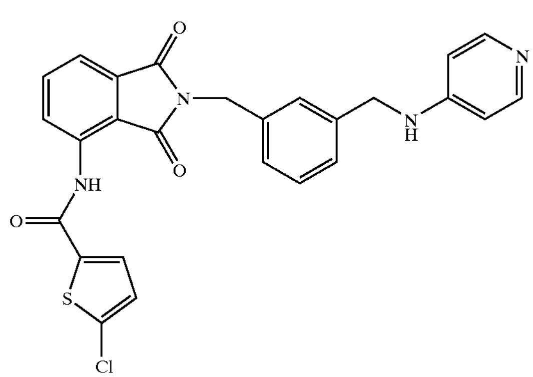 | 503 (100, M + H) ESI | 4.73 (94) Method 1 |

-continued

| Example | Structure | Mass spectrum | LC/HPLC Method |
|---|---|---|---|
| 126 | 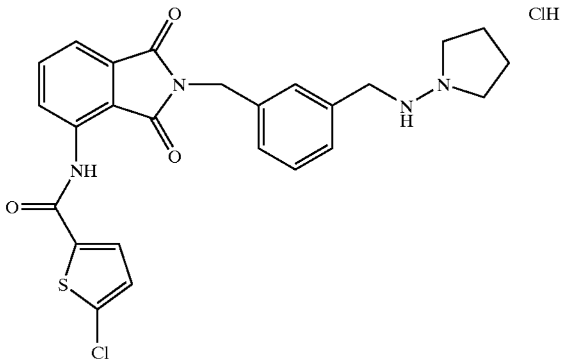 | 495 LC/MS | 3.24 (95) LC/MS Method 7 |
| 127 | 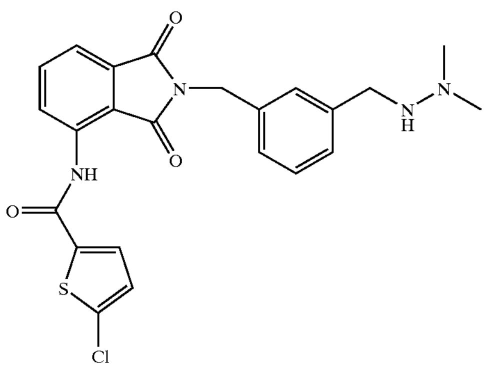 | 469 LC/MS | 3.18 (97) LC/MS Method 7 |
| 128 | 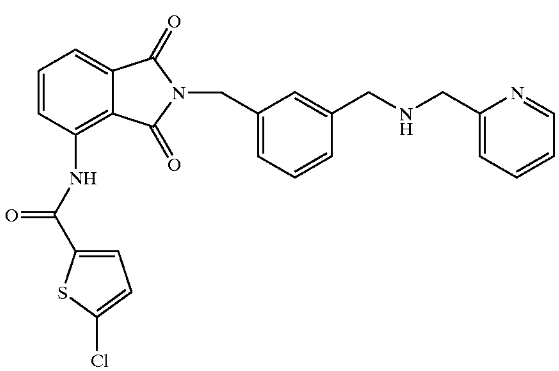 | 517 LC/MS | 3.35 (81) LC/MS Method 7 |
| 129 | 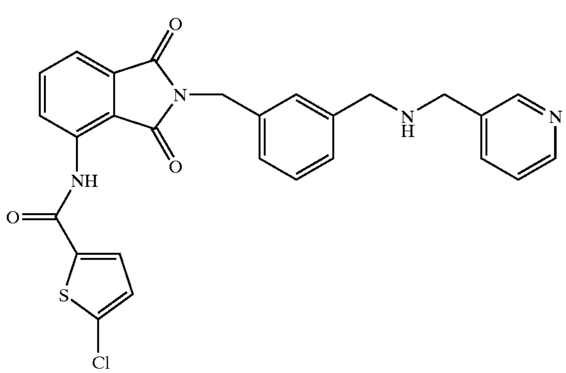 | 517 LC/MS | 3.15 (91) LC/MS Method 7 |

-continued

| Example | Structure | | Mass spectrum | LC/HPLC Method |
|---|---|---|---|---|
| 130 | 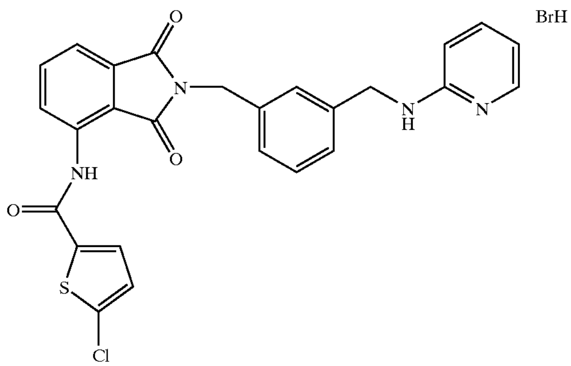 | BrH | 503 (100, M + H) ESI | 3.30 (100) LC/MS Method 7 |
| 131 | 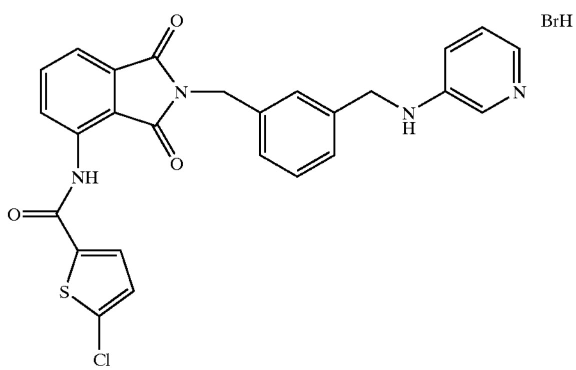 | BrH | 503 (100, M + H) ESI | 7.79 (95) LC/MS Method 7 |
| 132 | 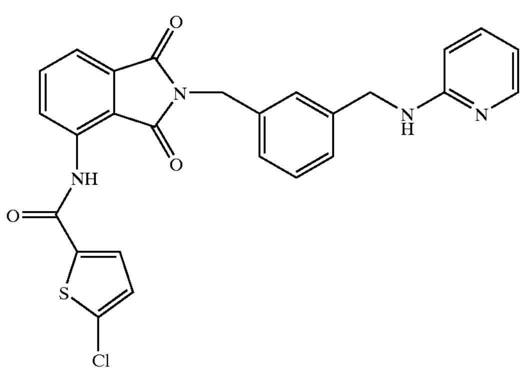 | | 503 (M + H) LC-MS | 3.35 (90) LC-MS Method 4 |
| 133 | 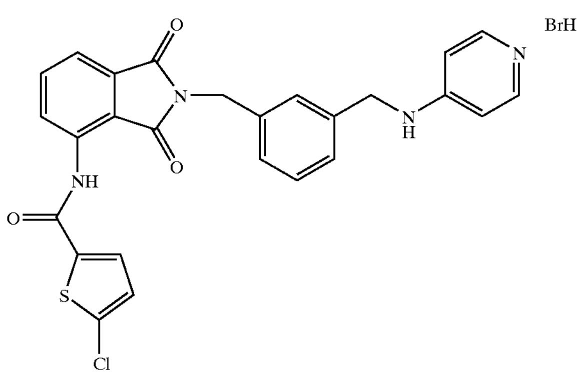 | BrH | 503 (100, M + H) ESI | 7.84 (98) Method 2 |

Example 134 tert-Butyl 3-[(4-{[[(5-chloro-2-thienyl)carbonyl]amino}-1,3-dioxo-1,3-dihydro-2H-isoindol-2-yl)methyl]benzylcarbamate

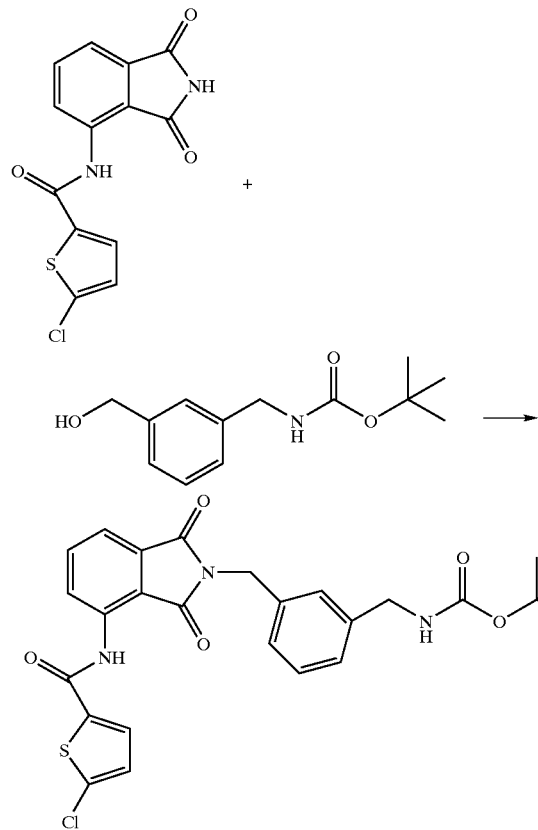

2.41 ml (15.4 mmol) of diethyl azodicarboxylate (DEAD) are added dropwise to a mixture, cooled with water, of 3.37 g (11 mmol) of 5-chloro-N-(1,3-dioxo-2,3-dihydro-1H-isoindol-4-yl)-2-thiophenecarboxamide, 3.26 g (13.8 mmol) of tert-butyl 3-(hydroxymethyl)benzylcarbamate and 4.04 g (15.4 mmol) of triphenylphosphine in 60 ml of absolute THF. The reaction mixture is stirred vigorously at room temperature for 90 min and then concentrated to a volume of about 30 ml. 300 ml of ether are added to the solid and the mixture is filtered. Another crystallization of the mother liquor yields a second batch. The product is dried under high vacuum. Alternatively, the product can be purified by column chromatography on silica gel (dichloromethane/methanol mixture or cyclohexane/ethyl acetate mixture). Yield: 4.79 g (82.8% of theory);

MS (ESI): m/z (%)=526 (M+H, 20); HPLC (Method 1): rt (%)=9.69 (98.6).

In an analogous manner, the following compounds can be obtained from 5-chloro-N-(1,3-dioxo-2,3-dihydro-1H-isoindol-4-yl)-2-thiophenecarboxamide and the corresponding alcohols:

Example 135

N-[2-(3-Aminobenzyl)-1,3-dioxo-2,3-dihydro-1H-isoindol-4-yl]-5-chloro-2-thiophenecarboxamide MS (DCI, NH$_3$): m/z (%)=429 (M+NH$_4$, 100), 412 (M+H, 20); HPLC (Method 1): rt (%)=7.88 (97.3).

Example 136

N-{2-[4-(Bromomethyl)phenethyl]-1,3-dioxo-2,3-dihydro-1H-isoindol-4-yl}-5-chloro-2-thiophenecarboxamide MS (DCI, NH$_3$): m/z (%)=519/522 (M+NH$_4$, 40), 442 (40),); HPLC (Method 1): rt (%)=8.85 (42), 10.19 (42).

Example 137 tert-Butyl {4-trans-[(4-{[[(5-chloro-2-thienyl)carbonyl]amino}-1,3-dioxo-1,3-dihydro-2H-isoindol-2-yl)methyl]cyclohexyl}methylcarbamate MS (ESI neg): m/z (%)=530 ([M–H]$^-$, 100); HPLC (Method 1): rt (%)=5.85 (98).

Example 138

5-Chloro-N-(2-{[cis-3-(cyanomethyl)cyclohexyl]methyl}-1,3-dioxo-2,3-dihydro-1H-isoindol-4-yl)-2-thiophenecarboxamide MS (DCI, NH$_4$): m/z (%)=464 (M+Na, 42), 442 (M+H, 40); HPLC (Method 2): rt (%)=5.49 (100).

Example 139

5-Chloro-N-(1,3-dioxo-2-{4-[(4-pyridinylamiino)methyl]phenethyl}-2,3-dihydro-1H-isoindol-4-yl)-2-thiophenecarboxamide

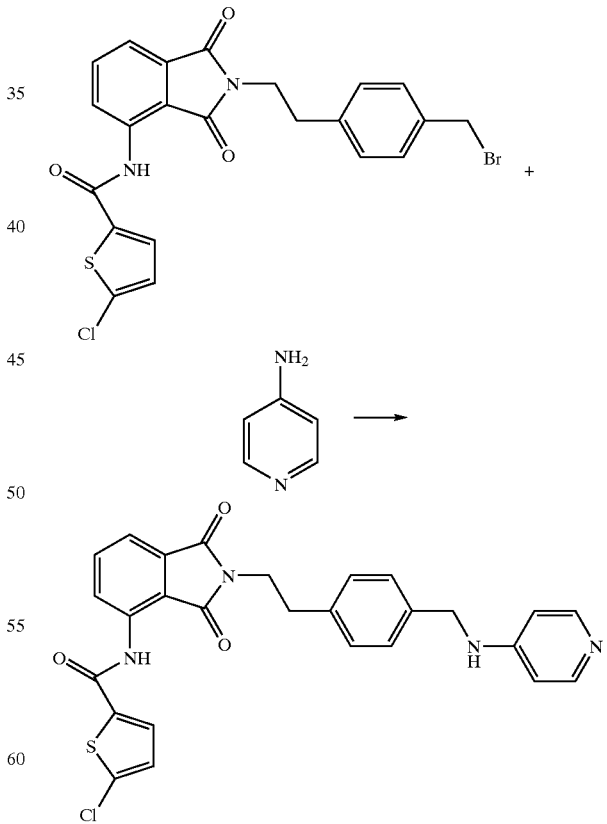

50 mg (0.1 mmol) of N-{2-[4-(bromomethyl)phenethyl]-1,3-dioxo-2,3-dihydro-1H-isoindol-4-yl}-5-chloro-2-thiophenecarboxamide are introduced a little at a time into a solution of 37.4 mg (0.4 mmol) of 4-aminopyridine in 4 ml 1,2-dichloroethane. The mixture is stirred at room temperature overnight and then diluted with dichloromethane/methanol (98:2), washed with sat. sodium bicarbonate solution, dried over magnesium sulfate and concentrated. The residue is crystallized using dichloromethane/ether and the solid is filtered off with suction and dried under high vacuum. Yield: 25.1 mg (37.2% of theory); MS (ESI): m/z (%)=517 (M+H, 100);); LC-MS (Method 7): rt (%)=3.42 (77).

Example 140

N-{2-[3-(Aminomethyl)benzyl]-1,3-dioxo-2,3-dihydro-1H-isoindol-4-yl}-5-chloro-2-thiophenecarboxamide

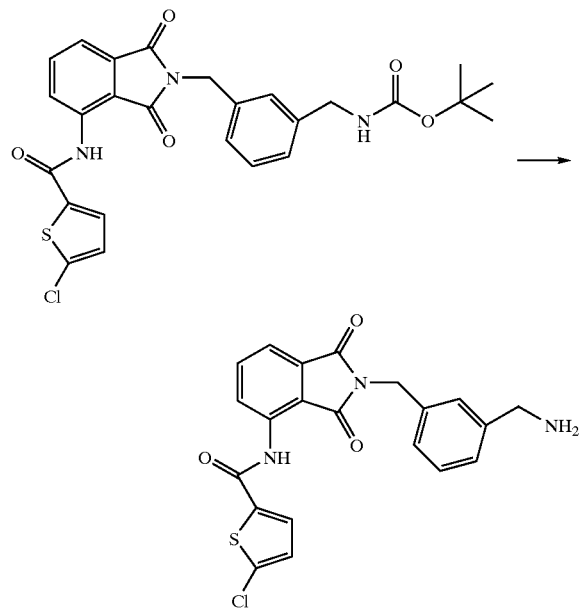

40 ml of a mixture of TFA and water (9:1) are added dropwise to an ice-cooled mixture of 3.95 g (7.5 mmol) of tert-butyl 3-[(4-{[(5-chloro-2-thienyl)carbonyl]amino}-1,3-dioxo-1,3-dihydro-2H-isoindol-2-yl)methyl]benzylcarbamate in 40 ml of chloroform. Ice-cooling is removed and the solution is stirred at room temperature for 2 h and then concentrated. The residue is taken up in dichloromethane/methanol (98:2) and the mixture is washed with sat. sodium bicarbonate solution, dried over magnesium sulfate and concentrated. Yield: 3.22 g (97.8% of theory);

MS (ESI): m/z (%)=426 (M+H, 95), 409 (100); HPLC (Method 1): rt (%)=7.98 (98.1).

The following compounds can be obtained in an analogous manner from the corresponding Boc-protected precursors:

Example 141

N-{2-[4-(Aminomethyl)benzyl]-1,3-dioxo-2,3-dihydro-1H-isoindol-4-yl}-5-chloro-2-thiophenecarboxamide MS (DCI, NH$_3$): m/z (%)=426 (M+H, 100); HPLC (Method 1): rt (%)=8.05 (98.3).

Example 142

N-{2-[4-(2-Aminoethyl)benzyl]-1,3-dioxo-2,3-dihydro-1H-isoindol-4-yl}-5-chloro-2-thiophenecarboxamide MS (ESI): m/z (%)=440 (M+H, 100); HPLC (Method 1): rt (%)=4.60 (94.2).

Example 143

N-[2-(3-{[(Aminocarbonyl)amino]methyl}benzyl)-1,3-dioxo-2,3-dihydro-1H-isoindol-4-yl]-5-chloro-2-thiophenecarboxamide

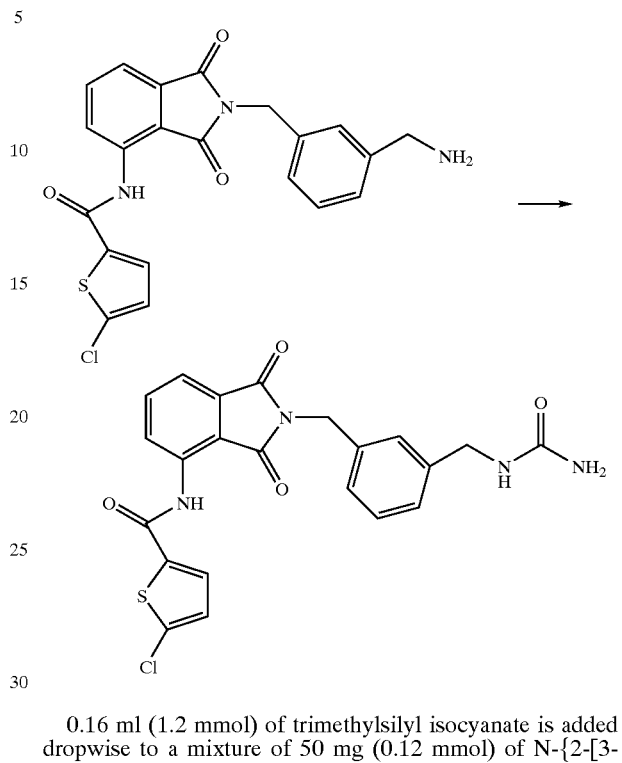

0.16 ml (1.2 mmol) of trimethylsilyl isocyanate is added dropwise to a mixture of 50 mg (0.12 mmol) of N-{2-[3-(aminomethyl)benzyl]-1,3-dioxo-2,3-dihydro-1H-isoindol-4-yl}-5-chloro-2-thiophenecarboxamide in 2 ml of dry dichloromethane. The suspension is stirred at room temperature overnight and then concentrated and dried under high vacuum. Ether is added to the residue and the product is obtained as a solid by filtration. Yield: 50 mg (90.8% of theory);

MS (DCI, NH$_3$): m/z (%)=469 (M+H, 33); 426 (100); HPLC (Method 1): rt (%)=8.50 (95.8).

The following compounds can be obtained in an analogous method from the corresponding amino derivatives using trimethyl isocyanate:

Example 144

N-[2-(4-{[(Aminocarbonyl)amino]methyl}benzyl)-1,3-dioxo-2,3-dihydro-1H-isoindol-4-yl]-5-chloro-2-thiophenecarboxamide MS (DCI, NH$_3$): m/z (%)=486 (M+NH$_4$, 100), 426 (95); HPLC (Method 1): rt (%)=8.51 (98.5).

Example 145

N-[2-(4-{2-[(Aminocarbonyl)amino]ethyl}benzyl)-1,3-dioxo-2,3-dihydro-1H-isoindol-4-yl]-5-chloro-2-thiophenecarboxamide MS (DCI, NH$_3$): m/z (%)=483 (M+H, 83), 440 (100); HPLC (Method 1): rt (%)=4.76 (98.8).

General Procedure (II-a) for Preparing Urea Derivatives from N-{2-[3-(aminomethyl)benzyl]-1,3-dioxo-2,3-dihydro-1H-isoindol-4-yl}-5-chloro-2-thiophenecarboxamide and isocyanates A solution of 1 eq. of amino derivative in absolute dichloromethane (about 0.05 mol/l) is, at room temperature, added dropwise to a solution of 2 to 3 eq. of isocyanate in absolute dichloromethane (about 0.4 mol/l). The mixture is stirred at room temperature for 30 min to 14 h and then diluted with dichloromethane/ether mixtures. The crystal slurry is filtered off with suction and dried under high vacuum. If required, the product is re-purified by crystallization from dichloromethane/ether or column filtration through silica gel (dichloromethane/methanol mixtures).

| Example | Structure | Mass spectrum | LC Method |
|---|---|---|---|
| 146 | 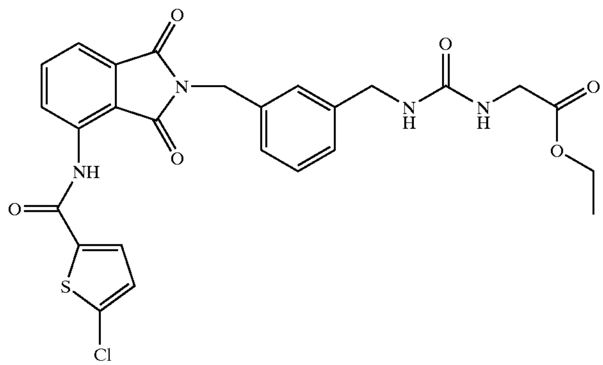 | 554 LC/MS | 4.62 (94) LC/MS Method 5 |
| 147 | 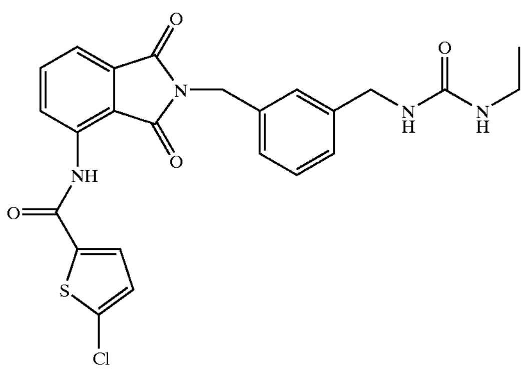 | 496 LC/MS | 4.54 (95) LC/MS Method 5 |

General Procedure (II-b) for Preparing Urea Derivatives from N-[2-(3-aminobenzyl)-1,3-dioxo-2,3-dihydro-1H-isoindol-4-yl]-5-chloro-2-thiophene-carboxamide and isocyanates 3 to 15 eq. of isocyanate are added to a suspension of the aniline in absolute dichloromethane. The mixture is stirred at room temperature for 14 to 48 h and then, after addition of ether, filtered. The crude product is purified by crystallization with dichloromethane/ether mixtures or by preparative thin-layer chromatography (dichloromethane/methanol mixtures).

| Example | Structure | Mass spectrum | LC (Method) |
|---|---|---|---|
| 148 | 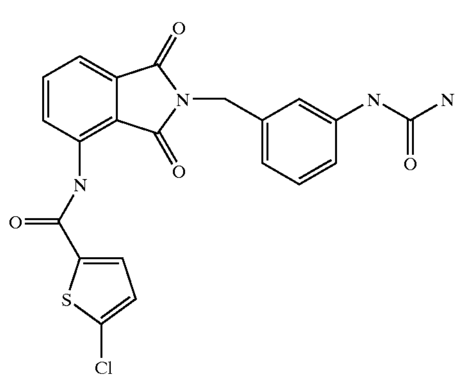 | 453 (100, M − H) ESI neg. | 8.89 (97) Method 2 |

Example 149

5-Chloro-N-{2-[3-(isocyanatomethyl)benzyl]-1,3-dioxo-2,3-dihydro-1H-isoindol-4-yl}-2-thiophenecarboxamide

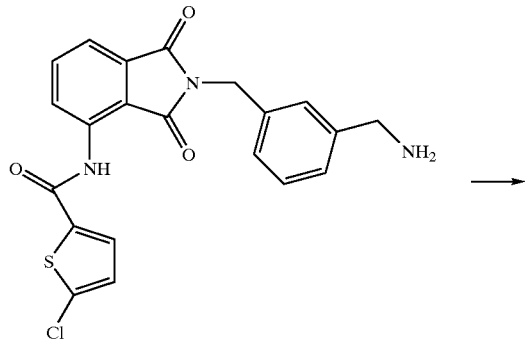

A solution of 430 mg (1.0 mmol) of N-{2-[3-(aminomethyl)benzyl]-1,3-dioxo-2,3-dihydro-1H-isoindol-4-yl}-5-chloro-2-thiophenecarboxamide and 433 mg (2.0 mmol) of 1,8-bis-(dimethylamino)naphthalene in 222 ml of dichloromethane is added dropwise to an ice-cooled solution of 0.12 ml (0.96 mmol) of diphosgene in 7.5 ml of dichloromethane. After 5 min at 0° C., the mixture is warmed to room temperature and stirred for 35 min, and 40 ml of ether are then added. Insoluble particles are filtered off and the filtrate is concentrated and dried under high vacuum. The resulting solid is immediately reacted further, without further purification. Yield: 454 mg (99.5% of theory).

Example 150

The following compound can be obtained in an analogous manner from N-{2-[4-(aminomethyl)benzyl]-1,3-dioxo-2,3-dihydro-1H-isoindol-4-yl}-5-chloro-2-thiophenecarboxamide:

5-Chloro-N-{2-[4-(isocyanatomethyl)benzyl]-1,3-dioxo-2,3-dihydro-1H-isoindol-4-yl}-2-thiophenecarboxamide MS (DCI, $NH_3$): m/z (%)=469 (M+$NH_4$, 30).

General Procedure (III-a) for Preparing Urea Derivatives from 5-chloro-N-{2-[3-(isocyanatomethyl)benzyl]-1,3-dioxo-2,3-dihydro-1H-isoindol-4-yl}-2-thiophenecarboxamide A solution of the isocyanate (1 eq.) in a mixture of absolute dichloromethane and DMF is added dropwise to a solution of 2 to 5 eq. of the corresponding amino or hydrazine derivative in absolute dichloromethane. If the amino or hydrazine derivative is present as a hydrochloride, an additional about 5 eq. of triethylamine are added. The mixture is stirred at room temperature for about 16 h. After addition of dichloromethane/ether mixtures, the crude product is obtained as a solid by filtration. The crude product is purified by crystallization with dichloromethane/ether mixtures or by chromatography on silica gel (dichloromethane/methanol mixtures).

| Example | Structure | Mass spectrum | LC/HPLC Method |
|---|---|---|---|
| 151 | 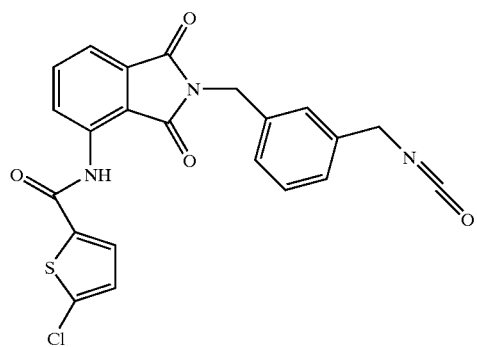 | 538 (65, M + H) DCI | 9.15 (96) Method 2 |

-continued

| Example | Structure | Mass spectrum | LC/HPLC Method |
|---|---|---|---|
| 152 | 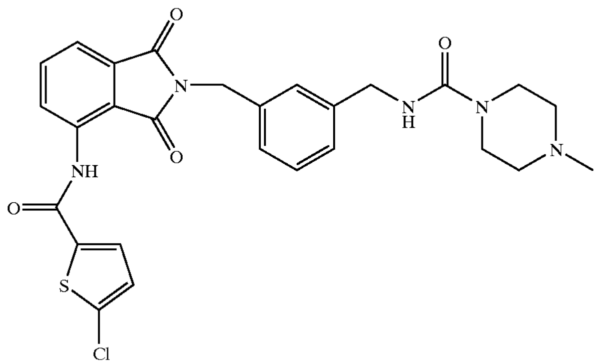 | 552 (100, M + H) ESI | 7.45 (100) Method 2 |
| 153 | 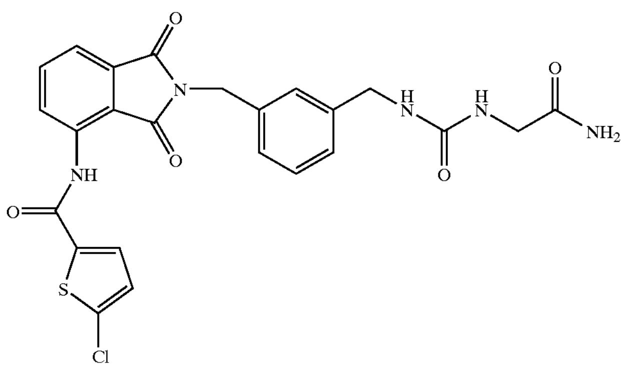 | 525 LC/MS | 4.06 (100) LC/MS Method 5 |
| 154 | 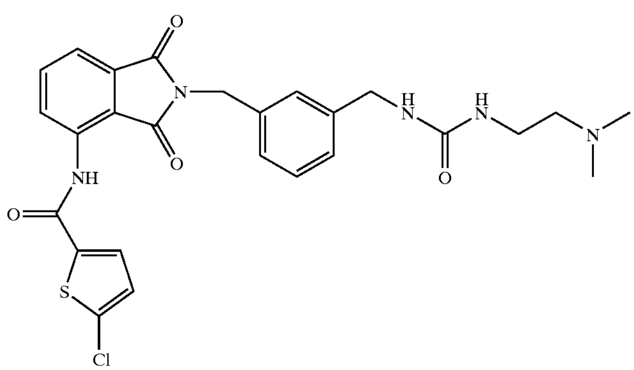 | 539 LC/MS | 3.27 (100) LC/MS Method 5 |
| 155 | 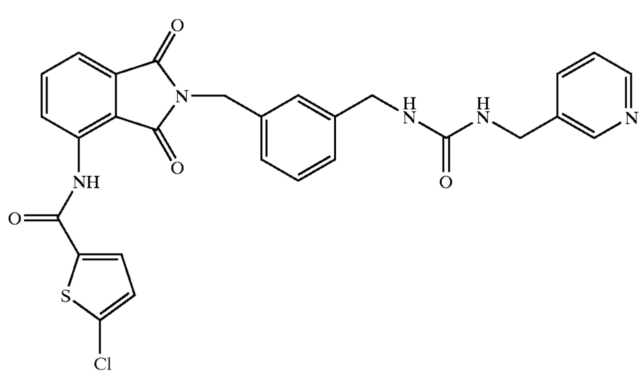 | 559 LC/MS | 3.45 (100) LC/MS Method 5 |

| Example | Structure | Mass spectrum | LC/HPLC Method |
|---------|-----------|---------------|----------------|
| 156 | 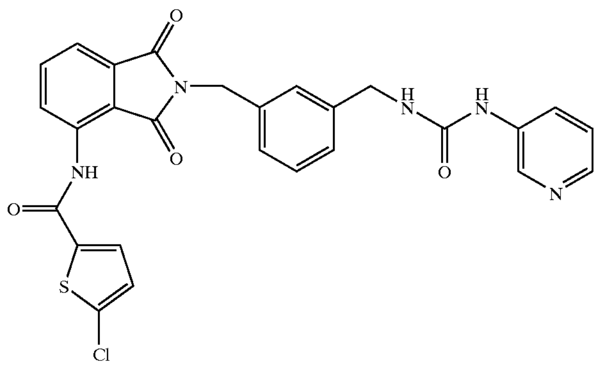 | 545 LC/MS | 3.54 (100) LC/MS Method 5 |
| 157 | 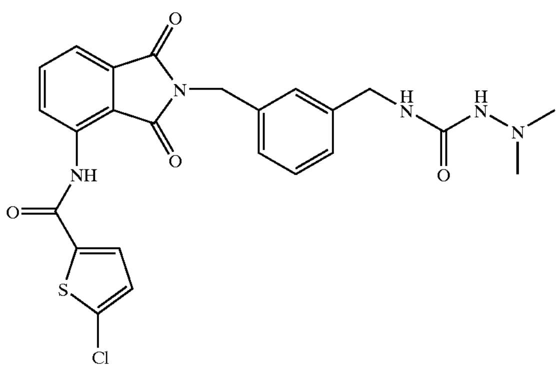 | 512 LC/MS | 4.59 (100) LC/MS Method 7 |
| 158 | 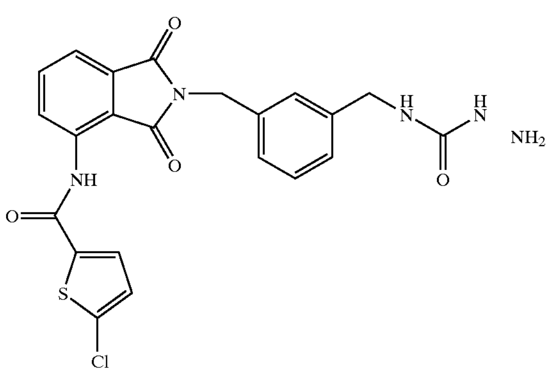 | 483 LC/MS | 3.88 (87) LC/MS Method 7 |

General Procedure (III-b) for Preparing Urea Derivatives from 5-chloro-N-{2-[4-(isocyanatomethyl)benzyl]-1,3-dioxo-2,3-dihydro-1H-isoindol-4-yl}-2-thiophenecarboxamide A solution of the isocyanate (1 eq.) in a mixture of absolute dichloromethane and DMF is added dropwise to a solution of 2 to 5 eq. of the corresponding amino or hydrazine derivative in absolute dichloromethane. If the amino or hydrazine derivative is present as a hydrochloride, an additional about 5 eq. of triethylamine are added. The mixture is stirred at room temperature for about 16 h. After addition of dichloromethane/ether mixtures, the product is obtained as a solid by filtration and dried under high vacuum. If appropriate, the product is purified further by crystallization with dichloromethane/ether mixtures or by chromatography on silica gel (dichloromethane/methanol mixtures).

| Example | Structure | Mass spectrum | LC Method |
|---|---|---|---|
| 159 | 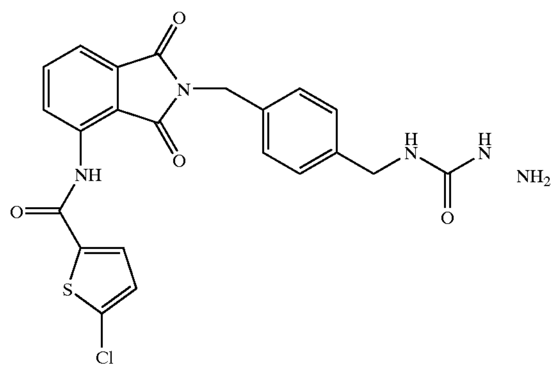 | 484 LC/MS | |
| 160 | 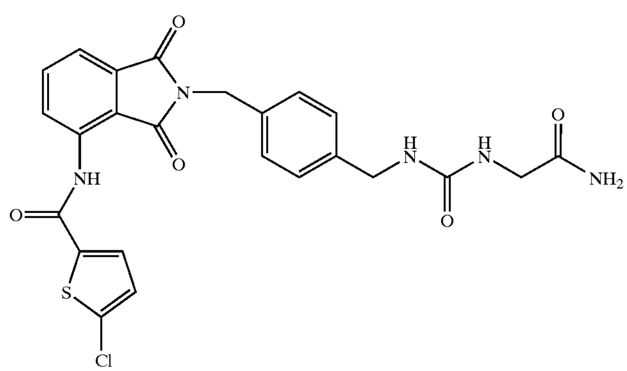 | 525 LC/MS | 4.09 (100) LC/MS Method 6 |
| 161 | 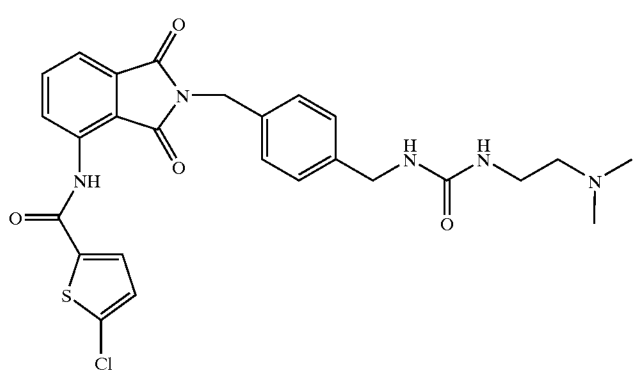 | 540 LC/MS | 5.60 (98) LC/MS Method 6 |

Example 162

N-(2-{4-[2-(Acetylamino)ethyl]benzyl}-1,3-dioxo-2,3-dihydro-1H-isoindol-4-yl)-5-chloro-2-thiophenecarboxamide

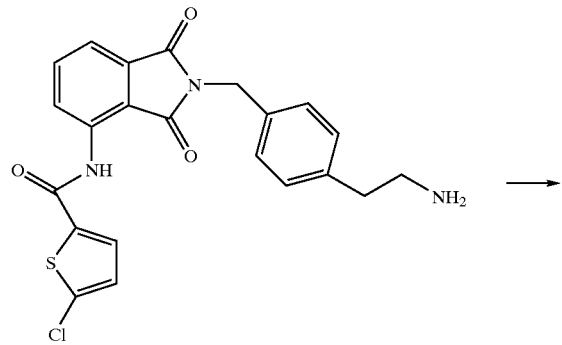

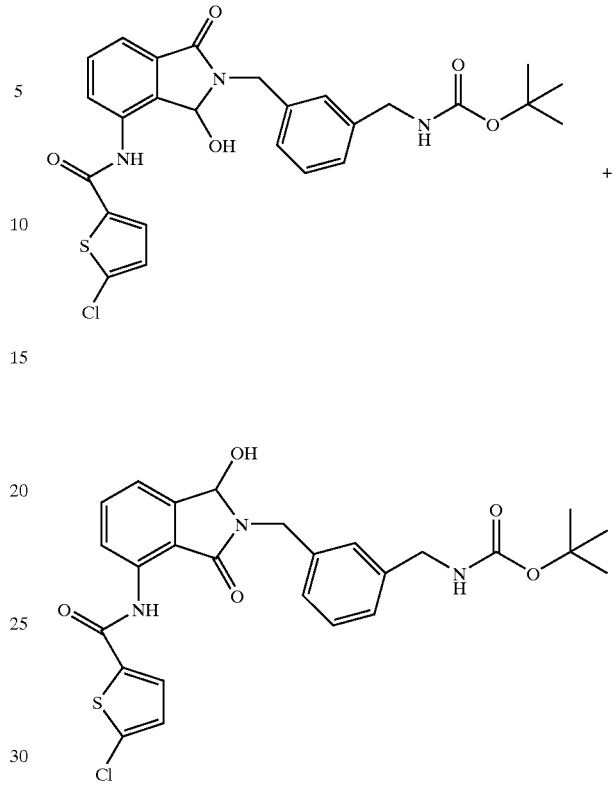

0.04 ml (0.46 mmol) of pyridine and 0.02 ml (0.18 mmol) of acetic anhydride are added dropwise to a solution of 40 mg (0.09 mmol) of N-{2-[4-(2-aminoethyl)benzyl]-1,3-dioxo-2,3-dihydro-1H-isoindol-4-yl}-5-chloro-2-thiophenecarboxamide in 2 ml of absolute THF. After 2 h at room temperature, the solution is concentrated and the residue is taken up in ethyl acetate. The mixture is washed twice with water, dried over magnesium sulfate, concentrated and dried under high vacuum. Yield: 35.2 mg (80.3% of theory);

MS (DCI, $NH_3$): m/z (%)=499 (M+$NH_4$, 100); HPLC (Method 1): rt (%)=490 (100).

Example 163 tert-Butyl 3-[(4-{[(5-chloro-2-thienyl)carbonyl]amino}-3-hydroxy-1-oxo-1,3-dihydro-2H-isoindol-2-yl)methyl]benzylcarbamate and tert-butyl 3-[(4-{[(5-chloro-2-thienyl)carbonyl]amino}-1-hydroxy-3-oxo-1,3-dihydro-2H-isoindol-2-yl)methyl]benzylcarbamate

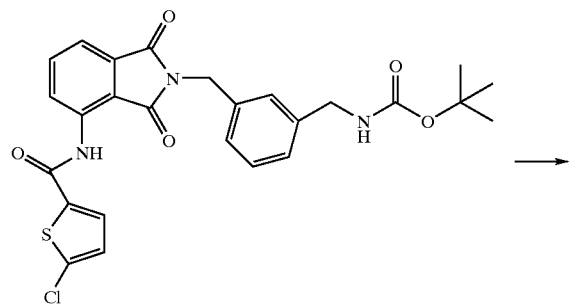

A little at a time, 55 mg (1.41 mmol) of sodium borohydride are added to a solution of 620 mg (1.18 mmol) of tert-butyl 3-[(4-{[(5-chloro-2-thienyl)carbonyl]amino}-1,3-dioxo-1,3-dihydro-2H-isoindol-2-yl)methyl]benzylcarbamate in 25 ml of methanol and 25 ml of dichloromethane. The solution is stirred at room temperature for 3 h and then, carefully, acidified slightly with 1N hydrochloric acid solution. Water is added and the mixture is extracted twice with dichloromethane. The combined organic phases are dried with magnesium sulfate and concentrated. The product mixture is separated by column chromatography on silica gel (dichloromethane/methanol 98:2). The isomeric products are assigned by high-resolution NMR spectroscopy. The following compounds are obtained:

220 mg of tert-butyl 3-[(4-{[(5-chloro-2-thienyl)carbonyl]amino}-3-hydroxy-1-oxo-1,3-dihydro-2H-isoindol-2-yl)methyl]benzylcarbamate (purity 66%, 23.2% of theory). MS (LC-MS): m/z (%)=510 (M–$H_2O$, 100); HPLC (Method 1): rt (%)=8.45 (66%).

300 mg of tert-butyl 3-[(4-{[(5-chloro-2-thienyl)carbonyl]amino}-1-hydroxy-3-oxo-1,3-dihydro-2H-isoindol-2-yl)methyl]benzylcarbamate (45.9% of theory). MS (LC-MS m/z (%)=510 (M–$H_2O$, 100); HPLC (Method 1): rt (%)=9.09 (95).

Example 164

N-{2-[3-(Aminomethyl)benzyl]-1-oxo-2,3-dihydro-1H-isoindol-4-yl}-5-chloro-2-thiophenecarboxamide

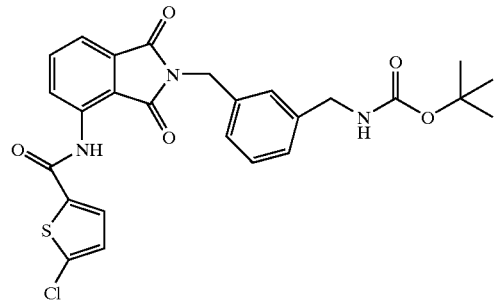

Example 166

N-[2-(3-{[(Aminocarbonyl)amino]methyl}benzyl)-1-oxo-2,3-dihydro-1H-isoindol-4-yl]-5-chloro-2-thiophenecarboxamide

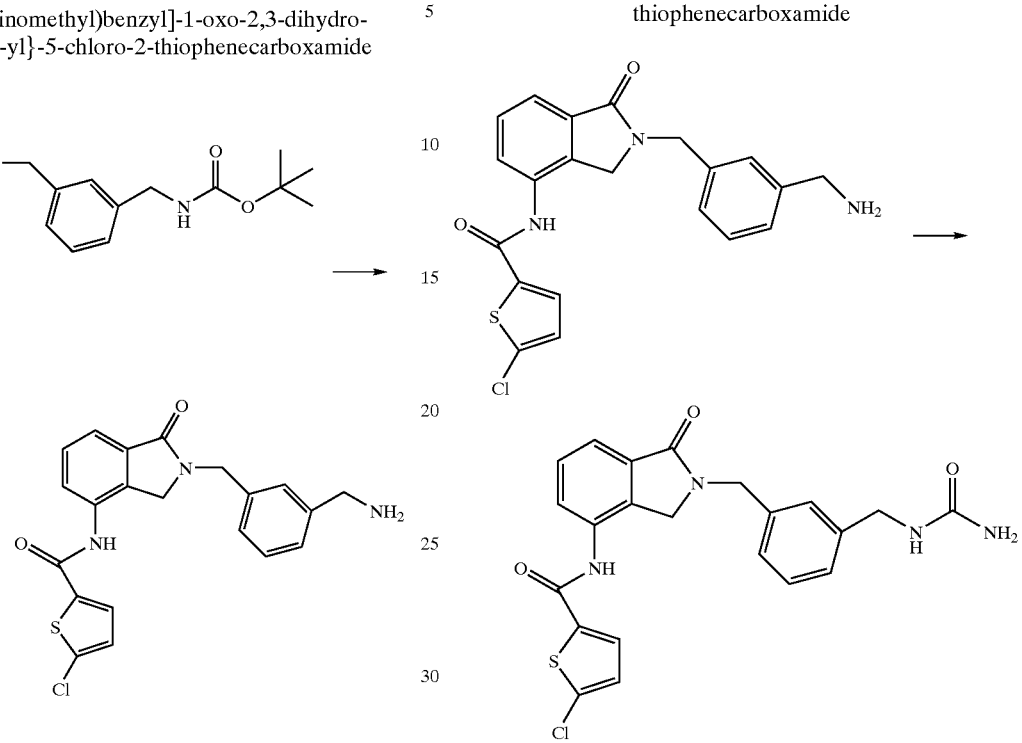

0.21 ml (2.7 mmol) of TFA and 0.07 ml (0.45 mmol) of triethylsilane are added dropwise to a solution of 181 mg (purity 66%, 0.22 mmol) of tert-butyl 3-[(4-{[(5-chloro-2-thienyl)carbonyl]amino}-3-hydroxy-1-oxo-1,3-dihydro-2H-isoindol-2-yl)methyl]benzylcarbamate in 4.5 ml of dichloromethane. The solution is stirred at room temperature overnight and then concentrated and dried under high vacuum. The residue is taken up in dichloromethane/methanol and the mixture is washed with 1N sodium hydroxide solution, dried over magnesium sulfate and concentrated. Ether is added to the residue, the mixture is filtered off with suction and the product is dried under high vacuum. Yield: 84 mg (90.7% of theory); MS (DCI, $NH_3$): m/z (%)=412 (M+H, 100); HPLC (Method 2): rt (%)=6.25 (80).

Example 165

In an analogous manner, N-{2-[3-(aminomethyl)benzyl]-3-oxo-2,3-dihydro-1H-isoindol-4-yl}-5-chloro-2-thiophenecarboxamide can be prepared from tert-butyl 3-[(4-{[(5-chloro-2-thienyl)carbonyl]amino}-1-hydroxy-3-oxo-1,3-dihydro-2H-isoindol-2-yl)methyl]benzylcarbamate.

MS (ESI): m/z (%)=412 (M+H, 100); HPLC (Method 2): rt (%)=7.17 (87).

0.08 ml (0.61 mmol) of trimethylsilyl isocyanate is added dropwise to a solution of 50 mg (0.12 mmol) of N-{2-[3-(aminomethyl)benzyl]-1-oxo-2,3-dihydro-1H-isoindol-4-yl}-5-chloro-2-thiophenecarboxamide in 2 ml of absolute dichloromethane. The mixture is stirred at room temperature overnight, and ether is then added. The solid is filtered off with suction, washed with ether and dried under high vacuum. Yield: 44.6 mg (64.6% of theory);

MS (DCI, $NH_3$): m/z (%)=427 (M+$NH_4$, 53), 412 (100); HPLC (Method 2): rt (%)=7.13 (80).

Example 167

In an analogous manner, N-[2-(3-{[(aminocarbonyl)amino]methyl}benzyl)-3-oxo-2,3-dihydro-1H-isoindol-4-yl]-5-chloro-2-thiophenecarboxamide can be prepared from N-{2-[3-(aminomethyl)benzyl]-3-oxo-2,3-dihydro-1H-isoindol-4-yl}-5-chloro-2-thiophenecarboxamide.

MS (DCI, $NH_3$): m/z (%)=472 (M+$NH_4$, 100) 455 (M+H, 80); HPLC (Method 2): rt (%)=8.52 (85).

General Procedure (IV-a) for Reducing Phthalimides to Substituted 5-chloro-N-(3-hydroxy-1-oxo-2,3-dihydro-1H-isoindol-4-yl)-2-thiophenecarboxamide Derivatives and the Regioisomeric 5-chloro-N-(1-hydroxy-3-oxo-2,3-dihydro-1H-isoindol-4-yl)-2-thiophenecarboxamide Derivatives At 0° C., sodium borohydride (1.5 to 2.5 eq.) is added, a little at a time, to a suspension of appropriately substituted phthalimide (1 eq.) in a mixture of methanol and dichloromethane (1:1). After the addition has ended, the mixture is stirred at room temperature for 1.5 to 3 h and then acidified slightly with 1N hydrochloric acid solution and diluted with dichloromethane. The mixture is washed with sat. sodium bicarbonate solution and sat. sodium chloride solution, dried over magnesium sulfate and concentrated. The product mixture can be separated and purified either by column chromatography on silica gel (dichloromethane/methanol mixtures) or by preparative RP-HPLC. On prolonged contact of hydroxyoxo-2,3-dihydro-1H-isoindol-4-yl derivatives with methanol and silica gel, a reaction giving the corresponding methoxy-substituted derivatives may take place.

| Example | Structure | Mass spectrum | LC/HPLC Method |
|---|---|---|---|
| 168 | 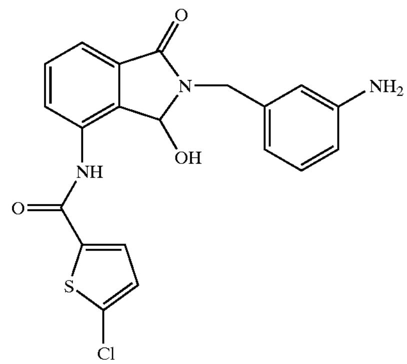 | 395 (M − H₂O, 100) ESI | 7.22 (90.6) Method 1 |
| 169 | 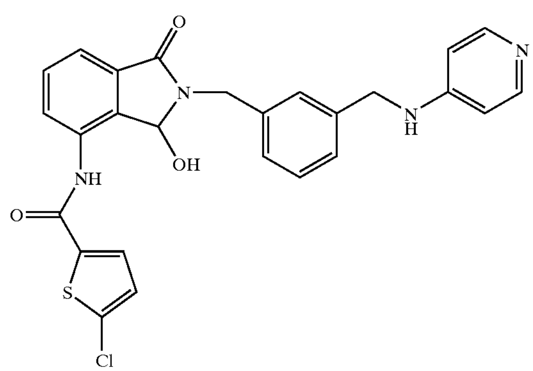 | 505 (M + H, 100) ESI | 4.18 (98) Method 1 |
| 170 | 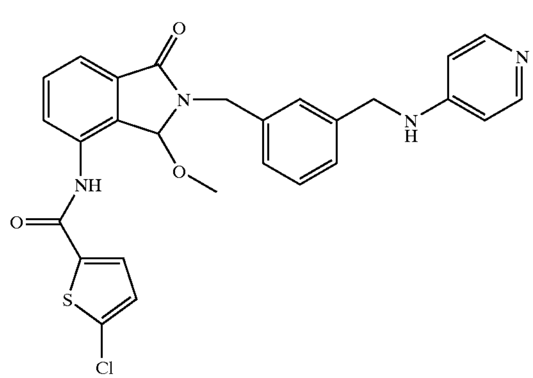 | 519 (M + H, 100), 487 (50) ESI | 4.33 (70) Method 1 |

-continued

| Example | Structure | Mass spectrum | LC/HPLC Method |
|---|---|---|---|
| 171 | 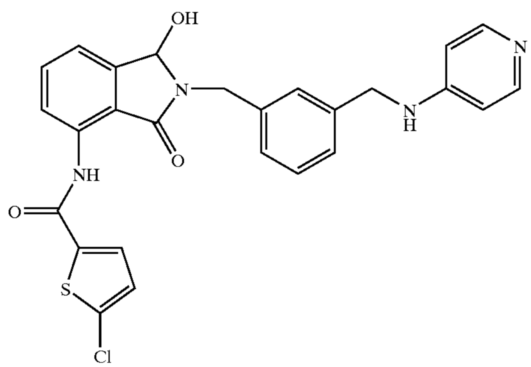 | 505 (M + H, 100) ESI | 4.47 (98.5) Method 1 |
| 172 | 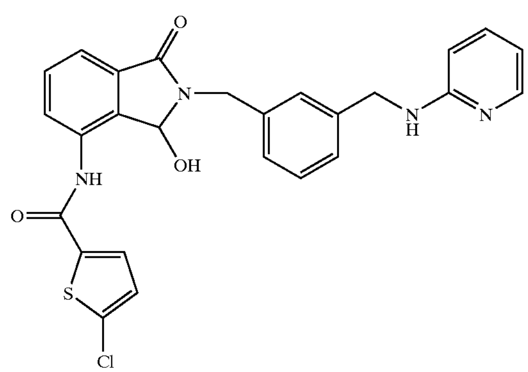 | 505 (M + H, 100) ESI | |
| 173 | 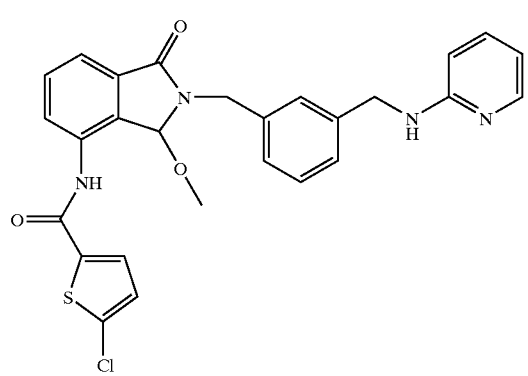 | 519 (M + H, 100) ESI | |
| 174 | 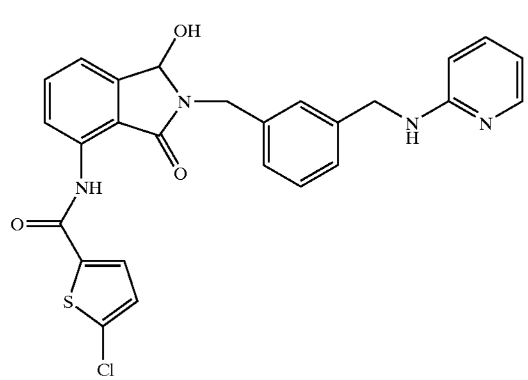 | 505 (M + H, 100) DCI | 8.10 (96.1) Method 1 |

| Example | Structure | Mass spectrum | LC/HPLC Method |
|---|---|---|---|
| 175 | 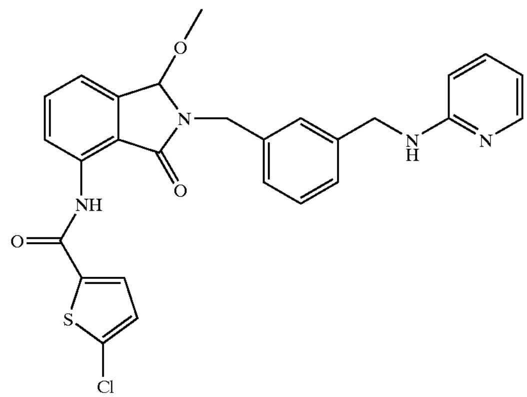 | 519 (M + H, 100) ESI | |
| 176 | 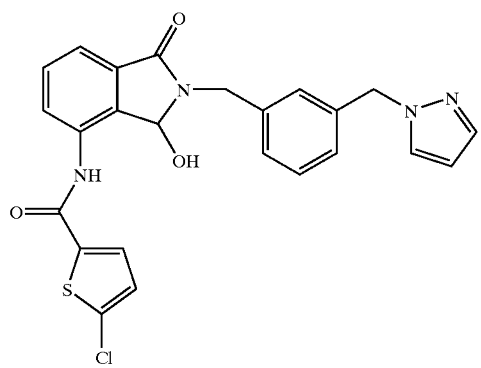 | 478 (M + H, 100) DCI | 4.26 (100) Method 2 |
| 177 | 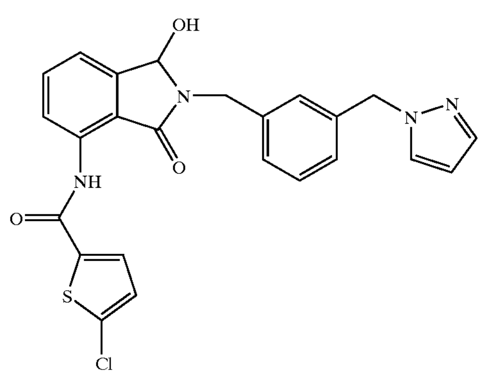 | 478/478 (M +H, 100) DCI | 4.76 (96.7) Method 2 |

General Procedure (IV-b) for Preparing Substituted 5-chloro-N-(1-oxo-2,3-dihydro-1H-isoindol-4-yl)-2-thiophenecarboxamide Derivatives and the Regioisomeric 5-chloro-N-(3-oxo-2,3-dihydro-1H-isoindol-4-yl)-2-thiophenecarboxamide Derivatives from the Corresponding hydroxy-oxo-2,3-dihydro-1H-isoindol-4-yl Derivatives At room temperature, TFA (about 12 eq.) and triethylsilane (1.5 to 2 eq.) are added dropwise to a solution of a hydroxyoxo-2,3-dihydro-1H-isoindol-4-yl derivative in dichloromethane (about 0.1 mol/l). The mixture is stirred at room temperature for 3 to 16 h and then concentrated to dryness. The residue is taken up in dichloromethane and the mixture is washed with sat. sodium bicarbonate solution or 1N sodium hydroxide solution, dried over magnesium sulfate and concentrated. If desired, the product can be purified either by crystallization with ether/dichloromethane mixtures or by chromatography on silica gel (dichloromethane/methanol mixtures).

| Example | Structure | Mass spectrum | LC/HPLC Method |
|---------|-----------|---------------|----------------|
| 178 | 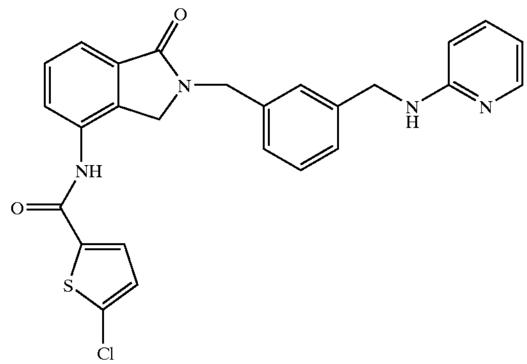 | 489 (100, M + H) ESI | 4.33 (95) Method 1 |
| 179 | 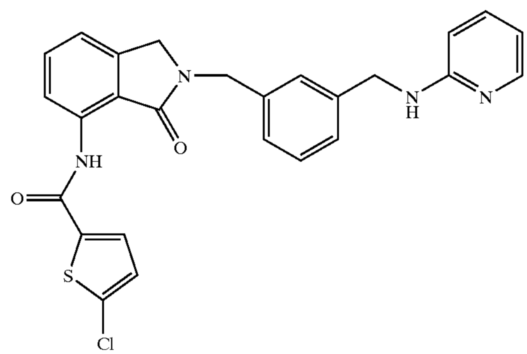 | 489 (100, M + H) ESI | 4.78 (91) Method 1 |
| 180 | 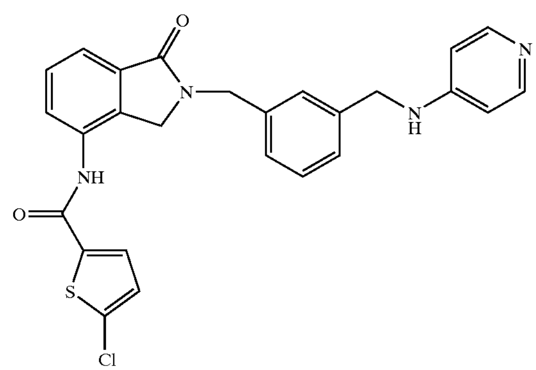 | 489 (100, M + H) ESI | 4.30 (98) Method 1 |
| 181 | 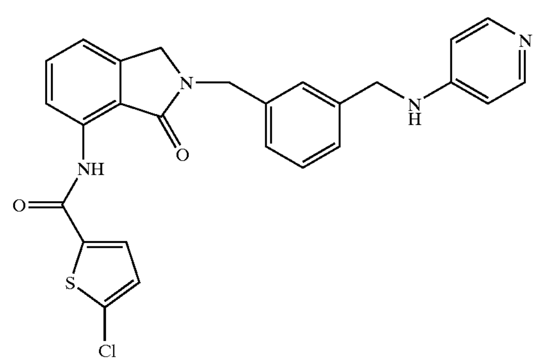 | 489 (100, M + H) ESI | 4.80 (99) Method 1 |

-continued

| Example | Structure | Mass spectrum | LC/HPLC Method |
|---|---|---|---|
| 182 | 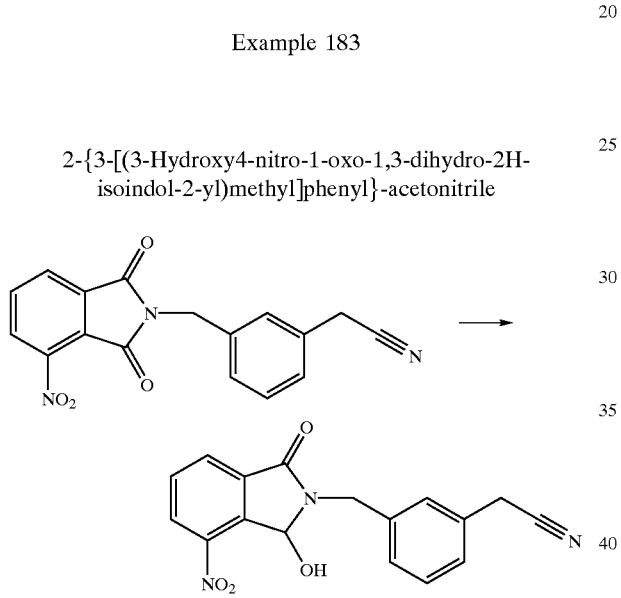 | 463 (100, M + H) ESI | 4.48 (100) Method 1 | 

Example 183

2-{3-[(3-Hydroxy4-nitro-1-oxo-1,3-dihydro-2H-isoindol-2-yl)methyl]phenyl}-acetonitrile

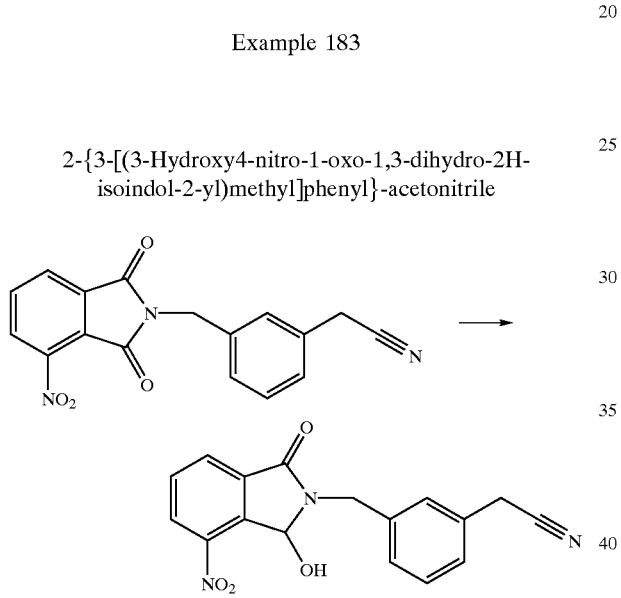

1.81 g (47.7 mmol) of sodium borohydride are introduced a little at a time into a suspension, cooled to −15° C., of 10.95 g (34.1 mmol) of 2-{3-[(4-nitro-1,3-dioxo-1,3-dihydro-2H-isoindol-2-yl)methyl]phenyl}acetonitrile in a mixture of 180 ml of dichloromethane and 180 ml of methanol. Over a period of 2 h, the mixture is warmed to room temperature, and the solution is then, carefully, slightly acidified using 1N hydrochloric acid solution. After concentration to about 100 ml, the residue is taken up in dichloromethane/methanol (98:2) and the mixture is washed with water and sat. sodium chloride solution, dried over magnesium sulfate and concentrated (to about 100 ml). Dichloromethane is added to the crystal slurry, the mixture is filtered off and the solid is dried under high vacuum. Yield: 6.8 g (61.7% of theory);

MS (DCI, $NH_3$): m/z (%)=341 ($M+NH_4$, 100); HPLC (Method 2): rt (%)=6.99 (94.1).

Example 184

2-{3-[(4-Amino-3-hydroxy-1-oxo-1,3-dihydro-2H-isoindol-2-yl)methyl]phenyl}-acetonitrile

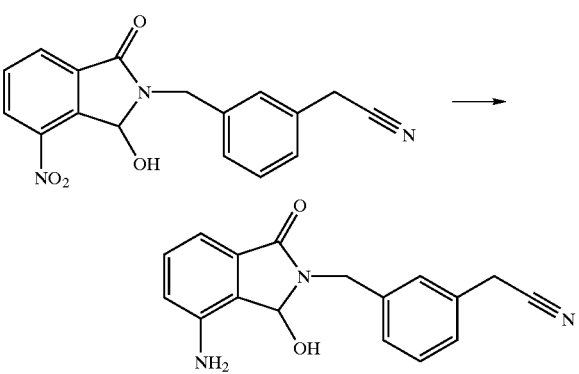

Under argon, 1.5 g of palladium-on-carbon (10%) are added to a suspension of 6.47 g (20 mmol) of 2-{3-[(3-hydroxy-4-nitro-1-oxo-1,3-dihydro-2H-isoindol-2-yl) methyl]phenyl}-acetonitrile in a mixture of methanol (100 ml), THF (100 ml) and ethyl acetate (100). Under a $H_2$ atmosphere (atmospheric pressure), the mixture is stirred vigorously overnight. The reaction mixture is filtered through Celite and concentrated. The product is dried under high vacuum. Yield: 5.89 g (90.3% of theory, purity about 90%);

MS (DCI, $NH_3$): m/z (%)=311 ($M+NH_4$, 100); HPLC (Method 1): rt (%)=3.36 (88).

Example 185

2-{3-[(4-Amino-1-oxo-1,3-dihydro-2H-isoindol-2-yl)methyl]phenyl}acetonitrile

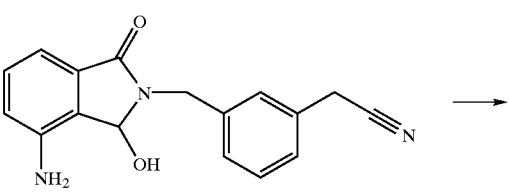

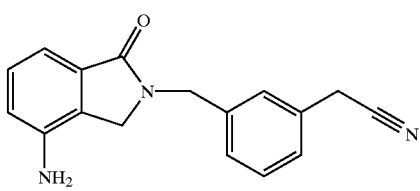

At room temperature, initially 8 ml (50 mmol) of triethylsilane and then dropwise, 20 ml (260 mmol) of TFA are added to a suspension of 5.87 g (20 mmol, purity about 90%) of 2-{3-[(4-amino-3-hydroxy-1-oxo-1,3-dihydro-2H-isoindol-2-yl)methyl]phenyl}acetonitrile in 200 ml dichloromethane. The mixture is stirred at room temperature for 4 h and then concentrated and dried under high vacuum. The residue is taken up in dichloromethane and the mixture is washed with sat. sodium bicarbonate solution and sat. sodium chloride solution, dried over magnesium sulfate and concentrated to about 50 ml. About 100 ml of ether are added to the crystal slurry, which is then stirred for about 2 h and filtered. Yield: 4.36 g (78.7% of theory);

MS (EI pos): m/z (%) 277 (M+, 100); HPLC (Method 1): rt (%) 3.36 (90).

Example 186

5-Chloro-N-{2-[3-(cyanomethyl)benzyl]-1-oxo-2,3-dihydro-1H-isoindol-4-yl}-2-thiophenecarboxamide

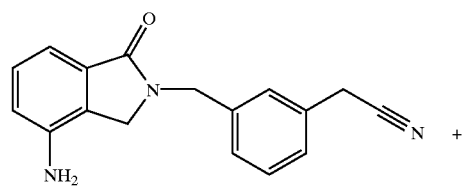

+

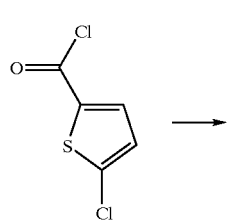

→

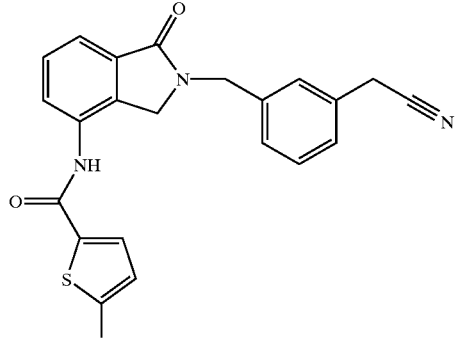

3.24 ml (40 mmol) of pyridine and 36.6 mg (0.3 mmol) of 4-dimethylaminopyridine are added to a suspension of 2.77 g (10 mmol) of 2-{3-[(4-amino-1-oxo-1,3-dihydro-2H-isoindol-2-yl)methyl]phenyl}acetonitrile in 30 ml absolute THF. The mixture is cooled to 0° C., and 2.44 g (12.5 mmol) of 5-chlorothiophene-2-carbonyl chloride are added dropwise. After the addition has ended, ice-cooling is removed and the mixture is warmed to room temperature. After 1.5 h, the mixture is diluted with dichloromethane, washed with sat. sodium bicarbonate solution and sat. sodium chloride solution, dried over magnesium sulfate and concentrated. The residue is taken up in a little dichloromethane and crystallized with ether. The crystal slurry is stirred for 2 h and then filtered off with suction and dried under high vacuum.

Yield: 3.83 g (90.8% of theory);

MS (DCI, NH$_3$): m/z (%)=444 (M+Na, 32), 422 (M+H, 100); HPLC (Method 1): rt (%)=4.44 (95).

General Procedure (V) for Forming Anilides from 2-{3-[(4-amino-1-oxo-1,3-dihydro-2H-isoindol-2-yl)methyl]phenyl}acetonitrile and acid chlorides generated in situ At room temperature, a stock solution of N-(1-chloro-2-methyl-1-propenyl)-N,N-dimethylamine (2.4 eq.) in absolute dichloromethane (about 2.5 mol/l) is added dropwise to a mixture of the corresponding carboxylic acid (2.0 eq) in absolute dichloromethane (about 0.25 mol/l). After 15 to 30 min at room temperature, 1 eq. of 2-{3-[(4-amino-1-oxo-1,3-dihydro-2H-isoindol-2-yl)methyl]phenyl}acetonitrile is added and the mixture is stirred vigorously at room temperature for 1.5 to 3 h and, after dilution with absolute dichloromethane, about 5 eq. of polymer-bound trisamine (PS trisamine, about 4 mmol/g) are added. The mixture is shaken for about 2 h and filtered, and the filtrate is concentrated. The product can be purified either by crystallization using dichloromethane/ether mixtures or by chromatography on silica gel (dichloromethane/methanol mixtures).

| Example | Structure | Mass spectrum | LC/HPLC Method |
|---|---|---|---|
| 187 | 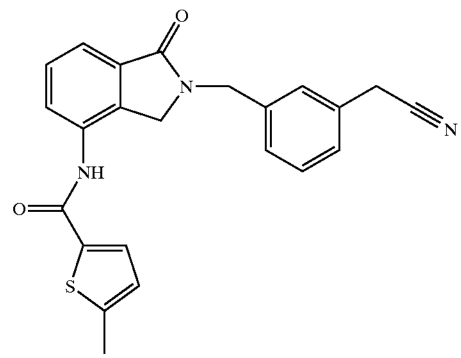 | 419 (100, M + NH₄) DCI | 4.10 (95) Method 2 |
| 188 | 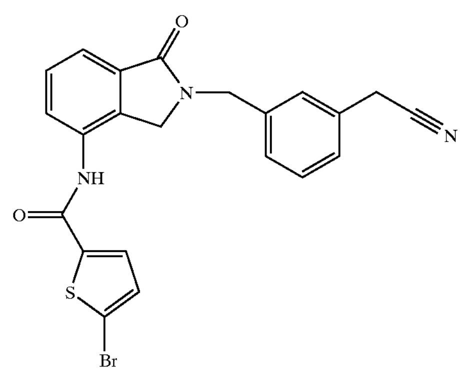 | 483/485 (100, M + NH₄) DCI | 4.43 (95) Method 2 |

Example 189

N-2-{3-[2-Amino-2-(hydroxyimino)ethyl]benzyl}-1-oxo-2,3-dihydro-1H-isoindol-4-yl)-5-chloro-2-thiophenecarboxamide

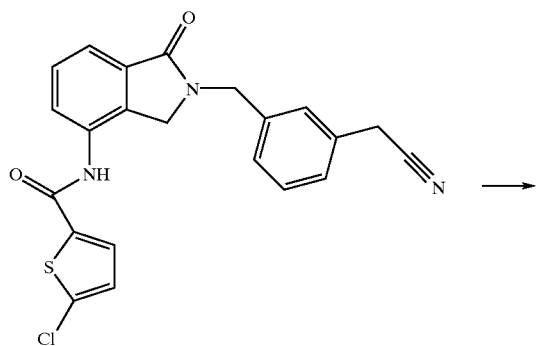

-continued

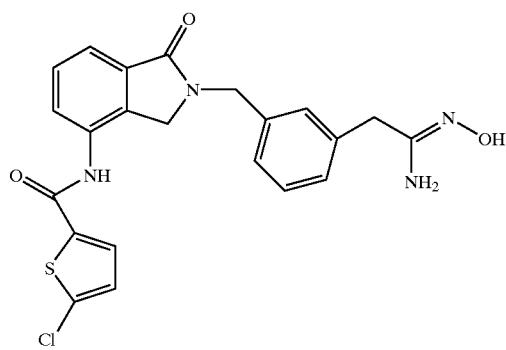

90 mg (1.3 mmol) of hydroxylamine hydrochloride and 0.2 ml (1.4 mmol) of triethylamine are added to a mixture of 436 mg (1.0 mmol) of 5-chloro-N-{2-[3-(cyanomethyl) benzyl]-1-oxo-2,3-dihydro-1H-isoindol-4-yl}-2-thiophenecarboxamide in 5 ml of 2-propanol, and the mixture is heated at reflux for 30 min. After cooling to room temperature, water is added and the precipitated solid is filtered off with suction. The product is isolated by chromatography on silica gel. Yield: 45.3 mg (10% of theory);

MS (ESI): m/z (%/)=455 (M+H, 100); HPLC (Method 1): rt (%)=4.03 (90).

General Procedure (VI) (Suzuki Coupling) for Preparing Biphenyl Derivatives

Under argon, 1.2 eq. of boronic acid and 2.5 eq. of sodium carbonate in the form of a 2-molar aqueous solution are added to a solution of 1 eq. of aryl bromide in 1,2-dimethoxyethane (about 0.2 to 0.5 mol/l) and dichlorobis(triphenylphosphine)-palladium(II) (0.05 eq.). The mixture is heated at reflux for 1 h to 5 h and, after cooling, water is added. The mixture is extracted with ethyl acetate and the organic phase is washed with sat. sodium chloride solution, dried over magnesium sulfate and concentrated. The product is isolated and purified by chromatography on silica gel (dichloromethane, dichloromethane/methanol or ethyl acetate/cyclohexane mixtures).

According to the general procedure (Suzuki coupling), the following biphenyl derivatives can be obtained from 3-hydroxymethylphenylboronic acid (can be prepared according to WO 97/36893 or WO 95/29682) and aryl bromides:

| Structure | Starting material | Mass | LC/HPLC Method | Reference |
|---|---|---|---|---|
| 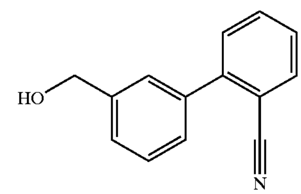 | 2-bromo-benzonitrile | 227 (M + NH$_4$, 100), DCI | 3.82 (100) Method 2 | — |
| 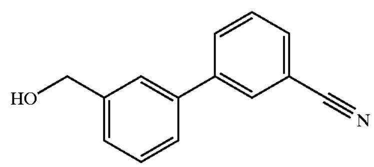 | 3-bromo-benzonitrile | 227 (M + NH$_4$, 100), DCI | 3.90 (100) Method 2 | — |
| 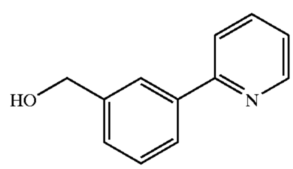 | 2-bromo-pyridine | 186 (M + H, 100), DCI | 3.44 (91) Method 2 | Chem. Pharm. Bull., 1985, 1009 |
| 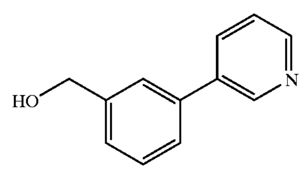 | 3-bromo-pyridine | 186 (M + H, 100), DCI | 2.95 (100) Method 1 | CAS -RN 85553-54-4 |
| 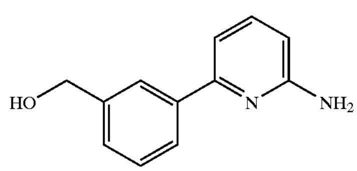 | 2-amino-6-bromo-pyridine | 201 (M + H, 100), DCI | 3.23 (85) Method 1 | — |
| 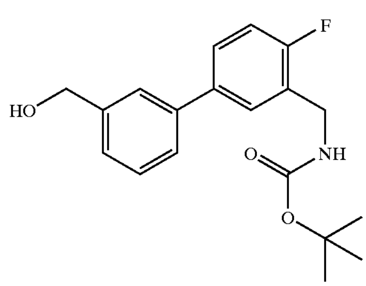 | tert-butyl 5-bromo-2-fluorobenzyl carbamate | 349 (M + NH4, 74), 293 (100) DCI | 4.63 (94) Method 1 | — |

According to the general procedure (Suzuki coupling), (3'-amino[1,1'-biphenyl]-4-yl)methanol can be obtained from 3-aminophenylboronic acid hemisulfate and 4-bromobenzyl alcohol.

General Procedure (VII) for the Synthesis of methylbiphenyl-substituted 5-chloro-N-(1-oxo-2,3-dihydro-1H-isoindol-4-yl)-2-thiophenecarboxamide Derivatives Diethyl azodicarboxylate (1.2 to 1.5 eq.) is added dropwise to a mixture, cooled with water, of 5-chloro-N-(1,3-dioxo-2,3-dihydro-1H-isoindol-4-yl)-2-thiophenecarboxamide (1.0 eq.), the appropriate hydroxymethyl-substituted biphenyl derivative (1.2 eq.) and triphenylphosphine (1.2 eq.) in absolute THF (about 0.1 mol/l). The reaction mixture is stirred vigorously at room temperature for about 1 h and then concentrated. The product can be isolated and purified by crystallization with ether or by chromatography on silica gel (ethyl acetate/cyclohexane mixtures).

| Example | Structure | Mass spectrum | LC/HPLC Method |
|---|---|---|---|
| 190 | 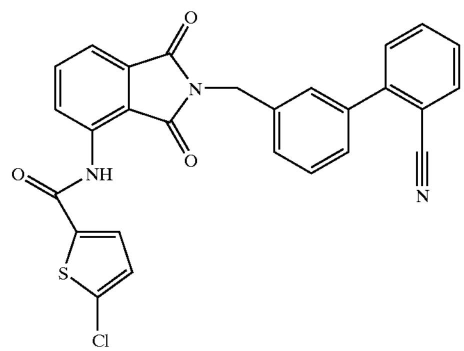 | 515 (M + NH$_4$, 100) DCI | 5.68 (96) Method 2 |
| 191 | 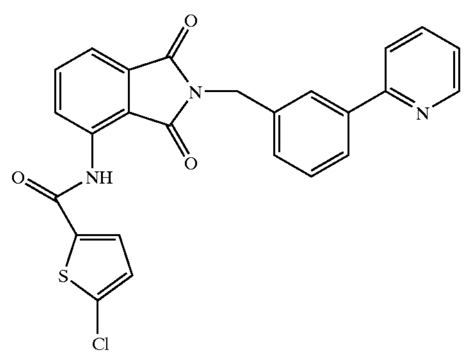 | 473 (M + H, 20) | 4.56 (99) Method 1 |
| 192 | 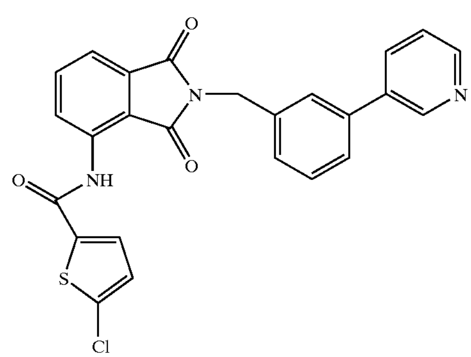 | 473 (M + H), 20) ESI | 4.60 (99) Method 2 |

| Example | Structure | Mass spectrum | LC/HPLC Method |
|---|---|---|---|
| 193 | 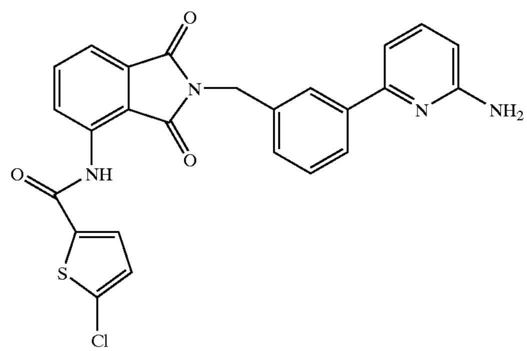 | 489 (M + H, 20) ESI | 4.77 (99) Method 1 |

Example 194

Starting with tert-butyl {3'-[(4-{[(5-chloro-2-thienyl)carbonyl]amino}-1,3-dioxo-1,3-dihydro-2H-isoindol-2-yl)methyl]-4-fluoro[1,1'-biphenyl]-3-yl}methylcarbamate, by treating the crude product with etheral hydrochloric acid solution, it is possible to obtain N-(2-{[3'-(aminomethyl)-4'-fluoro[1,1'-biphenyl]-3-yl]methyl}-1,3-dioxo-2,3-dihydro-1H-isoindol-4-yl)-5-chloro-2-thiophenecarboxamide hydrochloride.

MS (ESI): m/z (%)=520 (M−Cl, 15), 201 (100); HPLC (Method 1): rt (%)=4.81 (92).

Example 195

N-(2-{[4-trans-(Aminomethyl)cyclohexyl]methyl}-1,3-dioxo-2,3-dihydro-1H-isoindol-4-yl)-5-chloro-2-thiophenecarboxamide

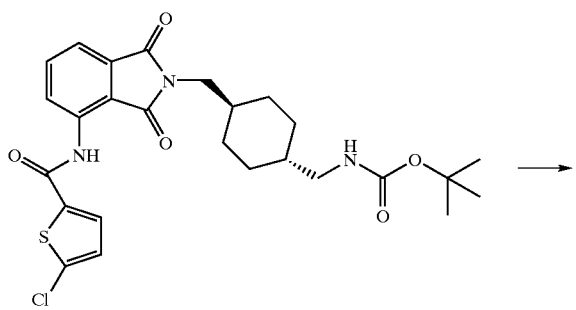

100 ml of a mixture of TFA and water (9:1) are added dropwise to an ice-cooled solution of 3.23 g of tert-butyl {4-trans-[(4-{[(5-chloro-2-thienyl)carbonyl]amino}-1,3-dioxo-1,3-dihydro-2H-isoindol-2-yl)methyl] cyclohexyl}methylcarbamate (5.65 mmol) in 100 ml of chloroform. Ice-cooling is removed and the mixture is stirred at room temperature for 1.5 h and then concentrated. The residue is taken up in dichloromethane/methanol and the mixture is washed with sat. sodium bicarbonate solution, dried over magnesium sulfate and concentrated. The resulting mixture is separated by preparative RP-HPLC. Yield: 314 mg (12.9% of theory).

MS (DCI, NH$_4$): m/z (%)=43 (M+H, 100); LC: rt (%)= 8.73 (96.2).

Example 196

5-Chloro-N-{1,3-dioxo-2-[(4-{[(2,2,2-trifluoroacetyl)amino]methyl}cyclohexyl)methyl]-2,3-dihydro-1H-isoindol-4-yl}-2-thiophenecarboxamide can be Isolated as a By-Product MS (DCI, NH$_4$): m/z (%)=545 (M+NH$_4$, 100); LC: rt (%)=11.30 (98.9).

Example 197

5-Chloro-N-{2-[(4-{[trans-(cyanomethyl)amino]methyl}cyclohexyl)methyl]-1,3-dioxo-2,3-dihydro-1H-isoindol-4-yl}-2-thiophenecarboxamide

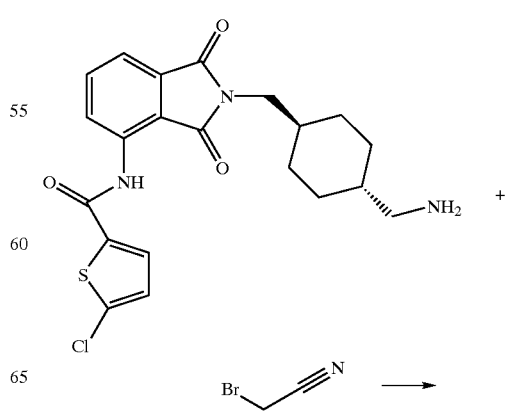

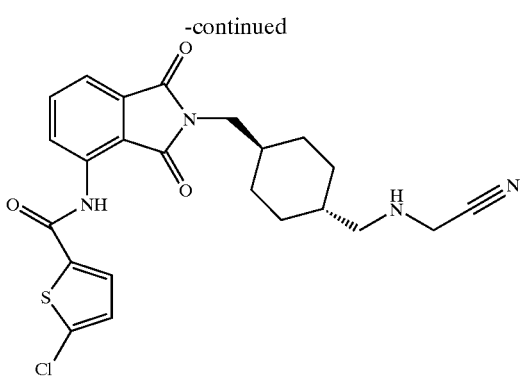

0.02 ml (0.28 mmol) of bromoacetonitrile and 0.06 ml (0.46 mmol) of triethylamine are added successively to 100 mg (0.23 mml) of N-(2-{[4-trans-(aminomethyl)cyclohexyl]methyl}-1,3-dioxo-2,3-dihydro-1H-isoindol-4-yl)-5-chloro-2-thiophenecarboxamide in 2.5 ml of absolute DMF. The mixture is stirred at room temperature overnight and then concentrated under reduced pressure, and the residue is taken up in dichloromethane. The mixture is washed with saturated sodium bicarbonate solution, dried and concentrated. The product is isolated by chromatography on silica gel (dichloromethane/methanol 99:1). Yield: 52 mg (47.7% of theory).

MS (DCI, $NH_4$): m/z (%)=488 (M+$NH_4$, 35), 471 (M+H, 20), 444 (100).

Example 198

5-Chloro-N-(2-{[cis-3-(cyanomethyl)cyclohexyl]methyl}-1-hydroxy-3-oxo-2,3-dihydro-1H-isoindol-4-yl)-2-thiophenecarboxamide

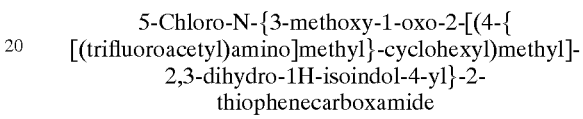

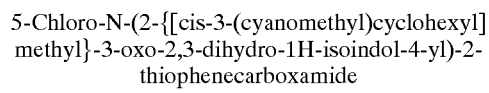

340 mg (0.77 mmol) of 5-chloro-N-(2-{[cis-3-(cyanomethyl)cyclohexyl]methyl}-1,3-dioxo-2,3-dihydro-1H-isoindol-4-yl)-2-thiophenecarboxamide are dissolved in a mixture of 17 ml of dichloromethane and 17 ml of methanol. At 0° C., sodium borohydride (43.6 mg, 1.15 mmol) is added a little at a time. After 3 h, the mixture is acidified slightly using 1N hydrochloric acid solution and extracted repeatedly with dichloromethane. The combined organic extracts are dried over magnesium sulfate and concentrated. The product mixture is separated by chromatography on silica gel (dichloromethane/methanol 98:2). Yield: 122 mg (35.7% of theory);

MS (ES$^+$): m/z (%)=444 (M+H, 100); MS (ES$^-$): m/z (%)=442 (M–H, 100).

In an analogous manner, the compound below can be prepared from 5-chloro-N-{1,3-dioxo-2-[(4-{[(2,2,2-trifluoroacetyl)amino]methyl}cyclohexyl)methyl]-2,3-dihydro-1H-isoindol-4-yl}-2-thiophenecarboxamide:

Example 199

5-Chloro-N-{3-methoxy-1-oxo-2-[(4-{[(trifluoroacetyl)amino]methyl}-cyclohexyl)methyl]-2,3-dihydro-1H-isoindol-4-yl}-2-thiophenecarboxamide MS (ESI): m/z (%)=566 (M+Na, 34), 512 (100); HPLC (Method 1): rt (%)=4.85 (100).

Example 200

5-Chloro-N-(2-{[cis-3-(cyanomethyl)cyclohexyl]methyl}-3-oxo-2,3-dihydro-1H-isoindol-4-yl)-2-thiophenecarboxamide

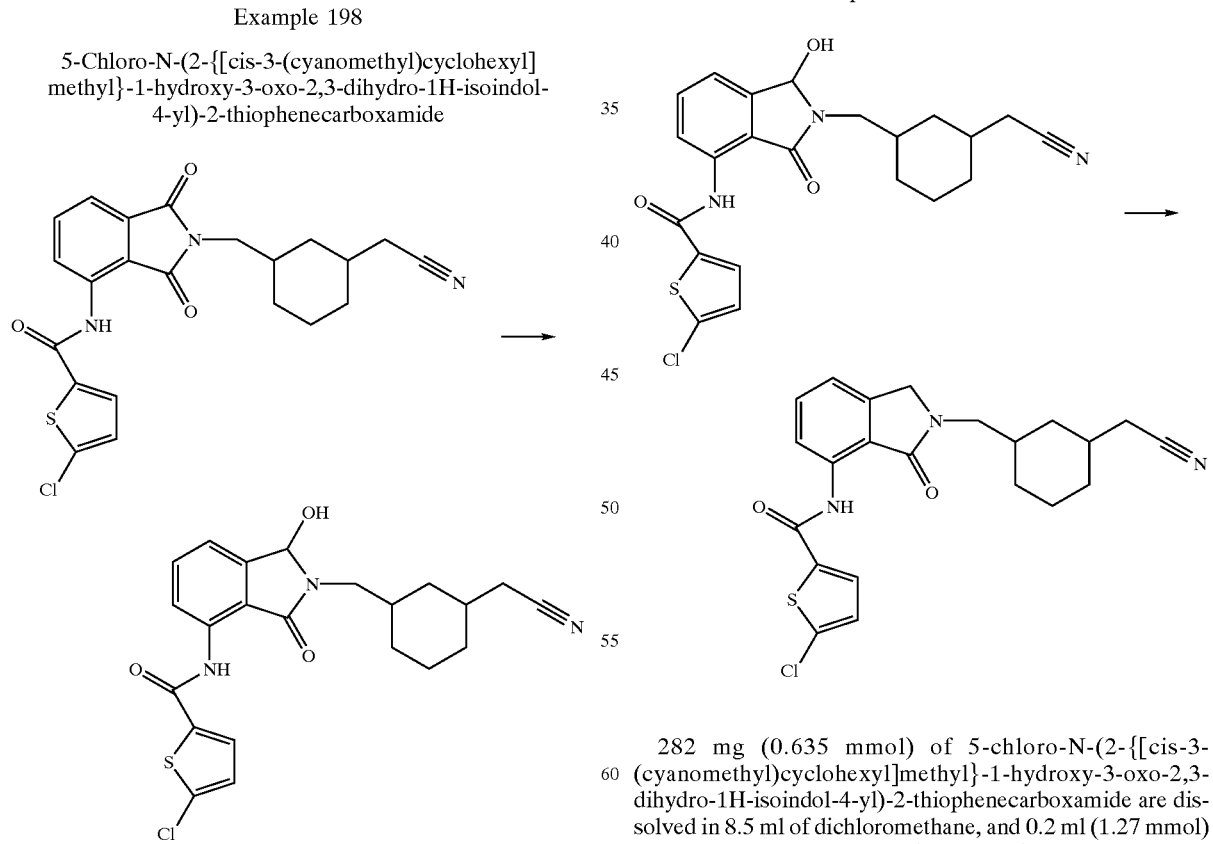

282 mg (0.635 mmol) of 5-chloro-N-(2-{[cis-3-(cyanomethyl)cyclohexyl]methyl}-1-hydroxy-3-oxo-2,3-dihydro-1H-isoindol-4-yl)-2-thiophenecarboxamide are dissolved in 8.5 ml of dichloromethane, and 0.2 ml (1.27 mmol) of triethylsilane and 0.59 ml (7.62 mmol) of TFA are added. The mixture is stirred at room temperature overnight and then concentrated. The residue is taken up in dichloromethane, and the mixture is washed with 1N sodium hydroxide solution. The organic phase is dried over magnesium sulfate and concentrated, and the residue is purified by chromatography on silica gel (dichloromethane/methanol 99:1). Yield: 150 mg (55.2% of theory);

MS (ESI): m/z (%)=450 (M+Na, 100), 428 (M+H, 78); HPLC (Method 1): rt (%)=5.26 (100).

Example 201

5-Chloro-N-{1-oxo-2-[(4-{[(trifluoroacetyl)amino]methyl}cyclohexyl)methyl]-2,3-dihydro-1H-isoindol-4-yl}-2-thiophenecarboxamide from 5-chloro-N-{3-methoxy-1-oxo-2-[(4-{[(trifluoroacetyl)amino]methyl}cyclohexyl)methyl]-2,3-dihydro-1H-isoindol-4-yl}-2-thiophenecarboxamide;

MS (ES+): m/z (%)=514 (M+H, 100); HPLC (Method 1): rt (%)=4.57 (96).

Example 202

5-Chloro-N-{3-oxo-2-[(4-{[(trifluoroacetyl)amino]methyl}cyclohexyl)methyl]-2,3-dihydro-1H-isoindol-4-yl}-2-thiophenecarboxamide from 5-chloro-N-{1-hydroxy-3-oxo-2-[(4-{[(trifluoroacetyl)amino]methyl}-cyclohexyl)methyl]-2,3-dihydro-1H-isoindol-4-yl}-2-thiophenecarboxamide;

MS (ES+): m/z (%)=514 (M+H, 100); HPLC (Method 1): rt (%)=5.22 (100).

Example 203

N-(2-{[4-(Aminomethyl)cyclohexyl]methyl}-1-oxo-2,3-dihydro-1H-isoindol-4-yl)-5-chloro-2-thiophenecarboxamide

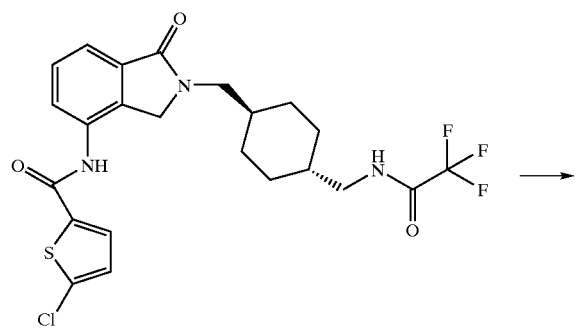

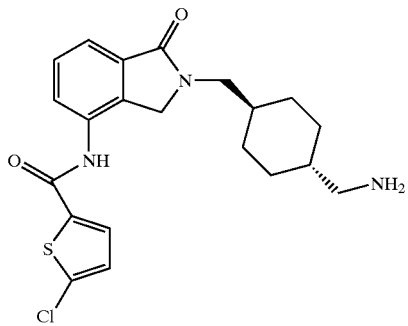

A few drops of water and 20 mg of sodium methoxide are added to a suspension of 102 mg (0.2 mmol) of 5-chloro-N-{1-oxo-2-[(4-{[(trifluoroacetyl)amino]methyl}-cyclohexyl)methyl]-2,3-dihydro-1H-isoindol-4-yl}-2-thiophenecarboxamide in 6 ml of methanol. The resulting solution is stirred at room temperature overnight, 1 ml of a 1N sodium hydroxide solution is then added and the mixture is heated at 50° C. After 3 h, the mixture is cooled and diluted with dichloromethane/methanol 95:5. The mixture is washed with 1N sodium hydroxide solution, dried over sodium sulfate, concentrated and dried under high vacuum. Yield: 81.1 mg (98% of theory);

MS (ESI): m/z (%)=418 (M+H, 40), 305 (100); HPLC (Method 1): rt (%)=3.93 (98).

Example 204

N-(2-{[4-(Aminomethyl)cyclohexyl]methyl}-3-oxo-2,3-dihydro-1H-isoindol-4-yl)-5-chloro-2-thiophenecarboxamide can be prepared analogously from 5-chloro-N-{3-oxo-2-[(4-{[(trifluoroacetyl)amino]methyl}cyclohexyl)methyl]-2,3-dihydro-1H-isoindol-4-yl}-2-thiophenecarboxamide;

MS (ESI): m/z (%)=418 (M+H, 80); HPLC (Method 1): rt (%)=4.40 (92).

Example 205

5-Chloro-N-{2-[3-(hydroxymethyl)benzyl]-1,3-dioxo-2,3-dihydro-1H-isoindol-4-yl}-2-thiophenecarboxamide

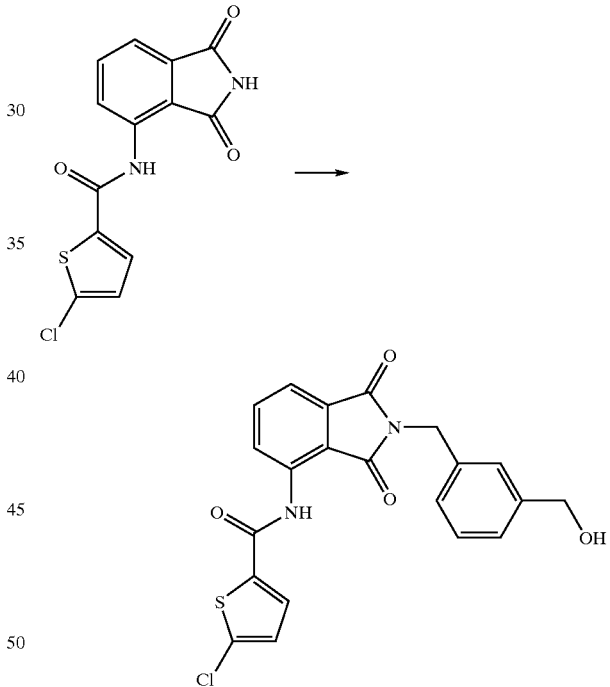

Under argon and at 0° C., diethyl azodicarboxylate (3.3 ml, 21.2 mmol) is added dropwise to a solution of 5-chloro-N-(1,3-dioxo-2,3-dihydro-1H-isoindol-4-yl)-2-thiophenecarboxamide (5.0 g, 16.3 mmol), 3-(hydroxymethyl)benzyl alcohol (2.9 g, 21.2 mmol) and triphenylphosphine (5.6 g, 21.2 mmol) in tetrahydrofuran (75 ml). The reaction mixture is stirred at room temperature for 2 h, and water is added. After addition of dichloromethane and phase separation, the aqueous phase is extracted with dichloromethane. The combined organic phases are dried (sodium sulfate), filtered and concentrated under reduced pressure. The desired product is purified by flash chromatography (dichloromethane/methanol mixtures). Yield: 5.6 g, 81% of theory.

MS (DCI, NH$_3$): m/z (%)=444 ([M+NH$_4$]$^+$, 100), Cl pattern; HPLC (Method 1): rt=5.05 min.

Preparation of the Derivatives of N-{2-[3-(aminomethyl)benzyl]-1,3-dioxo-2,3-dihydro-1H-isoindol-4-yl}-5-chloro-2-thiophenecarboxamide

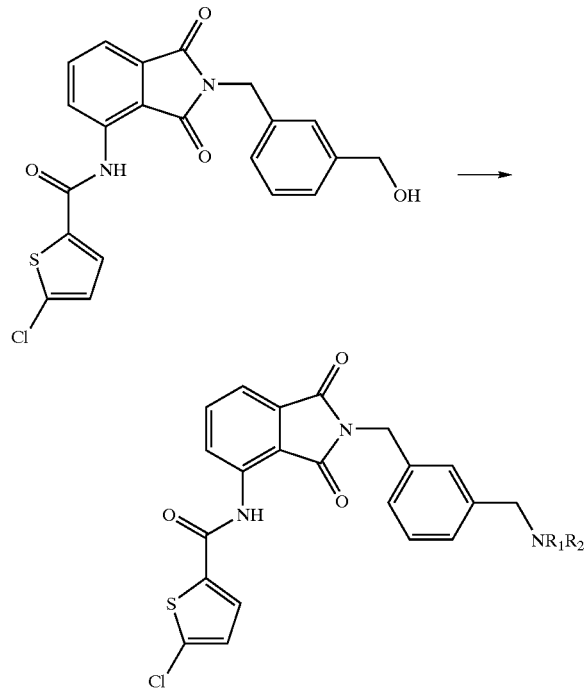

Under argon and at −20° C., N-bromosuccinimide is added a little at a time to a solution of 5-chloro-N-{2-[3-(hydroxymethyl)benzyl]-1,3-dioxo-2,3-dihydro-1H-isoindol-4-yl}-2-thiophenecarboxamide and triphenylphosphine (1 eq.) in tetrahydrofuran (0.05 mol/l). The mixture is stirred for 5 min, and the amine is then added. After a further 5 min, the reaction mixture is slowly warmed to room temperature and heated under reflux for 10 h, and water is added. After addition of dichloromethane and phase separation, the aqueous phase is extracted with dichloromethane. The combined organic phases are dried (sodium sulfate), filtered and concentrated under reduced pressure. The desired product is purified by flash chromatography (cyclohexane/ethyl acetate mixtures).

The following compounds can be prepared correspondingly:

Example 206

5-Chloro-N-{1,3-dioxo-2-[3-(1-pyrrolidinylmethyl)benzyl]-2,3-dihydro-1H-isoindol-4-yl}-2-thiophenecarboxamide MS (ESI): m/z (%)=480 ([M+H]$^+$, 88), Cl pattern; HPLC (Method 1): rt=4.68 min.

Example 207

5-Chloro-N-(2-{3-[(dimethylamino)methyl]benzyl}-1,3-dioxo-2,3-dihydro-1H-isoindol-4-yl)-2-thiophenecarboxamide MS (ESI): m/z (%)=454 ([M+H]$^+$, 30), Cl pattern; HPLC (Method 1): rt=4.70 min.

Example 208

5-Chloro-N-{1,3-dioxo-2-[3-(1-piperidinylmethyl)benzyl]-2,3-dihydro-1H-isoindol-4-yl}-2-thiophenecarboxamide MS (ESI): m/z (%)=494 ([M+H]$^+$, 45), Cl pattern; HPLC (Method 1): rt=4.78 min.

3-({[tert-Butyl(dimethyl)silyl]oxy}methyl)benzylamine

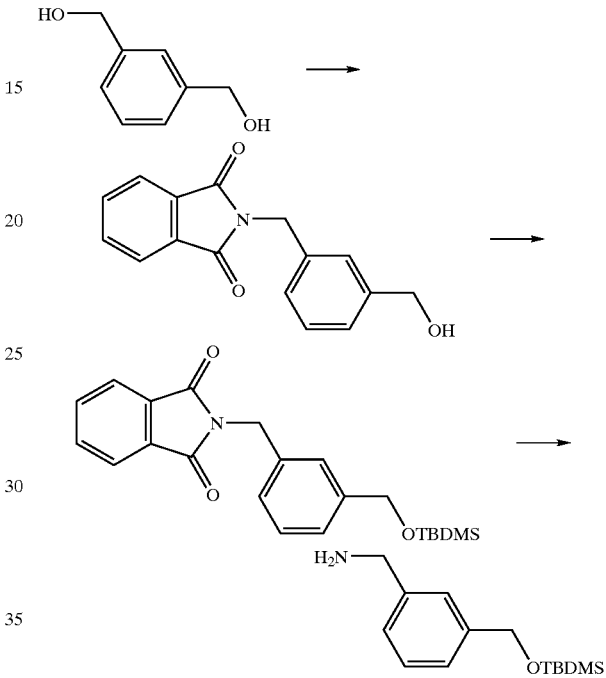

2-[3-(Hydroxymethyl)benzyl]-1H-isoindole-1,3(2H)-dione

Under argon and at 0° C., diethyl azodicarboxylate is added dropwise to a solution of phthalimide (5.0 g, 34.0 mmol), 3-(hydroxymethyl)benzyl alcohol (5.6 g, 40.8 mmol) and triphenylphosphine (10.7 g, 40.8 mmol) in tetrahydrofuran (68 ml). The reaction mixture is stirred at room temperature for 15 h, and water is added. After addition of dichloromethane and phase separation, the aqueous phase is extracted with dichloromethane. The combined organic phases are dried (sodium sulfate), filtered and concentrated under reduced pressure. The desired product is purified by flash chromatography (petroleum ether/ethyl acetate mixtures). Yield: 6.5 g, 71% of theory.

MS (DCI, NH$_3$): m/z (%)=285 ([M+NH$_4$]$^+$, 100); R$_f$ (silica gel, dichloromethane/methanol 20:1)=0.75.

2-[3-({[tert-Butyl(dimethyl)silyl]oxy}methyl)benzyl]-1H-isoindole-1,3(2H)-dione

Under argon and at room temperature, imidazole (1.0 g, 15.0 mmol) and tert-butyldimethylsilyl chloride (1.7 g, 11.2 mmol) are added to a solution of 2-[3-(hydroxymethyl)benzyl]-1H-isoindole-1,3(2H)-dione (2.0 g, 7.5 mmol) in tetrahydrofuran (22.5 ml). The reaction mixture is stirred at room temperature for 16 h, and water is added. After addition of dichloromethane and phase separation, the aqueous phase is extracted with dichloromethane. The combined organic phases are dried (sodium sulfate), filtered and concentrated under reduced pressure. The desired product is purified by flash chromatography (petroleum ether/ethyl acetate mixtures). Yield: 2.7 g, 95% of theory.

MS (ESI): m/z (%)=404 ([M+Na]$^+$, 34); $R_f$ (silica gel, petroleum ether/ethyl acetate 3:1)=0.84.

3-({[tert-Butyl(dimethyl)silyl]oxy}methyl)benzylamine

At room temperature, a hydrazine solution (35% strength in water, 0.6 ml, 6.6 mmol) is added to a solution of 2-[3-({[tert-butyl(dimethyl)silyl]oxy}methyl)benzyl]-1H-isoindole-1,3(2H)-dione (1.7 g, 4.4 mmol) in ethanol (44 ml), the mixture is stirred at room temperature for 15 h and water is added. After addition of dichloromethane and phase separation, the aqueous phase is extracted with dichloromethane. The combined organic phases are dried (sodium sulfate), filtered and concentrated under reduced pressure. The desired product is used without further purification for the next reaction.

MS (ESI): m/z (%)=252 ([M+H]$^+$, 100); LC (Method 5): rt=3.07 min.

Example 209

5-Chloro-N-[2-(3-formylbenzyl)-1-oxo-2,3-dihydro-1H-isoindol-4-yl]-2-thiophenecarboxamide

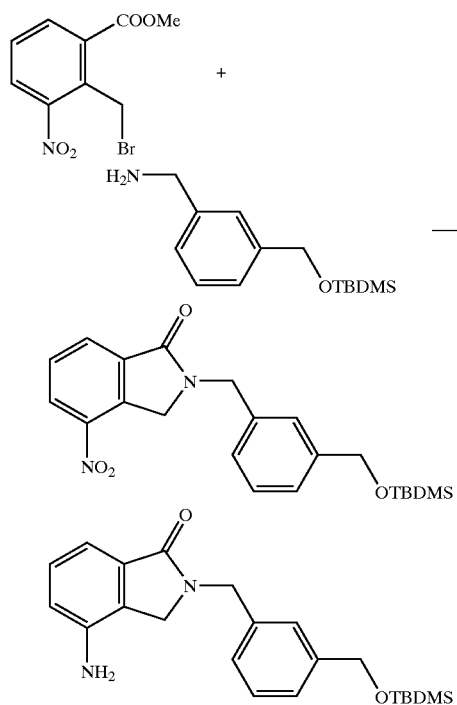

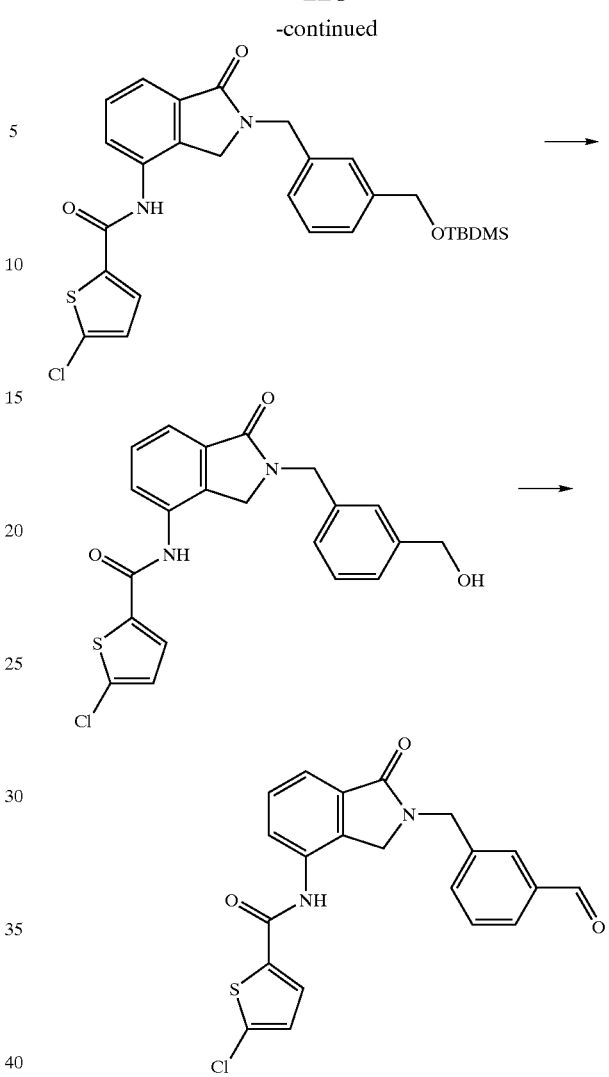

4-Nitro-2-[3-(silylmethyl)benzyl]-1-isoindolinone

At room temperature, triethylamine (3.5 ml, 24.9 mmol) is added to a solution of methyl 2-(bromomethyl)-3-nitrobenzoate (J. Org. Chem., 1999, 9731–9734) (6.2 g, 22.6 mmol) and 3-({[tert-butyl(dimethyl)silyl]oxy}methyl)benzylamine (5.7 g, 22.6 mmol) in methanol (113 ml). The reaction mixture is heated under reflux for 16 h, and saturated aqueous ammonium chloride solution is then added. After addition of dichloromethane and phase separation, the aqueous phase is extracted with dichloromethane. The combined organic phases are dried (sodium sulfate), filtered and concentrated under reduced pressure. The desired product is purified by flash chromatography (cyclohexane/ethyl acetate mixtures). Yield: 5.1 g, 54% of theory.

MS (ESI): m/z (%)=413 ([M+H]$^+$, 10), 435 ([M+Na]$^+$, 25); $R_f$ (silica gel, petroleum ether/ethyl acetate 2:1)=0.53.

4-Amino-2-[3-(silylmethyl)benzyl]-1-isoindolinone

A solution of 4-nitro-2-[3-(silylmethyl)benzyl]-1-isoindolinone (5.2 g, 12.5 mmol) in tetrahydrofuran (60 ml) is, in the presence of palladium (10% on carbon, 375 mg), stirred under an atmosphere of hydrogen for 20 h and filtered, and the filtrate is concentrated under reduced pressure. The desired product is purified by flash chromatography (cyclohexane/ethyl acetate mixtures). Yield: 3.8 g, 79% of theory.

MS (ESI): m/z (%)=383 ([M+H]$^+$, 23), 400 ([M+Na]$^+$, 100); R$_f$ (silica gel, petroleum ether/ethyl acetate 2:1, run three times)=0.53.

5-Chloro-N-{1-oxo-2-[3-(silylmethyl)benzyl]-2,3-dihydro-1H-isoindol-4-yl}-2-thiophenecarboxamide Under argon and at 0° C., 5-chloro-2-thiophenecarbonyl chloride (1.7 g, 9.2 mmol) and 4-dimethylaminopyridine (93 mg, 0.8 mmol) are added to a solution of 4-amino-2-[3-(silylmethyl)benzyl]-1-isoindolinone (2.9 g, 7.7 mmol) in tetrahydrofuran (26 ml) and pyridine (12 ml). The reaction mixture is stirred at room temperature for 12 h, and water is added. After addition of dichloromethane and phase separation, the aqueous phase is extracted with dichloromethane. The combined organic phases are dried (sodium sulfate), filtered and concentrated under reduced pressure. The desired product is purified by flash chromatography (dichloromethane/methanol mixtures). Yield: 3.9 g, 97% of theory.

MS (ESI): m/z (%)=383 ([M+H]$^+$, 23), 400 ([M+Na]$^+$, 100); R$_f$ (silica gel, petroleum ether/ethyl acetate 2:1, run three times)=0.53.

5-Chloro-N-{2-[3-(hydroxymethyl)benzyl]-1-oxo-2,3-dihydro-1H-isoindol-4-yl}-2-thiophenecarboxamide Under argon and at room temperature, a solution of tetra-n-butylammonium fluoride (1 M in THF, 4.6 ml, 4.6 mmol) is added to a solution of 5-chloro-N-{1-oxo-2-[3-(silylmethyl)benzyl]-2,3-dihydro-1H-isoindol-4-yl}-2-thiophenecarboxamide (2.0 g, 3.8 mmol) in tetrahydrofuran (38 ml). The reaction mixture is stirred at room temperature for 14 h and concentrated under reduced pressure. The crude product is used without further purification for the next reaction.

MS (ESI): m/z (%)=413 ([M+H]$^+$, 58), 435 ([M+H]$^+$, 100); HPLC (Method 1): rt=4.17 min.

5-Chloro-N-[2-(3-formylbenzyl)-1-oxo-2,3-dihydro-1H-isoindol-4-yl]-2-thiophenecarboxamide Dess-Martin periodinane (1.9 g, 4.6 mmol) is added to a solution of 5-chloro-N-{2-[3-(hydroxymethyl)benzyl]-1-oxo-2,3-dihydro-1H-isoindol-4-yl}-2-thiophenecarboxamide (1.6 g, 3.8 mmol) in dichloromethane (38 ml) and pyridine (1.5 ml) and the mixture is stirred at room temperature for 6 h, and saturated aqueous sodium bicarbonate solution is then added. After addition of ethyl acetate and phase separation, the aqueous phase is extracted with ethyl acetate. The combined organic phases are dried (sodium sulfate), filtered and concentrated under reduced pressure. The desired product is purified by flash chromatography (dichloromethane/methanol mixtures). Yield: 1.5 g, 97% of theory.

MS (ESI): m/z (%)=411 ([M+H]$^+$, 100); HPLC (Method 1): rt=4.35 min.

Reductive amination of 5-chloro-N-[2-(3-formylbenzyl)-1-oxo-2,3-dihydro-1H-isoindol-4-yl]-2-thiophenecarboxamide Under argon and at room temperature, glacial acetic acid (2 eq.) and the appropriate amine (2 eq.) are added to a suspension of 5-chloro-N-[2-(3-formylbenzyl)-1-oxo-2,3-dihydro-1H-isoindol-4-yl]-2-thiophenecarboxamide in tetrahydrofuran (0.05 mol/l) and methanol (0.05 mol/l). The reaction mixture is stirred at 70° C. for 6–9 h, during which the precipitate dissolves. After cooling of the reaction mixture, sodium cyanoborohydride (2 eq.) is added, the mixture is stirred at room temperature for a further 8–10 h and saturated aqueous sodium bicarbonate solution is added. After addition of dichloromethane and phase separation, the aqueous phase is extracted with dichloromethane. The combined organic phases are dried (sodium sulfate), filtered and concentrated under reduced pressure. The desired product is purified by preparative thin-layer chromatography (dichloromethane/methanol mixtures).

The following compounds can be prepared correspondingly:

Example 210

5-Chloro-N-[1-oxo-2-(3-{[(4-pyridinylmethyl)amino]methyl}benzyl)-2,3-dihydro-1H-isoindol-4-yl]-2-thiophenecarboxamide MS (ESI): m/z (%)=503 ([M+H]$^+$, 100), Cl pattern; H?LC (Method 1): rt=3.91 min.

Example 211

5-Chloro-N-(2-{3-[(4-methyl-1-piperazinyl)methyl]benzyl}-1-oxo-2,3-dihydro-1H-isoindol-4-yl)-2-thiophenecarboxamide MS (ESI): m/z (%)=495 ([M+H]$^+$, 100), Cl pattern; HPLC (Method 4): rt=3.15 min.

Example 212

5-Chloro-N-(2-{3-[(3-isoxazolylamino)methyl]benzyl}-1-oxo-2,3-dihydro-1H-isoindol-4-yl)-2-thiophenecarboxamide MS (ESI): m/z (%)=479 ([M+H]$^+$, 100), Cl pattern; HPLC (Method 2): rt=4.52 min.

Example 213

5-Chloro-N-(2-{3-[(dimethylamino)methyl]benzyl}-1-oxo-2,3-dihydro-1H-isoindol-4-yl)-2-thiophenecarboxamide MS (ESI): m/z (%)=440 ([M+H]$^+$, 100), Cl pattern; HPLC (Method 1): rt=3.96 min.

Example 214

5-Chloro-N-(2-{3-[(methylamino)methyl]benzyl}-1-oxo-2,3-dihydro-1H-isoindol-4-yl)-2-thiophenecarboxamide MS (ESI): m/z (%)=426 ([M+H]$^+$, 100), Cl pattern; HPLC (Method 4): rt=2.77 min.

Example 215

5-Chloro-N-{1-oxo-2-[3-(1-piperidinylmethyl)benzyl]-2,3-dihydro-1H-isoindol-4-yl}-2-thiophenecarboxamide MS (ESI): m/z (%)=480 ([M+H]$^+$, 100), Cl pattern; HPLC (Method 1): rt=4.07 min.

Example 216

5-Chloro-N-[2-(3-{[(4-fluorophenyl)amino]methyl}benzyl)-1-oxo-2,3-dihydro-1H-isoindol-4-yl]-2-thiophenecarboxamide MS (ESI): m/z (%)=506 ([M+H]$^+$, 100), Cl pattern; HPLC (Method 2): rt=4.19 min.

Example 217

5-Chloro-N-(2-{3-[(isopropylamino)methyl]
benzyl}-1-oxo-2,3-dihydro-1H-isoindol-4-yl)-2-
thiophenecarboxamide MS (ESI): m/z (%)=454 ([M+H]⁺, 100), Cl pattern;
HPLC (Method 1): rt=4.01 min.

Example 218

N-{2-[3-((E)-{[Amino(imino)methyl]
hydrazono}methyl)benzyl]-1,3-dioxo-2,3-dihydro-
1H-isoindol-4-yl}-5-chloro-2-thiophenecarboxamide
from 5-chloro-N-{2-[3-(hydroxymethyl)benzyl]-1,3-
dioxo-2,3-dihydro-1H-isoindol-4-yl}-2-
thiophenecarboxamide

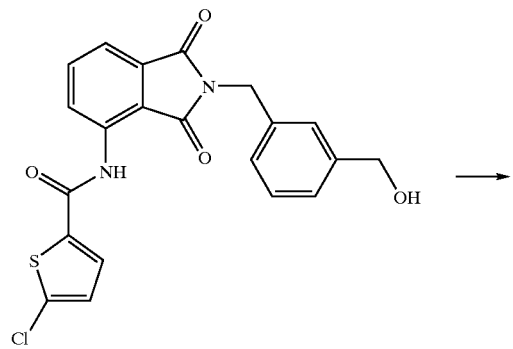

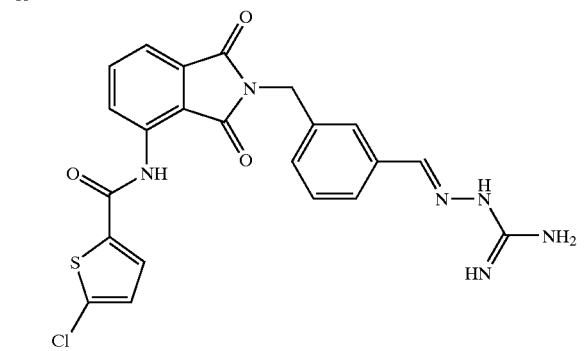

Under argon and at room temperature, Dess-Martin periodinane (1.2 eq.) is added to a suspension of 5-chloro-N-{2-[3-(hydroxymethyl)benzyl]-1,3-dioxo-2,3-dihydro-1H-isoindol-4-yl}-2-thiophenecarboxamide in tetrahydrofuran (0.2 mol/l) and dichloromethane (0.2 mol/l). The reaction mixture is stirred at room temperature for 4 h, and saturated aqueous sodium bicarbonate solution is added. After addition of dichloromethane and phase separation, the aqueous phase is extracted with dichloromethane. The combined organic phases are dried (sodium sulfate), filtered and concentrated under reduced pressure. Without further purification, the crude product is used for the next reaction.

A suspension of 5-chloro-N-{2-[3-(hydroxymethyl) benzyl]-1,3-dioxo-2,3-dihydro-1H-isoindol-4-yl}-2-thiophenecarboxamide and aminoguanidine nitrate (1.2 eq.) in ethanol (0.02 mol/l) is heated under reflux for 1 d, during which the precipitate is dissolved and another colorless solid precipitates. The precipitate is filtered off, washed with ethanol and dried.

MS (ESI): m/z (%)=481 ([M+H]⁺, 100), Cl pattern;
HPLC (Method 1): rt=4.61 min.

What is claimed is:
1. A compound of the formula (I)

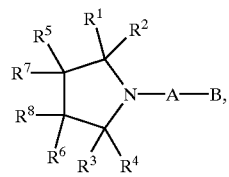

in which
$R^1$ and $R^2$ together represent O and
$R^3$ and $R^4$ together represent O, or
$R^1$ represents hydrogen, hydroxy or $(C_1-C_4)$-alkoxy,
$R^2$ represents hydrogen and
$R^3$ and $R^4$ together represent O, or
$R^1$ and $R^2$ together represent O,
$R^3$ represents hydrogen, hydroxy or $(C_1-C_4)$-alkoxy and
$R^4$ represents hydrogen,
$R^5$ and $R^6$ represent hydrogen and
$R^7$ and $R^8$ together represent

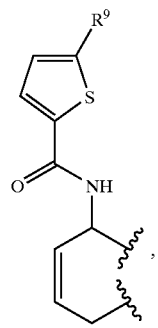

in which
$R^9$ represents halogen, trifluoromethyl or methyl, or
$R^5$, $R^6$, $R^7$ and $R^8$ together represent

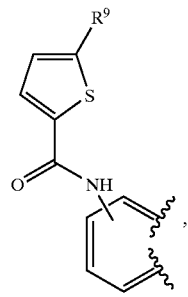

in which
$R^9$ is as defined above,
A represents $(C_1-C_4)$-alkanediyl or $(C_2-C_4)$-alkenediyl,
B represents phenylene or cyclohexanediyl, which radicals may be substituted by amino, urea, sulfamoyl,
—C(=N—NH—C(=NH)—NH₂)—H, or
—C(=NR¹⁰)—R¹¹,
in which
$R^{10}$ represents hydrogen or —NH—C(=NH)—NH₂,
$R^{11}$ represents —NR¹²R¹³ or 5- to 10-membered heterocyclyl, in which
R$^{12}$ and R$^{13}$, independently of one another, represent hydrogen, (C$_1$–C$_4$)-alkyl or (C$_3$–C$_7$)-cycloalkyl,
(C$_1$–C$_4$)-alkyl, which for its part may be substituted by cyano, (C$_1$–C$_4$)-alkoxycarbonyl, optionally (C$_1$–C$_4$)-alkyl-substituted 5- to 10-membered heterocyclyl, 5- to 10-membered heteroaryl, tri-(C$_1$–C$_4$)-alkylammonium, —NR$^{14}$R$^{15}$, —C(=NR$^{16}$)—R$^{17}$, —N—C(=O)—R$^{18}$ or —N—C(=O)—NH—R$^{19}$,
in which
R$^{14}$ represents hydrogen, mono- or di-(C$_1$–C$_4$)-alkylamino, (C$_1$–C$_4$)-alkyl which is optionally substituted by 5- to 10-membered heteroaryl, represents 5- to 10-membered heterocyclyl, (C$_6$–C$_{10}$)-aryl or 5- to 10-membered heteroaryl, where the rings for their part may be substituted by halogen,
R$^{15}$ represents hydrogen or optionally cyano-substituted (C$_1$–C$_4$)-alkyl,
R$^{16}$ represents hydrogen or hydroxy,
R$^{17}$ represents amino, 5- to 10-membered heterocyclyl, optionally amino- or trifluoromethyl-substituted mono- or di-(C$_1$–C$_4$)-alkylamino, optionally trifluoromethyl-substituted (C$_3$–C$_7$)-cycloalkylamino,
R$^{18}$ represents trifluoromethyl, (C$_1$–C$_4$)-alkyl, (C$_1$–C$_4$)-alkoxy or 5- to 10-membered heterocyclyl which is optionally substituted by (C$_1$–C$_4$)-alkyl,
R$^{19}$ represents hydrogen, amino, dimethylamino, 5- to 10-membered heterocyclyl, 5- to 10-membered heteroaryl, or represents (C$_1$–C$_4$)-alkyl which is optionally substituted by (C$_1$–C$_4$)-alkoxycarbonyl, dimethylamino, carbamoyl or 5- to 10-membered heteroaryl,
(C$_1$–C$_4$)-alkoxy, which for its part may be mono- or disubstituted, independently of one another, by cyano, thiocarbamoyl, optionally (C$_1$–C$_4$)-alkyl-substituted 5- to 10-membered heterocyclyl, optionally halogen-substituted 5- to 10-membered heteroaryl, optionally —C(=NR$^{20}$)—R$^{21}$-substituted (C$_6$–C$_{10}$)-aryl or —C(=NR$^{20}$)—R$^{21}$,
in which
R$^{20}$ represents hydrogen, hydroxy, (C$_3$–C$_7$)-cycloalkyl or optionally hydroxy-substituted (C$_1$–C$_4$)-alkyl,
R$^{21}$ represents amino, (C$_1$–C$_4$)-alkylthio, (C$_3$–C$_7$)-cycloalkylamino, benzylamino or 5- to 10-membered heterocyclyl,
5- to 10-membered heterocyclyl which for its part may be substituted by (C$_1$–C$_4$)-alkyl,
(C$_6$–C$_{10}$)-aryl which for its part may be mono- or disubstituted, independently of one another, by halogen, cyano, carbamoyl or optionally amino-substituted (C$_1$–C$_4$)-alkyl,
5- to 10-membered heteroaryloxy which for its part may be substituted by amino or N—(C$_1$–C$_4$)-alkylaminocarbonyl,
or 5- to 10-membered heteroaryl which for its part may be substituted by amino,
or a salt hydrate, hydrate of the salt, or solvate thereof.

2. The compound as claimed in claim 1
in which
R$^1$ and R$^2$ together represent O and
R$^3$ and R$^4$ together represent O, or
R$^1$ represents hydrogen, hydroxy, methoxy or ethoxy,
R$^2$ represents hydrogen and
R$^3$ and R$^4$ together represent O, or
R$^1$ and R$^2$ together represent O,
R$^3$ represents hydrogen, hydroxy, methoxy or ethoxy and
R$^4$ represents hydrogen,
R$^5$ and R$^6$ represent hydrogen and
R$^7$ and R$^8$ together represent

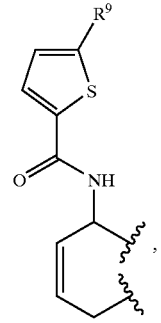

in which
R$^9$ represents halogen or trifluoromethyl, or
R$^5$, R$^6$, R$^7$ and R$^8$ together represent

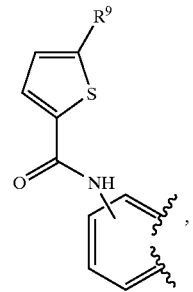

in which
R$^9$ is as defined above,
A represents (C$_1$–C$_3$)-alkanediyl or (C$_2$–C$_3$)-alkenediyl,
B represents phenylene or cyclohexanediyl, which radicals may be substituted by —C(=NR$^{10}$)—R$^{11}$
in which
R$^{10}$ represents hydrogen,
R$^{11}$ represents —NR$^{12}$R$^{13}$ or 5- to 10-membered heterocyclyl,
in which
R$^{12}$ and R$^{13}$, independently of one another, represent hydrogen, (C$_1$–C$_4$)-alkyl or (C$_3$–C$_7$)-cycloalkyl,
methyl or ethyl which for their part may be substitued by cyano, methoxycarbonyl, optionally methyl- or ethyl-substituted 5- or 6-membered heterocyclyl, 5- or 6-membered heteroaryl, tri-(C$_1$–C$_2$)-alkylammonium, —NR$^{14}$R$^{15}$, —C(=NR$^{16}$)—R$^{17}$, —N—C(=O)—R$^{18}$ or —N—C(=O)—NH—R$^{19}$,
in which
R$^{14}$ represents hydrogen, dimethylamino, methyl or ethyl, which radicals are optionally substituted by 5- or 6-membered heteroaryl, represents 5- or 6-membered heterocyclyl or 5- or 6-membered heteroaryl, which may be substituted by halogen,
R$^{15}$ represents hydrogen, methyl or ethyl,
R$^{16}$ represents hydrogen,
R$^{17}$ represents amino, 5- or 6-membered heterocyclyl, optionally amino- or trifluoromethyl-substituted mono- or di-(C$_1$–C$_4$)-alkylamino, optionally trifluoromethyl-substituted (C$_3$–C$_7$)-cycloalkylamino, $R^{18}$ represents trifluoromethyl or $(C_1-C_4)$-alkyl, $R^{19}$ represents hydrogen, amino or optionally methoxy- or ethoxycarbonyl-substituted $(C_1-C_4)$-alkyl, methoxy or ethoxy which for their part may be mono- or disubstituted, independently of one another, by optionally methyl-substituted 5- or 6-membered heterocyclyl or —C(=NR$^{20}$)—R$^{21}$, in which $R^{20}$ represents hydrogen, $R^{21}$ represents amino, $(C_3-C_6)$-cycloalkylamino, benzylamino or 5- or 6-membered heterocyclyl, or pyridyl, or a salt, hydrate, hydrate of the salt, or solvate thereof.

3. The compound as claimed in claim 1
in which
$R^1$ and $R^2$ together represent O and
$R^3$ and $R^4$ together represent O, or
$R^1$ represents hydrogen, hydroxy or methoxy,
$R^2$ represents hydrogen and
$R^3$ and $R^4$ together represent O, or
$R^1$ and $R^2$ together represent O,
$R^3$ represents hydrogen, hydroxy or methoxy and
$R^4$ represents hydrogen,
$R^5$ and $R^6$ represent hydrogen and
$R^7$ and $R^8$ together represent

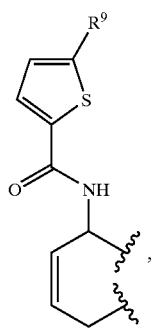

in which
$R^9$ represents chlorine or bromine, or
$R^5$, $R^6$, $R^7$ and $R^8$ together represent

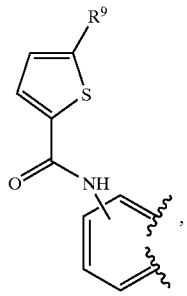

in which
$R^9$ is as defined above,
A represents methanediyl or ethanediyl,
B represents phenylene which may be substituted by —C(=NR$^{10}$)—R$^{11}$
in which
$R^{10}$ represents hydrogen,
$R^{11}$ represents amino, methyl which for its part may be substituted by cyano, optionally methyl-substituted imidazolinyl or tetrahydropyrimidinyl, —NR$^{14}$R$^{15}$ or —C(=NR$^{16}$)—R$^{17}$, in which $R^{14}$ represents optionally pyridyl-substituted methyl or pyridyl, $R^{15}$ represents hydrogen, $R^{16}$ represents hydrogen, $R^{17}$ represents amino, piperidinyl, morpholinyl, pyrrolidinyl, optionally amino- or trifluoromethyl-substituted mono- or di-$(C_1-C_3)$-alkylamino or optionally trifluoromethyl-substituted cyclopropyl-, cyclopentyl- or cyclohexylamino, or methoxy or ethoxy which for their part may be substituted by —C(=NH)—NH$_2$, or a salt, hydrate, hydrate of the salt, or solvate thereof.

4. A process for preparing compounds of the formula (1) as defined in claim 1, characterized in that either (A) a compound of the formula (IV)

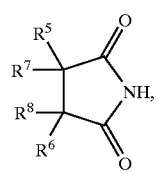

(IV)

in which $R^5$, $R^6$, $R^7$ and $R^8$ are as defined in claim 1 is reacted with a compound of the formula (V)

Y-A-B in which A and B are as defined in claim 1 and Y represents a suitable leaving group to give a compound of the formula (I)
in which both $R^1$ and $R^2$ and $R^3$ and $R^4$, in each case together, represent O and $R^5$, $R^6$, $R^7$, $R^8$, A and B are as defined in claim 1, or (B1) a compound of the formula (VIII) or (VIIIa)

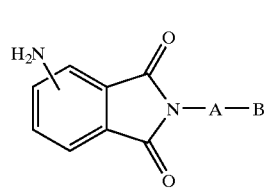

(VIII)

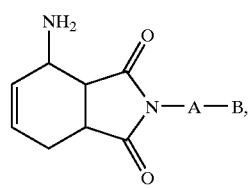

(VIIIa)

in which A and B are as defined in claim 1 is reacted with a compound of the formula (III)

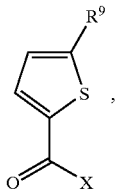
(III)

in which $R^9$ is as defined in claim 1 and X represents a leaving group
to give a compound of the formula (I)
in which both $R^1$ and $R^2$ and $R^3$ and $R^4$, in each case together, represent O and $R^5$, $R^6$, $R^7$, $R^8$, A and B are as defined in claim 1, or (B2) a compound of the formula (IX)

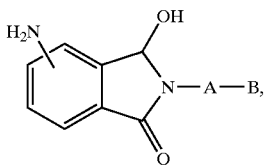
(IX)

in which A and B are as defined in claim 1
or a compound of the formula (X)

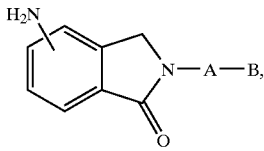
(X)

in which A and B are as defined in claim 1
is reacted with a compounds a compound of the formula (III) to give a compound of the formula (I)
in which $R^1$ and $R^2$ together represent O, $R^3$ represents hydrogen or hydroxy, $R^4$ represents hydrogen or $R^3$ and $R^4$ together represent O, $R^1$ represents hydrogen or hydroxy, $R^2$ represents hydrogen and $R^5$, $R^6$, $R^7$, $R^8$, A and B are as defined in claim 1, or (C) a compound of the formula (XIV)

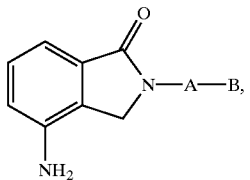
(XIV)

in which A and B are as defined in claim 1
is reacted with a compound of the formula (III) to give a compound of the formula (I)
in which $R^1$ and $R^2$ represent hydrogen, $R^3$ and $R^4$ together represent O and $R^5$, $R^6$, $R^7$, $R^8$, A and B are as defined in claim 1,
where the resulting compound of the formula (I) may, if appropriate, subsequently be subjected to further derivatization which can be carried out by customary methods.

5. A pharmaceutical composition, comprising at least one compound of the formula (I) as defined in claim 1 and at least one further auxiliary.

6. A pharmaceutical composition, comprising at least one compound of the formula (I) as defined in claim 1 and at least one further active compound.

7. A method for the treatment of thromboembolic disorders, comprising administering an effective amount of a compound of claim 1.

8. A method for treatment of disseminated intravascular coagulation (DIC) comprising administering an effective amount of a compound of claim 1.

9. A method for treatment of atherosclerosis, arthritis, or Alzheimer's disease comprising administering an effective amount of a compound of claim 1.

10. A method for preventing the coagulation of blood in vitro, characterized in that a compound of the formula (I) as defined in claim 1 is added.

11. The method of claim 7 wherein said thromboembolic disorder is myocardial infarction, angina pectoris, reocclusion and restenosis after angioplasty or aortocoronary bypass, stroke, transitory ischemic attack, peripheral arterial occlusive disease, pulmonary embolism or deep venous thrombosis.

12. The method of claim 11 wherein said angina pectoris is unstable angina.

13. The method of claim 10, wherein said blood is banked blood or a biological sample containing factor Xa.

* * * * *